US012195731B2

(12) United States Patent
Raymond

(10) Patent No.: US 12,195,731 B2
(45) Date of Patent: Jan. 14, 2025

(54) METHODS AND COMPOSITION FOR TARGETED GENOMIC ANALYSIS

(71) Applicant: Salish Bioscience Inc., Seattle, WA (US)

(72) Inventor: Christopher K. Raymond, Seattle, WA (US)

(73) Assignee: Salish Bioscience Inc., Seattle, WA (US)

( * ) Notice: Subject to any disclaimer, the term of this patent is extended or adjusted under 35 U.S.C. 154(b) by 951 days.

(21) Appl. No.: 17/261,970

(22) PCT Filed: Jul. 23, 2019

(86) PCT No.: PCT/US2019/043005
§ 371 (c)(1),
(2) Date: Jan. 21, 2021

(87) PCT Pub. No.: WO2020/023493
PCT Pub. Date: Jan. 30, 2020

(65) Prior Publication Data

US 2021/0292750 A1 Sep. 23, 2021

Related U.S. Application Data

(60) Provisional application No. 62/702,824, filed on Jul. 24, 2018.

(51) Int. Cl.
*C12N 15/10* (2006.01)

(52) U.S. Cl.
CPC ................................ *C12N 15/1068* (2013.01)

(58) Field of Classification Search
None
See application file for complete search history.

(56) References Cited

U.S. PATENT DOCUMENTS

| | | | | |
|---|---|---|---|---|
| 10,676,734 | B2 * | 6/2020 | Tang | C12N 15/1065 |
| 2001/0034048 | A1 | 10/2001 | Kurn | |
| 2005/0244847 | A1 | 11/2005 | Domanico et al. | |
| 2011/0269194 | A1 | 11/2011 | Makarov | |
| 2012/0196279 | A1 | 8/2012 | Underwood et al. | |
| 2014/0065692 | A1 * | 3/2014 | Kurn | C12Q 1/6806 435/194 |
| 2014/0274731 | A1 * | 9/2014 | Raymond | C12Q 1/6888 506/17 |
| 2015/0011396 | A1 | 1/2015 | Schroeder et al. | |
| 2016/0152972 | A1 * | 6/2016 | Stapleton | C12Q 1/6806 506/4 |
| 2017/0342475 | A1 | 11/2017 | Makarov et al. | |
| 2018/0112263 | A1 | 4/2018 | Arnold | |
| 2018/0142234 | A1 | 5/2018 | Raymond et al. | |

FOREIGN PATENT DOCUMENTS

| | | | |
|---|---|---|---|
| WO | 2010/148039 | A2 | 12/2010 |
| WO | 2015/117040 | A1 | 8/2015 |
| WO | 2016/170147 | A1 | 10/2016 |
| WO | 2017/083562 | A1 | 5/2017 |

OTHER PUBLICATIONS

Ukai et al., A new technique to prevent self-ligation of DNA, Journal of Biotechnology, 2002, 97, pp. 233-242 (Year: 2002).*

Ahern, Biochemical, Reagents Kits Offer Scientists Good Return on Investment, The Scientist, 1995, pp. 1-5 (Year: 1995).*

International Preliminary Report on Patentability mailed on Jan. 26, 2021, issued in corresponding International Patent Application No. PCT/US2019/043005, filed Jul. 23, 2019, 13 pages.

Goodwin, S., et al., "Coming of Age: Ten Years of Next-Generation Sequencing Technologies," Nature Reviews Genetics 17(6):333-351, May 2016.

International Search Report mailed Nov. 1, 2019, issued in corresponding International Patent Application No. PCT/US2019/043005, filed Jul. 23, 2019, 5 pages.

Paweletz, C.P., et al., "Bias-Corrected Targeted Next-Generation Sequencing for Rapid, Multiplexed Detection of Actionable Alternations in Cell-Free DNA From Advanced Lung Cancer Patients," Clinical Cancer Research 22(4):915-922, Feb. 2016.

(Continued)

*Primary Examiner* — Nancy J Leith
*Assistant Examiner* — Jessica D Parisi
(74) *Attorney, Agent, or Firm* — Christensen O'Connor Johnson Kindness PLLC

(57) ABSTRACT

The disclosure provides methods and reagents for preparing DNA libraries from biological materials for targeted sequencing. The approach can enhance the efficiency and sensitivity of targeted sequencing applications, such as liquid biopsy analyses to assess genetically driven conditions. In an embodiment, the disclosed method comprises attaching the 5' end of an oligonucleotide adapter to the 3' end of double-stranded DNA fragment to produce an adapter/fragment chimeric molecule; producing at least one complementary strand of the adapter/fragment chimeric molecule by linear amplification; hybridizing the at least one complementary strand with an oligonucleotide probe, wherein the oligonucleotide probe comprises a hybridization domain with a sequence that hybridizes to a target sequence in the complement strand to produce a targeted complement strand/probe duplex; purifying the targeted complement strand/probe duplex; and extending the probe in the purified targeted complement strand/probe duplex and amplifying with PCR to produce a plurality of sequencing template molecules.

23 Claims, 8 Drawing Sheets

Specification includes a Sequence Listing.

(56) References Cited

OTHER PUBLICATIONS

Written Opinion mailed Nov. 1, 2019, issued in corresponding International Patent Application No. PCT/US2019/043005, filed Jul. 23, 2019, 11 pages.
Extended European Search Report mailed May 23, 2022, issued in EP Application No. 19840255.4, filed Jul. 23, 2019, 11 pages.

* cited by examiner

STEP 1: ATTACHMENT OF LINDA OLIGONUCLEOTIDES

STEP 2: LINEAR AMPLIFICATION OF COMPLEMENTARY STRANDS

STEP 3: HYBRIDIZATION WITH FETCHER OLIGONUCLEOTIDE

METHODS AND COMPOSITION FOR TARGETED GENOMIC ANALYSIS

CROSS-REFERENCE TO RELATED APPLICATION

This application claims the benefit of Provisional Application No. 62/702,824, filed Jul. 25, 2018, the disclosure of which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 68524_Seq_2019-07-22.txt. The text file is 49 KB; was created on Jul. 22, 2019; and is being submitted via EFS-Web with the filing of the specification.

FIELD OF INVENTION

The present disclosure relates to the targeted analysis of genomic material from biological samples. For example, the disclosure addresses the compositions and methods for generating sequencing libraries for targeted sequencing of DNA, such as obtained in environmental or biological samples.

BACKGROUND

With the advent of next-generation sequencing technologies, massive amounts of DNA sequencing data can be produced quickly from starting samples. This data has advanced the ability to rapidly characterize the source sample from which the genomic templates were derived.

For example, in the context of disease diagnosis, cancers are diseases in which deleterious genomic changes have occurred. Disease-causing mutations in many cancers are discernable by DNA sequencing, provided source DNA can be obtained, and such genomic characterization can facilitate precision therapies. In this context, genomic analysis of cancer often involves characterization of neoplastic tissue obtained by a biopsy. However, many liquid and solid-type cancers release circulating tumor DNA fragments ("ctDNA") into bodily liquids such as the bloodstream. In healthy individuals without cancer as well as in cancer patients, an appreciable amount of fragmented DNA with normal DNA sequences is found in the cell-free plasma fraction of whole blood. An individual's normal DNA fragments are often described as "germline DNA" fragments, and the entirety of DNA present in blood plasma is often referred to as circulating, cell-free DNA ("cfDNA"). In subjects with cancer, a variable amount of ctDNA is present within the overall cfDNA. Cell-free DNA is also found in other bodily fluids such as urine, cerebral spinal fluid, saliva, and the like. The appreciation that readily accessible body fluids could serve as a source of tumor DNA coupled with the emergence of massively parallel DNA sequencing platforms (also referred to as next-generation sequencing or "NGS") has prompted the development of technologies for relatively non-invasive diagnosis and monitoring of cancers by detecting ctDNA from cfDNA samples. This is referred to as a "liquid biopsy." Thus, with the advancing power of sensitive NGS approaches, there is a growing appreciation for the utility of cfDNA sequencing in several areas of medicinal oncology.

Cancers can be identified by various different DNA lesions ("mutations") that occur within the DNA of diseased tissue cells. These include, but are not limited to, DNA point mutations, often referred to as single nucleotide variants (SNVs), that alter the function or expression of specific genes that either suppress the emergence of tumors ("tumor suppressors") or that stimulate uncontrolled proliferation of neoplastic tissue ("oncogenes"). Similarly, insertions or deletions of DNA sequence ("indels") that alter gene function are also commonly associated with certain cancers. Genomic rearrangements in which normally separate chromosomal segments becomes fused can also generate fusions between genes whose chimeric product drives tumorigenesis ("fusions"). Large-scale chromosomal rearrangements are also common in cancer and such rearrangements can either increase gene copy number ("amplifications") or decrease copy number ("deletions"). Both lesion types can alter the expression patterns of the affected genes and thereby promote tumor growth. Finally, certain cancer types create global genomic signatures that include loss-of-heterozygosity (LOH), meaning the normally diploid parental genotype is converted to a uniparental state with or without accompanying chromosome loss. Additional signatures in tumor cells include microsatellite instability in which the number of copies of repeat sequences within repetitive DNA elements either expand or contract and/or global changes in chromosomal ploidy that alter the overall number of chromosomes and the copy number relationships between chromosomes. Tumors with these latter lesion types are good candidates for response to immune checkpoint therapies and therefore essential elements of liquid biopsy genomic analysis.

Liquid biopsies potentially have considerable advantages over conventional tissue-based genomic analysis. By way of example, a hypothetical patient can be diagnosed with non-small cell lung cancer (NSCLC) that is of the adenocarcinoma subtype using a fine needle biopsy. However, the technique does not provide adequate tissue for genomic analysis of the tumor. A liquid biopsy of this patient could provide a definitive diagnosis that the causal mutations driving tumor growth are one of several potential types that are treatable with targeted therapy. The advantage of this diagnostic procedure is that it does not require an invasive tissue biopsy that is both time-consuming and poses a significant additional health risk to the patient. The results of the liquid biopsy are available within days, rather than weeks for a tissue biopsy. Considering that in many cancer treatments time is of the essence, the efficiency of diagnosis can provide a critical head start in appropriate therapies. Finally, the liquid biopsy is considerably less expensive than the surgical excision of tissue from deep within a bodily organ. This is especially true when the fact that not all tissue biopsy specimens provide definitive results is taken into account. Collectively, the liquid biopsy is therefore less expensive, faster and more reliable, all of which suggest that this diagnostic procedure will likely become the standard of care for certain types of cancers.

While the argument can be made that liquid biopsies should be the first line standard of care in the genomic diagnosis of newly detected cancer, the greater utility of liquid biopsies is also likely to be in the monitoring of disease relapse, monitoring of unresectable tumor proliferation, and monitoring of treatment efficacy. With respect to disease relapse, some cancers are likely to relapse with resistance mutations against the initial targeted therapy. Continued quality of life is possible by switching to therapies that overcome the disease resistance mechanism. In this scenario, liquid biopsies can have two applications, the first being monitoring for relapse of the disease and the second being diagnosis of treatment resistance. With respect to unresectable (e.g. metastatic) tumors, radiological imaging is currently the standard of care for monitoring tumor burden. There is often little difference in the images of a successfully treated tumor that has become necrotic scar tissue versus a tumor resistant to treatment. Evidence is accumulating that the amount of ctDNA is profoundly different between these two scenarios, with ctDNA being essentially undetectable with successful treatment as opposed to increasing ctDNA levels in patients with resistant tumors. This emerging scenario, where responsive tumors cease shedding ctDNA while recalcitrant tumors continue to release tumor DNA fragments, can have profound impact on the patient treatment and the cost of oncology healthcare. The benefit of early treatment monitoring using ctDNA levels measured by liquid biopsies is that responsive patients should continue treatment while non-responders can be switched to different therapies before the disease progresses further. With respect to cost containment, many targeted therapies are exorbitantly expensive even though treatment efficacy is rarely 100%. Given the possibility that it is possible to monitor treatment efficacy using ctDNA levels detected by liquid biopsy within days or weeks of treatment initiation, such immediate testing of treatment efficacy could be used to identify patients that are benefitting from an expensive therapy versus those that are not and need to consider alternative approaches. In all of these scenarios, the liquid biopsy technology must possess the capacity to quantitatively measure ctDNA levels against the background of normal, circulating cfDNA. Furthermore, this ability for quantitative assessment must persist in the context where relative target ctDNA levels are diminishingly small compared to the background cfDNA.

However, current methodologies of obtaining and processing source samples fail to fully leverage the power and sensitivity of NGS platforms to accurately detect rare sequences. Again in the context of cancer diagnosis, healthy human donors have about 5 ng of cfDNA per 1 mL of plasma. Certain conditions increase this level, including strenuous exercise, pregnancy, chemotherapy, cancer, and autoimmune diseases. One haploid human genome has a mass of 3.3 pg, hence there are 1500 haploid genomes/mL plasma in a healthy donor. In the setting of cancer, the fraction of cfDNA that is tumor-derived ctDNA may be very low, meaning less than 1%, less than 0.1%, and often even lower. This corresponds to 15 tumor-derived genomes/mL plasma at 1% “allele fraction”, and 1.5 tumor-derived genomes/mL plasma at 0.1% allele fraction, defined as the proportion of cancer-related sequences relative to the total number of sequences recovered from the sample. Moreover, the sensitivity of sequence-based methods for detecting rare variants is directly proportional to the number of cfDNA fragments that are “converted” into analyzable DNA molecules. In the context of NGS, “conversion” means attachment of additional adapter oligonucleotides to the cfDNA such that it is amenable to DNA sequencing. However, such conversion efficiencies are rarely rigorously measured by entities offering cfDNA analysis services or kits. Given the potentially low initial number of disease-indicative fragments in cfDNA, current low conversion rates represent a major weakness in the current state of the art.

Conventional DNA cloning methods rely on the attachment of adapter molecules to both ends of a source DNA fragment followed by a DNA amplification scheme (i.e. PCR). If adapter attachment to one end of the DNA fragment fails, then the fragment is lost from the subsequent analysis. Additionally, most cloning schemes rely on polishing and modification (e.g. A-tailing and/or 5' end phosphorylation) of cfDNA fragment ends, and as described above, failure to A-tail and/or phosphorylate 5' ends leads to failure of adapter attachment and therefore loss of the fragment from downstream analysis. Additionally, formation of adenylylated DNA intermediates that dissociate from the ligase enzyme prior to phosphodiester bond formation are relatively common byproducts in DNA ligation reactions, and these intermediates are blocked from further attachment to adapters. These deficiencies lead to bias of the signal and loss of sequence information, which given the rarity of some targets, such as disease markers, can result in critical mischaracterization and misdiagnosis.

Thus, despite the advances in the art of next generation sequencing platforms and understanding of the genetics of diseases, there remain critical deficiencies in the art in providing rapid, sensitive, and inexpensive strategies to survey biological samples for known target sequences. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a method for generating a DNA library for targeted sequencing. The method comprises:

a) attaching the 5' end of an oligonucleotide adapter to the 3' end of double-stranded DNA fragment to produce an adapter/fragment chimeric molecule;

b) producing at least one complementary strand of the adapter/fragment chimeric molecule by linear amplification;

c) hybridizing the at least one complementary strand with an oligonucleotide probe, wherein the oligonucleotide probe comprises a hybridization domain with a sequence that hybridizes to a target sequence in the complement strand to produce a targeted complement strand/probe duplex;

d) purifying the targeted complement strand/probe duplex; and e) extending the probe in the purified targeted complement strand/probe duplex and amplifying with PCR to produce a plurality of sequencing template molecules.

The method can be followed by conducting DNA sequencing of the plurality of sequencing molecules using an appropriate next generation sequencing platform.

In another aspect, the disclosure provides a kit. The kit can comprise: an oligonucleotide adapter, a DNA polymerase with 3' to 5' exonuclease activity capable of creating blunt ends on double-stranded DNA, a plurality of enzymes that mediate DNA repair, a DNA ligation enzyme, and written indicia instructing the performance of the method disclosed herein. In some embodiments, the kit also comprises DNA oligonucleotide probes for target-specific retrieval of genomic loci.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A illustrates the input material is isolated or purified dsDNA (10) (e.g., cfDNA). FIG. 1B illustrates Step 1, wherein the attachment of a multifunctional oligonucleotide adapter (20; also referred to as a "LINDA oligonucleotide") to the 3' ends of dsDNA (10) to produce an adapter/fragment chimeric molecule (30). The black dots in FIG. 1B represent the phosphodiester bond between the LINDA adapter (20) and the sample DNA fragment that is created by DNA ligation. FIG. 1C illustrates Step 2, wherein a linear amplification generates one or more target template strands (50) that are complementary strands of the adapter/fragment chimeric molecule (30) using a first primer (40). FIG. 1D illustrates Step 3, wherein a targeting oligonucleotide probe (70; also referred to as a "Fetcher oligonucleotide probe") is hybridized to the complementary template strand (50). This is followed by thermal and physical purification of the targeted complement strand/oligonucleotide probe duplex (60) and primer extension of the oligonucleotide (Fetcher) probe (50) using the target complement strand (50) as the template. FIG. 1E illustrates Step 4, wherein PCR amplification is conducted on the extended template (80) using platform-specific forward and reverse PCR primers (90 and 100, respectively) to generate sequencing template molecules (not shown) and thereby complete the targeted dsDNA sequencing library construction process. FIG. 1F illustrates subsequent application of paired-end DNA sequencing of the sequencing template molecules (110) using platform appropriate sequencing forward and reverse primers (120 and 130, respectively) that can be used to obtain sequence information required for later analysis.

FIG. 2A illustrates one design concept where the strand ligated to the double-stranded DNA "ligation strand") has an annealing domain (22) for amplification at the 3' end, with an internal clone tag domain (24), and a sample tag domain (26) at the 5' end. In the illustrated embodiment, there is a complementary duplex oligonucleotide (140) hybridized over the 3' end serving as the "partner strand" to provide an adapter duplex (145). The complementary duplex oligonucleotide (140) has a C3 spacer at its 3' end. FIG. 2B illustrates another embodiment wherein the design is reversed and which was shown to provide a higher yield of clones with intact sample tags. Specifically, the "partner strand" has domains corresponding to the annealing domain (22) for amplification at the 5' end, with an internal clone tag domain (24), and a sample tag domain (26) at the 3' end, with a C3 spacer at the 3' end. The squiggle represents an internal C3 spacer (144) inserted within the oligonucleotide near the 5' end. The "ligation strand" is extended by a DNA polymerase during the adapter attachment (ligation) process by copying from the hybridized complementary duplex oligonucleotide (142) of the adapter duplex (146) using the "partner strand" as the template. As in FIG. 1D, the diagram indicates direction of primer extension with an arrow to create the full-length "ligation strand". Ultimately, the "ligation strand" of either embodiment (e.g., in FIGS. 2A and 2B) is shown in FIG. 1B as element (20).

FIG. 3A illustrates an embodiment wherein the oligonucleotide probe comprises a hybridization domain (72) at the 3' end. The −40 nt hybridization domain comprises a sequence that hybridizes with a target sequence (e.g., in a target dsDNA fragment (10)) that will appear in the linearly amplified complementary strand (50; see FIGS. 1C and 1D) and a −45 nt tail section that is common to the set of Fetcher oligonucleotide probes with a primer annealing domain (74) at the 5' end. The primer annealing domain (74) facilitates purification of targeted complement strand/probe duplexes (60) and later amplification of sequencing template molecules (110). FIG. 3B illustrates an additional embodiment of the oligonucleotide probes design used in proof-of-principle studies. A −45 nt duplexing oligonucleotide (147) complementary to the tail sequence was added. The complementary duplex oligonucleotide (147), which anneals to the Fetcher tail (e.g., 74) sequence, includes a terminal biotin-containing modification for purification with streptavidin-coated magnetic beads and one or more internal dideoxyuracil bases (148) for cleavage of the targeted complement strand/probe duplexes from the beads following purification.

DETAILED DESCRIPTION

The present disclosure addresses targeted sequence analysis of DNA in samples that address and overcome many of the deficiencies of the available art. The disclosed strategy can be applied to any sample, e.g., biological or environmental, where reference genomic sequence for the target DNA to be detected and sequenced is known. This description is presented within the context of a particularly relevant and useful application, namely the targeted detection of known genetic markers presented in cfDNA from liquid biopsy samples from subjects that potentially have cancer. However, it will be appreciated by persons of ordinary skill in the art that the disclosed reagents and methodologies can be equally and readily applied to detection of heterologous DNA (such as in infections) from a host sample. Alternatively, the disclosure also encompasses analysis of environmental samples for the presence of known genomic sequence to identify whether a particular organism (with a unique genetic profile) is present.

In accordance with the foregoing, in one aspect, the disclosure provides a method for generating a DNA library for targeted sequencing. The method comprises the following steps:

a) attaching the 5' end of an oligonucleotide adapter to the 3' end of double-stranded DNA fragment to produce an adapter/fragment chimeric molecule;
b) producing at least one complementary strand of the adapter/fragment chimeric molecule by linear amplification;
c) hybridizing the at least one complementary strand with an oligonucleotide probe, wherein the oligonucleotide probe comprises a hybridization domain with a sequence that hybridizes to a target sequence in the complement strand to produce a targeted complement strand/probe duplex;
d) purifying the targeted complement strand/probe duplex; and
e) extending the probe in the purified targeted complement strand/probe duplex and amplifying with PCR to produce a plurality of sequencing template molecules.

Figure 1A:
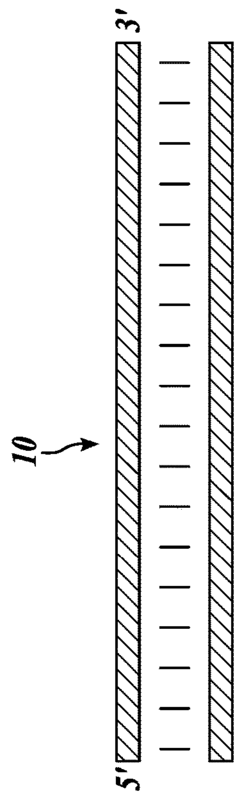
FIGS. 1A-1F provide a schematic overview of an exemplary embodiment of the disclosed process for targeted sequence analysis of genomic DNA. Illustrated is a cartoon scheme showing an illustrative four-step process for generating sequencing libraries from purified cell-free DNA according to an embodiment of this disclosure. While this scheme illustrates the modification steps for a single molecule, it will be understood that this process can be scaled up to address one or multiple batches of a plurality of dsDNA fragments (e.g., cfDNA as isolated from one or more biological samples).

A schematic representation of an exemplary embodiment of the method is provided in FIGS. 1A-IF.

Attaching an Oligonucleotide Adapter

As indicated above, the typical sequencing library is constructed by initially amplifying template, including rare template molecules, by attaching adapter molecules on both strands of dsDNA to facilitate PCR-based amplification. However, these approaches suffer loss of input template molecules, especially rare template molecules, from the library due to improper or incomplete attachment of one of the end adapters required for initial amplification of the template. A key advantage of the present disclosure is that attachment of only a single adapter to one end of the DNA is sufficient to support subsequent generation and analysis of the DNA fragment.

The disclosed method provides for attachment of the 5' end of an oligonucleotide adapter (20; also referred to as "LINDA oligonucleotide") to the 3' ends of dsDNA (10) to produce an adapter/fragment chimeric molecule (30). See FIG. 1B. Embodiments of the oligonucleotide adapter can comprise several defined domains and features that confer multiple functionalities. In some embodiments, the oligonucleotide adapter comprises a phosphate group on the 5' end. In this configuration, it is the adapter that provides the phosphate required for attaching the adapter to the 3' end of a strand of the dsDNA molecule. Accordingly, attachment of the adapter molecule does not rely on the state of the dsDNA molecule. If, by chance, an adapter molecule were to lack such 5' phosphate, then it would fail to participate in fragment ligation. However, when performed practically at scale with multiple molecules, another adapter molecule that has a 5' phosphate takes its place and attaches successfully. Similarly, if an adapter duplex dissociates from ligase as an adenylylated DNA intermediate, this abortive process will not decrease conversion efficiency of the process. The dsDNA fragments have the simpler requirement that they must be blunt-ended with a free 3' hydroxyl group to support adapter attachment, and empirical observations suggest that the adapter attachment efficiency in the present scheme approach 100% efficiency.

In some embodiments, the oligonucleotide adapter (20) comprises a primer annealing domain (22) with a nucleotide sequence that permits linear or exponential PCR amplification upon annealing of a primer. See FIGS. 1B, 2A, and 2B. The primer annealing domain (22) can be configured to be any length that allows annealing of a primer for purposes of linear or exponential amplification (such as in typical PCR methodologies). Exemplary lengths are between about 15 and about 45 nucleotides, such as about 20, about 25, about 30, about 35, about 45 nucleotides or more. While the sequence is not limited to a particular sequence or set of sequences, it must be known a priori such that appropriate primers can be utilized later in the method to anneal and extend from the created duplexes. The primer annealing domain (22) is typically at the 3' end of the oligonucleotide adapter (20) relative to other domain discussed below.

In some embodiments, the oligonucleotide adapter comprises a clone tag domain (24) with a nucleotide sequence that uniquely labels each sequencing template molecule comprising sequence derived from the initial oligonucleotide adapter (20). The clone tag domain (24) typically comprises a short series (e.g., 5, 6, 7, 8, 9, 10, or so) that are a random sequence of bases, e.g., where A, C, G, or T are randomly represented. When considered in aggregate (i.e., in a population of a plurality of oligonucleotide adapters), the sequence is degenerate. Thus, the sequence for any single oligonucleotide adapter (20) does not need to be known a priori. In theory, there are a total of 65,536 possible clone labels generated by this random nucleotide scheme for an 8 nucleotide clone tag domain (24). Following sequencing, the DNA sequence of a randomly generated clone label is combined with the mapping coordinates of dsDNA fragments, and this process generates a unique identifier for each dsDNA sequence. The phrases "map" and "mapping" are often used as a shorthand reference to the fact that a DNA sequence (i.e. an NGS sequence read) has the same or a similar nucleotide sequence as a particular segment of the target reference genome (e.g. the human genome). Such a match is also referred to as an "alignment," and the phrases map, map-able, mapping and aligning are related. DNA alignments are discovered by sequence matching computer algorithms (e.g. BLAST, BLAT, BOWTIE, etc.).

In some embodiments, the oligonucleotide adapter comprises a sample tag domain (26) with a nucleic acid sequence that labels independent samples of double-stranded DNA fragments and thereby allows multiplex analysis of multiple samples at once. Like the clone tag domain (24), the sample tag domain (26) typically comprises a short series (e.g., 5, 6, 7, 8, 9, 10, or so) of nucleotides. However, instead of a random sequence, the sample tag domain (26) has a predetermined sequence that uniquely identifies a batch or sample. For example, in a multiplex performance of the method, a first sample comprises DNA obtained from a first source, and a second sample comprises DNA obtained from a second source (e.g., a different subject or a different biological sample). These sources can be tracked by the sample tag domain that is incorporated into the sequencing library even if the components are eventually combined after the initial attaching steps are performed in parallel. Stated otherwise, this feature enables multiplexing of samples during DNA sequencing. Sequences belonging to specific samples can be identified by their specific sample label in post-NGS analysis. Many different adapter oligonucleotides can be used in the initial steps to multiplex and then differentiate between many samples that can be combined into a single NGS reaction. Of course it is also possible that many different adapter oligonucleotides could be attached to the same dsDNA sample, and this is sometimes necessary to promote proper base calling in some NGS platforms.

In some embodiments, the oligonucleotide adapter (20) comprises an annealing domain (22), a clone tag domain (24), and a sample tag domain (26). Typically, the annealing domain (22) is disposed on the 3' end of the oligonucleotide adapter (20) relative to the clone tag domain (24) and sample tag domain (26). In some embodiments, the clone tag domain (24) is internal, i.e., disposed between the annealing domain (22) and the sample tag domain (26). See, e.g., FIG. 1B.

In some embodiments, the oligonucleotide adapter comprises a modification in the 3' terminal phosphate linkage. Such a modification can serve to prevent or inhibit degradation by enzymatic action (e.g., degradation by enzymes with 3' to 5' exonuclease activity) that may be used in later steps of the method. In some embodiments, the modification of the 3' terminal phosphate linkage comprises a phosphorothioate modification. Other modifications that inhibit 3' to 5' exonuclease activity are known and encompassed by this disclosure. While it is preferable that such modification is implemented in the final linkage (i.e., the terminal phosphate linkage), this disclosure encompasses internal modifications, e.g., near the 3' terminal end, that serves this purpose and preserves the integrity of the remaining sequence that is 5' to the modification.

Figure 2A:
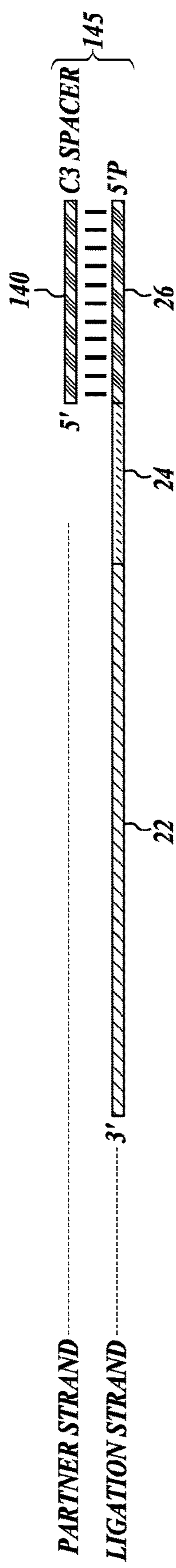
FIGS. 2A and 2B are cartoon illustrations of two illustrative designs of a ~45 nucleotide multifunctional oligonucleotide adapter (Linear amplification of DNA, or "LINDA" oligonucleotide) according to two embodiments of this disclosure.

To further facilitate attachment of the adapter oligonucleotide (20) to the dsDNA molecule (10) by DNA ligase, in some embodiments, the oligonucleotide adapter (20) comprises a complementary duplex oligonucleotide (140 and 142) annealed to at least its 5' end. See FIGS. 2A and 2B, respectively. The complementary duplex oligonucleotide comprises (140 and 142) a modification on its 3' end thereby preventing ligation of the double stranded DNA fragment to a complementary duplex such as another adapter duplex and facilitating attachment of the 5' end of the oligonucleotide adapter to the double stranded DNA fragment. FIG. 2A illustrates one design concept where the complementary duplex oligonucleotide (140) is hybridized over the 3' end serving as the "partner strand" to provide an adapter duplex (145). The complementary duplex oligonucleotide (140) has a C3 spacer at its 3' end. The C3 spacer is an exemplary modification that has three contiguous methyl groups and a 3' hydroxyl. This spacer precludes ligation to the illustrated partner strand but does not interfere with attachment (e.g., ligation) of the opposing ligation strand to the target dsDNA fragment.

Figure 1B:
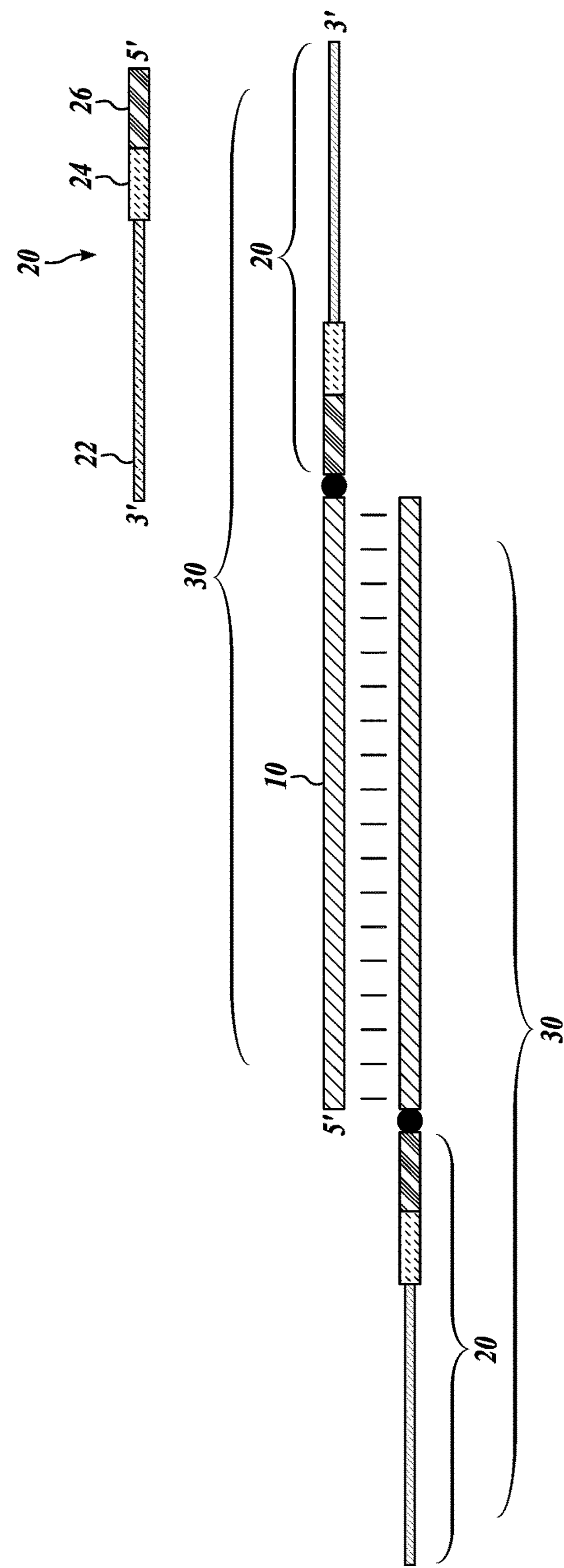
Figure 2B:
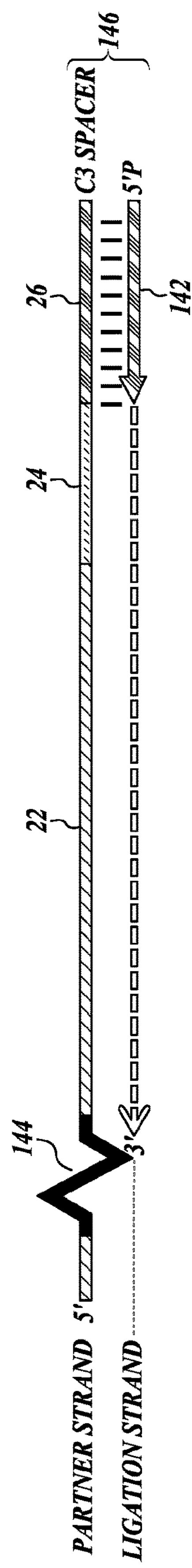

FIG. 2B illustrates another embodiment wherein the design is reversed and which was shown to provide a higher yield of clones with intact sample tags. Specifically, the "partner strand" has domains corresponding to the annealing domain (22) for amplification at the 5' end, with an internal clone tag domain (24), and a sample tag domain (26) at the 3' end, with a C3 spacer at the 3' end. The squiggle represents a modification (e.g., internal C3 spacer) (144) inserted within the oligonucleotide near the 5' end of the partner strand. This internal C3 spacer (144) is an exemplary structure with three contiguous methyl groups (3' ribose-CH2-CH2-CH2-5' phosphate) that serves as a very flexible tether to link the sequences on either side. The information on the complementary "partner strand" of the duplex is transferred onto the "ligation strand" during the ligation reaction by primer extension of complementary duplex oligonucleotide (142) in the adapter duplex (146), and the internal C3 spacer blocks extension by DNA polymerases and thereby prevents the complete replication of the "partner strand". Hence, this modification prevents the generation of adapter blunt ends that are themselves susceptible to blunt end ligations, which could otherwise diminish the quality of the sequencing library. After the extension, the "ligation strand" that incorporates the extended complementary duplex oligonucleotide (142) serves as the functional adapter oligonucleotide (20) that is physically attached at its 5' end to the 3' ends of dsDNA (10) (See FIG. 1B). The pre-existing 3' end spacer on the partner strand prevents its permanent attachment to any 3' end on the dsDNA (10) molecule.

The attachment of the oligonucleotide adapter to the 3' end of the dsDNA fragment comprises contacting the oligonucleotide adapter (20) and dsDNA fragment (10) with one or more DNA ligation enzymes. Exemplary, non-limiting DNA ligation enzymes include T4 DNA ligase and T3 DNA ligase. Other appropriate ligases are known and are encompassed by this disclosure. As will be understood, the activity of the appropriate DNA ligase can be supported by inclusion of the appropriate nucleotide triphosphates and other reaction buffer components known in the art.

Once the oligonucleotide adapter (20) is attached at its 5' end to the 3' end of a dsDNA molecule (10), the resulting structure is referred to an adapter/fragment chimeric molecule (30). As depicted in FIG. 1B, both ends of the dsDNA (10) can have an attached, extended ligation strand. Either strand of these adapter/fragment chimeric molecules (30) can then serve as a template for linear amplification in the next step, discussed below.

Initial dsDNA Processing

The attachment of the adapter oligonucleotide, described above, can be optionally preceded by steps to obtain ligateable ends on input dsDNA and/or to improve the quality of the input dsDNA molecules (10). The initial input material comprises genomic material obtained from a biological sample (e.g., a biopsy or bodily fluid) or an environmental sample. The method can further comprise active step(s) of obtaining the biological sample and/or extracting or isolating nucleic acids from the sample accordingly to techniques familiar to persons of ordinary skill in the art. Exemplary biological samples are tissue samples, including fixed samples (e.g., paraffin embedded or formalin fixed samples). Other biological samples are fluids obtained from a subject, such as blood (or components thereof), plasma, serum, saliva, cerebral spinal fluid, amniotic fluid, urine, feces, semen, and the like. In some embodiments, the input dsDNA is cfDNA. In some embodiments, the input dsDNA (e.g., cfDNA) is from a subject suspected of having a disease (e.g., cancer) or infection. The subject can be, e.g., a human, a non-human primate, mouse, rat, guinea pig, dog, cat, horse, cow, or other animal of veterinary concern or disease model utility.

Regardless of source, the input material is isolated or purified dsDNA (10) (e.g., cfDNA), as illustrated in FIG. 1A. In the context of liquid biological samples, cfDNA from individuals (healthy and with cancer) is often about 165 bp in length. This fragment size corresponds to the length of DNA that is wrapped around a single histone subunit and it is known to be generated by endonuclease cleavage between adjacent histone subunits. There are also fragments of 330, 500 and higher bps that are likely the DNA wrapped around two histones, three histones, etc., where endonuclease cleavage between adjacent histones did not occur. The ends of cfDNA are typically "ragged", meaning the cfDNA is a collection of DNA fragments with short 3' extensions, blunt ends, and 5' extensions. The evidence for this comes from the fact that blunt-end cloning of cfDNA is greatly enhanced by an initial "end-repair" step in which the ends of cfDNA molecules are treated with enzymes that "polish" the ends of fragments to uniform blunt ends. There also appears to be "DNA damage" in many cfDNA molecules, such as but not limited to nicks or gaps, modified bases and abasic sites that preclude conventional DNA cloning. The evidence for this comes from the observation that pretreatment of cfDNA with enzyme cocktails that can repair the types of DNA damage described above also enhance cfDNA cloning efficiency. Accordingly, in some embodiments, the method comprises repairing both the ends (also referred to as "polishing" the blunt ends) and the internal damage that may be present in the input dsDNA.

In some embodiments, the method can comprise dephosphorylating the 5' ends of the input dsDNA fragment prior to the attaching of step (a). This step prevents spurious ligations of one dsDNA molecule to another dsDNA molecule or to other nucleic acid molecules that may be present in the attachment reaction. The intended attachment partners, i.e., the oligonucleotide adapters, supply the required phosphate group to ensure the reactions are limited to intended attachments only. In some embodiments, dephosphorylating the 5' ends of the double-stranded DNA fragment comprises treating the DNA fragment with alkaline phosphatase. To illustrate, in one specific example, dephosphorylation can be achieved by a simple 30-minute incubation with recombinant shrimp alkaline phosphatase (rSAP) at 37° C. followed by heat inactivation of the enzyme at 65° C. for 5 min.

In some embodiments, the method further comprises contacting the input dsDNA fragment with one or more DNA polymerases with 3' to 5' exonuclease activity to create blunt ends on the double stranded DNA fragment prior to the attaching of step (a). Such activity provides input dsDNA with polished ends that are more amenable to the intended attaching of the adapter oligonucleotides. Exemplary, non-limiting DNA polymerases encompassed by the disclosure include T4 DNA polymerase and the Klenow fragment of *E. coli* DNA polymerase I. Other appropriate DNA polymerases are known and are encompassed by this disclosure. As will be understood, the activity of the appropriate DNA polymerases can be supported by inclusion of the appropriate deoxynucleotide triphosphates and other reaction buffer components known in the art.

In some embodiments, the method further comprises contacting the DNA fragment with one or more enzymes that mediate DNA repair prior to the attaching of step (a). Any appropriate DNA repair enzyme can be employed, depending on the condition or quality of the initial input dsDNA. The one or more repair enzymes can individually or in concert provide functionality to repair internal damage to physiologically exposed, circulating dsDNA, including repair of abasic sites, nicks, and gaps. In some exemplary embodiments, the DNA repair enzymes comprise full-length Bst DNA polymerase, Taq DNA ligase, Endonuclease IV, or any homologs or combinations thereof, many of which are commercially available. Endonuclease IV, for example, removes abasic residues by creating 1 nt gaps with 3' OH's and 5' phosphates. Bst full-length polymerase, for example, recognizes and fills nicks and gaps. Bst full-length polymerase also provides 5'-3' exonuclease activity, which is instrumental in generating ligate-able DNA nicks. Taq DNA ligase is a nick-specific, NAD+ driven ligase. The concerted action of these enzymes can repair a substantial fraction of the internal DNA damage in dsDNA, such as observed especially in cfDNA. Other appropriate DNA repair enzymes are known and are encompassed by this disclosure. As will be understood, the activity of the appropriate DNA repair enzymes can be supported by inclusion of the appropriate nucleotide triphosphates and other reaction buffer components known in the art.

In some embodiments, the reaction buffer that contains the DNA polymerase and/or one or more DNA repair enzymes from the preliminary steps is maintained when combining repaired input dsDNA with the oligonucleotide adapter and DNA ligation enzyme. The enzymes that catalyze these activities are mutually compatible and optimally active in the same reaction conditions. Specifically the reaction mixture can contain a mesophilic DNA polymerase with a 3' to 5' exonuclease activity, such as the Klenow fragment of *E. coli* DNA polymerase I or T4 DNA polymerase. In some embodiments, the mixture can also contain the repair enzymes represented by Endonuclease IV, Bst full length DNA polymerase, and Taq DNA ligase as described above. The mixture can also contain a DNA ligase such as T4 DNA ligase or T3 DNA ligase. Optionally, the dsDNA input can be dephosphorylated with heat-sensitive phosphatase such as alkaline phosphatase prior to the concurrent end-repair and adapter ligation step. The mixture can also contain a blend of deoxynucleotide triphosphates (required for DNA polymerization) and nucleotide triphosphates such as ATP (required by T4 DNA ligase). In the presence of these enzymatic activities, adapter attachment and primer extension of the adapter ligation strand can be catalyzed within a single reaction.

Linear Amplification

Figure 1C:
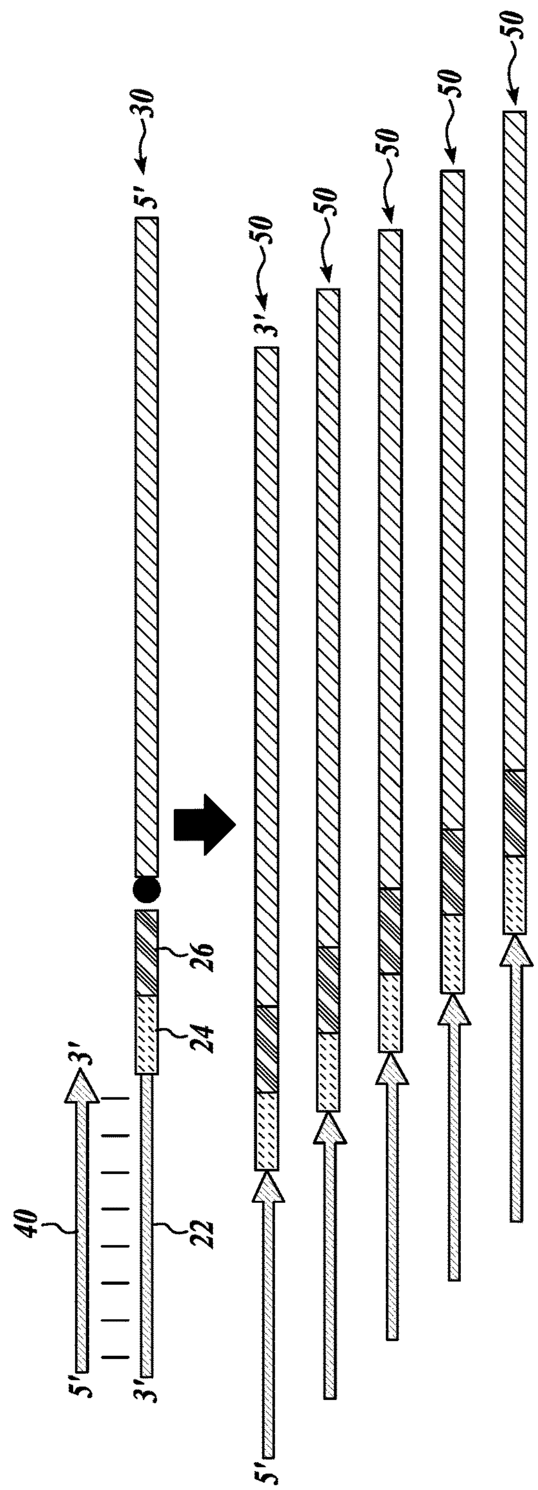

As indicated, the adapter/fragment chimeric molecule (30) serves as a template strand for primer-directed "linear amplification." See, e.g., FIG. 1C. As used here, the term "linear amplification" means a temperature cycled and primer (40) extension directed DNA copying method that employs the same basic principles as PCR. The major difference is that the adapter/fragment chimeric molecule (30) has a single primer binding site on its 3' end that facilitates the production of a single-stranded DNA copy (50) that is complementary to the adapter/fragment chimeric molecule (30) template. Unlike PCR, the copied complementary strand is not itself a template strand capable of making additional copies. Moreover, only one such complementary strand (50) is produced per thermal cycle, hence the amplification is linear rather than exponential, as is the case with PCR where primer binding sites occur on both ends of the template molecule and newly produced strand copies are themselves templates for additional copying. The production of DNA strands that are the complement of the initial DNA fragments is critical to the overall success of the disclosed method because the switch in fragment polarity from 3' adapter/fragment 5' to 5' adapter/fragment 3' is required for the next step in the disclosed method, which is the hybridization and annealing of target-specific oligonucleotides. At minimum, only a single cycle of linear amplification is required, however the disclosure encompasses more cycles. Often, spurious amplification byproducts are experienced after about 20 cycles, thus reducing the utility of even more cycles.

The linear amplification is facilitated by use of a first primer (40) that anneals to the primer annealing domain (22) of the oligonucleotide adapter (20) that was previously attached to the dsDNA fragment (10) and is now the 3' end of the adapter/fragment chimeric molecule (30) template. See FIG. 2C. The first primer (40) can be initially present in the reaction at, e.g., about 100 nM to 800 nM, about 200 nM to 600 nM, about 300 to about 500 nM. In some embodiments, the first primer (40) is initially present at about 400 nM in the linear amplification. The length and composition of the first primer (40) can be adjusted according to ordinary practice to facilitate efficient annealing and extension for linear amplification. Typical lengths can be ≥about 30 nt, ≥about 40 nt, ≥about 50 nt, or ≥about 60 nt. In some embodiments, a length of about 45 to 65 nt is preferable.

The extension process is mediated by a thermostable DNA polymerase. An illustrative, non-limiting example of a thermostable DNA polymerase encompassed by the disclosure is Q5 DNA polymerase, a recombinant enzyme available in the ULTRA™ II NGS prep kit from New England Biolabs. Other appropriate thermostable DNA polymerase enzymes are known and are encompassed by this disclosure. As will be understood, the activity of the appropriate thermostable DNA polymerase can be supported by inclusion of the appropriate deoxynucleotide triphosphates and other reaction buffer components known in the art.

In some embodiments, linear amplification comprises one or more rounds of a two-step thermal cycling procedure. For example, the first step is a melting step to separate any annealed or hybridized molecules from each other. For example, this can be conducted at about 98° C. for about 10 seconds. The second step has a lower temperature to permit primer annealing and extension. This can be conducted at, for example, 65° C. for about 30 seconds. Persons of ordinary skill in the art can optimize these exemplary conditions as necessary to accommodate different conditions and primer designs.

The linearly amplified complementary strands (50) can be optionally purified according to typical techniques. This removes from complementary strands (50) the enzymes, oligos, and other reagents used heretofore in the processing of the library. An exemplary purification step is the use of DNA bead purification reagent (e.g. Ampure XP DNA purification beads sold by Beckman-Coulter). Such solid phase reversible immobilization (SPRI) beads are functionalized with carboxyl-coatings and formulated in high salt (e.g. 1-2 M NaCl) solutions containing ~20% polyethylene glycol and buffering agents. DNA of a decreasing size range will bind to the beads with the addition of this DNA purification solution to DNA-containing solutions at ratios of 0.5 to 1, 1 to 1, 2 to 1 or 4 to 1, respectively. The bead with bound DNA can then be separated from the bulk solution with a magnet, washed with appropriate reagents, and the DNA eluted from the beads with a low salt solution (e.g. 10 mM Tris pH8.0 and 1 mM EDTA), thereby yielding purified DNA. In one illustrative embodiment, the bead solution is added to the products of linear amplification at a ratio of approximately 2 volumes of DNA purification solution to 1 volume of amplified DNA.

Specific Targeting with an Oligonucleotide Probe

Figure 1D:
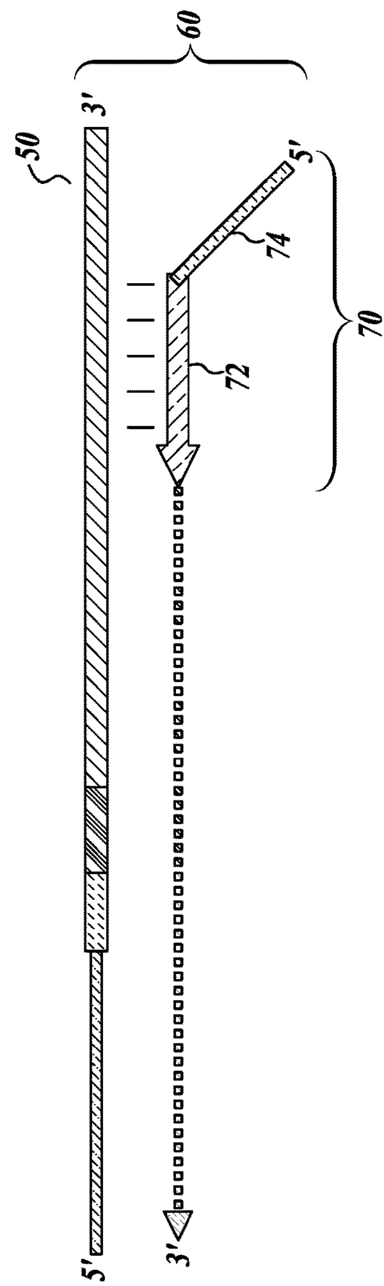
Figure 3B:
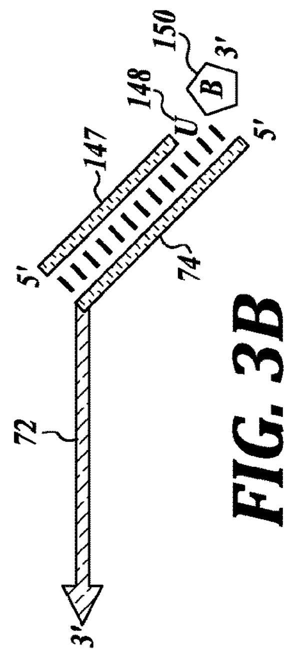
FIGS. 3A and 3B are cartoon illustrations of illustrative design features of −85 nucleotide oligonucleotide probes ("Fetcher oligonucleotide probes") according to one embodiment of this disclosure.
Figure 3A:
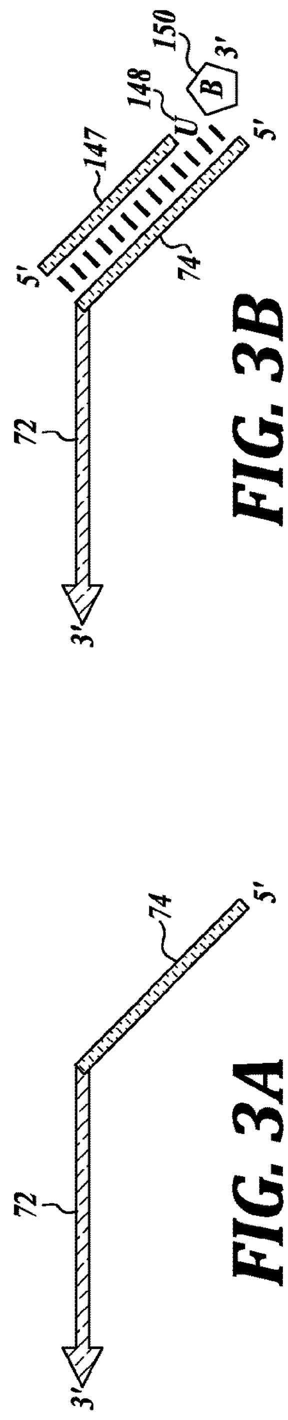

After sufficient quantities of complementary strand (50) of the adapter/fragment chimeric molecules are produced, specific target complementary strands are captured and isolated for further processing and sequencing. The specificity of the retrieval is conferred by an oligonucleotide probe (70; also referred to herein as a "Fetcher oligonucleotide"). As illustrated in FIGS. 1D, 3A, and 3B, the oligonucleotide probe (70) comprises a hybridization domain (72) with a sequence that hybridizes to a target sequence in the complementary strand (50) to produce a targeted complement strand/probe duplex (60). In some embodiments, the hybridization domain is ≥20 nt, ≥25 nt, ≥30 nt, ≥35 nt, ≥40 nt, ≥50 nt, ≥60 nt. In some embodiments, the hybridization domain (72) is about 25 to about 50 nt. In some embodiments, the hybridization domain is about 30-50 nt, such as about 30 nt, about 35 nt, about 40 nt, about 45 nt, about 50 nt, about 55 nt in length. The hybridization domain terminates at the 3' end of the oligonucleotide probe (70) to permit eventual extension of the probe along the complementary strand (50), which serves as the template.

It will be appreciated that the hybridization domain (72) can be designed and optimized based on the known upstream and or downstream sequences that are immediately adjacent to intended target sequences in the input dsDNA. The phrase "immediately adjacent" as applied here means a hybridization sequence that is within about 1-100 bases of the target sequence region, such as within about 1-50 bases, such as within about 1-20 bases, within about 1-10 bases, and within about 1-5 bases of the target sequence region. In a preferred embodiment, the hybridization domain (72) can be designed to hybridize next to, i.e., within 1 base, of the target sequence. In addition, these sequences should preferably target genomic segments that are found only once in the target genome. For example, there are many repetitive sequences in the human genome and oligonucleotide probes that retrieve such redundant sequences will capture a large number of unrelated sequence clones that are distributed throughout the genome. In rare instances it may be necessary to target sequences that are found two or more times in the human reference genome. These instances are more acceptable providing it is recognized that certain oligonucleotide probes will retrieve redundant genomic loci and this is accounted for in the analysis that follows DNA sequencing. It is often possible to disambiguate such data in the analysis process downstream of sequence generation.

The oligonucleotide probe (70) also comprises a primer annealing domain (74) with a nucleotide sequence that permits annealing of a primer and, hence, later PCR amplification under the correct reaction conditions (described below). The primer annealing domain (74) can typically comprise between about 15 and about 60 nucleotides, such as about 15 nt, about 20 nt, about, 25 nt, about 30 nt, about 35 nt, about 40 nt, about 45 nt, about 50 nt, about 55 nt, or about 60 nt.

In some embodiments, the oligonucleotide probe (70) comprises a complementary duplex oligonucleotide (147) annealed to the 5' end of the oligonucleotide probe (70). In some embodiments, the complementary duplex oligonucleotide (147) anneals to part or all of the primer annealing domain (74) of the oligonucleotide probe. See, e.g., FIG. 3B. In some embodiments, the complementary duplex oligonucleotide (147) can comprise a 3' terminal biotin moiety (150). In some embodiments, the complementary duplex oligonucleotide (147) can comprise at least one substitution of a T base with dideoxy U base (148). In some embodiments, the complementary duplex oligonucleotide (147) comprises both a 3' terminal biotin moiety (150) and a T base with dideoxy U base (148). The 3' terminal biotin moiety (150) permits optional capture and purification functionality with immobilized biotin binding partners (e.g., bead-bound avidin or streptavidin). The dideoxy U base (148) permits cleavage of the biotin moiety from the complementary duplex oligonucleotide (147) and release of the isolated duplex of complementary oligonucleotide (147), the oligonucleotide probe (70), and the complementary strand (50) (i.e., the targeted complement strand/probe duplex (60)). This is described in more detail below.

The disclosed method has been generally described heretofore in the context of processing a single input dsDNA (10), e.g., attaching a single oligonucleotide adapter (20), etc. However, it will be apparent to persons of ordinary skill in the art that the method is practically scaled up to process a plurality of input dsDNA molecules (10), e.g., from the same (or multiple) originating biological samples in a single sample batch or multiple sample batches in parallel. In a single sample batch, the plurality of oligonucleotide adapters will have the sample tag domain (26) sequence. In the processing of multiple batches, the initial step of attaching the oligonucleotide adapters (20) are performed in parallel such that each sample batch maintains its own unique sample tag domain (26) sequence. However, the resulting complementary strands (50) can be combined and contacted with the oligonucleotide probe (70). The oligonucleotide probes (70) can be identical (e.g., with identical hybridization domain (74) sequences that target the same sequence). Alternatively, a plurality of different oligonucleotide probes (70) can be contacted to a plurality of complementary strands (50) produced in step (b) in a single hybridization step (c), wherein the plurality of different oligonucleotide probes each comprises a hybridization domain (74) with a different sequence that hybridizes to a different target sequence. This is useful when a plurality of different double stranded DNA fragments exist in the input dsDNA sample (or if there are multiple initial sample batches) and multiple target sequences are being assayed in a multiplex analysis.

In some embodiments, the hybridization step (c) and/or purification step (d) (described in more detail below) is/are performed in an isostabilizing salt solution. For purposes of hybridizing the oligonucleotide probe (70) to the complementary strand (50) to form a stable targeted complement strand/oligonucleotide probe duplex (60), this isostabilizing salt solution adds flexibility to the design of the hybridization domain and choice of target sequences. In many targeted hybrid capture systems, it is important to account for an oligonucleotide design that balances melting temperature ("Tm") of the targeting probes as measured in standard hybridization buffers. The use of isostabilizing compounds in the DNA hybridization reaction alleviates this constraint and allows for hybridization domain sequences of uniform length that may have significantly different melting temperatures in conventional buffers. In the context of the present disclosure, an "isostabilizing compound" is a molecule that has been shown, when present at specific molarities in aqueous solutions, to shift the melting temperatures of genomic DNAs with widely varying G:C content to a uniform Tm. A non-limiting, exemplary isostabilizing salt solution comprises tetramethylammonium chloride. In some embodiments, the isostabilizing salt solution comprises about 2M to 4M (e.g., about 2.5M, about 3.0M, about 3.5M) tetramethylammonium chloride.

One key feature of isostabilizing compounds in the context of the present disclosure is that the melting temperature of DNA duplexes becomes dependent on the length of the duplexed sequence. To illustrate, and without being bound to any particular theory or explanation, this means that duplexes formed between the complementary strands (50) and oligonucleotides probe (70) in which 40 of 40 bases are perfectly base-paired will have a higher melting temperature than duplexes that are less than 40 bp in length. This length-based discrimination can be an important asset to the present disclosure because the human genome has 3 billion bp and spurious duplexes of less than 40 bp, and in particular those less than 30 bp, are likely to be common. This is especially true in cases where internal mismatches and gaps are tolerated within the targeted complement strand/oligonucleotide probe duplex (60), and these partial duplexes inevitably occur with significant frequency. This length-dependent-Tm feature that manifests in isostable compound solutions is particularly critical after the hybridization phase where the temperature of the annealing reaction can be raised briefly to a temperature near the Tm (meaning within 2° C. to 8° C.) of a perfect 40 mer duplex. This will melt apart the majority of unwanted duplexes that are less than 40 bp while preserving the majority of desired duplexes that are 40 bp.

The phrases "on-target" and "off-target" are often used in the context of targeted NGS. The aim during optimization of targeted hybrid capture methods is to maximize on-target reads and minimize off-target reads. "On-target" means that the DNA sequence of the retrieved genomic fragment maps within the intended genomic coordinates of the target sequence. In the case of the present disclosure, this means that the retrieved genomic sequence, determined by sequencing, maps to the 3' side of the oligonucleotides probe (70) and the 5' most base of the genomic sequence aligns to the genome within 300 nt, and more often within 125 nt of the DNA sequence of the cognate oligonucleotide probe (70). The goal of targeted sequencing technology is to optimize the number of on-target sequences. "Off-target" means that the retrieved genomic sequence maps to a location in the reference genome that is far-removed from the alignment sequence of the hybridization domain (72) sequence. For practical purposes, "far-removed" is any alignment >1000 nt away from the 3' end of the oligonucleotides probe (70) if the alignment is to the 3' side of oligonucleotides probe (70), any alignment that is to the 5' side of the oligonucleotides probe (70) regardless of its location relative to the hybridization domain (72) sequence, and any alignment that occurs on a different chromosome than that of the hybridization domain (72) sequence. The specificity of a targeted hybrid capture system is measured as the sum of on-target sequences divided by the sum of total sequences that can be aligned to the human genome that were retrieved. Note that the phrase "alignable" is often used as a shorthand designation to refer to "sequences that can be aligned to the human genome." The molar ratio of complementary strands (50) to oligonucleotides probe (70) can be an important consideration in the performance optimization of the presently disclosed methods. Oligonucleotides probes (70) can be added to template DNA solutions at a concentration between about 1 pM and 10 nM. In some embodiments, oligonucleotides probes (70) are added such that their final concentration is about 20 pM to about 80 pM, such as about 20 pM, about 25 pM, about 30 pM, about 35 pM, about 40 pM, about 45 pM, about 50 pM, about 55 pM, about 60 pM, about 65 pM, about 70 pM, about 70 pM, or 80 pM. In some embodiments, the oligonucleotides probes (70) are added at a concentration of about 67 pM.

In the context of the presently disclosed targeted-retrieval by oligonucleotides probes (70) and application of NGS, the use of isostabilizing compounds also increases "sensitivity" and "uniformity" of targeted sequence capture. "Sensitivity" is defined, for any given experiment, as the sum of the regions actually retrieved by a set of targeted oligonucleotide probe divided by the total sum of the targets covered (i.e. intended to be retrieved) by oligonucleotide probe. By way of example, it is common to encounter statements in the targeted hybrid capture literature claiming particular capture rates, indicating that DNA sequencing reads were found that correspond to a particular percent of the regions targeted by capture probes, and conversely that the remaining percentage of targeted regions failed to be captured and sequenced. Another critical metric used to evaluate targeted hybrid NGS methods is "uniformity." In the present context, uniformity is a measure of coverage depth, meaning the number of independent DNA sequences at each oligonucleotide probe hybridizing site relative to the overall average depth across all probes. Accordingly, "independent DNA sequence" are defined as having a unique set of genomic mapping coordinates and a unique clone label. Uniformity is calculated by first determining the mean number of independent reads that are on-target across the entire collection of oligonucleotide probes present in a given experiment. The ratio of independent reads at each oligonucleotide probe is then compared to the global average. The percentage of oligonucleotide probe sites with independent reads depths that are within a given "range" of the mean is then reported. A typical reporting range may be probes with read depths within 50% of the mean. Another method to convey uniformity is with a graphical display. See e.g. FIG. 7.

In summary, isostabilizing agents, such as 3M tetramethylammonium chloride solution, can be used during the hybridization of the oligonucleotide probe:complementary strand. The use of isostabilizing solutions relaxes the constraints on oligonucleotide probe designs by transforming all 40 mer sequences, regardless of A:T vs G:C base composition, into DNA molecules with the same melting temperatures. Additionally, the property that duplex stability becomes a simple function of length in isostable solutions can be used to increase the specificity of targeted hybrid capture after the hybridization reaction is complete. This can be accomplished by raising the temperature of the hybridized molecules to a temperature near the Tm of 40 mers for a period of approximately 5 min as described below for purification using the disclosed method. Taken together, these properties of isostabilizing compounds significantly contribute to the sensitivity and uniformity of target sequence retrieval.

Purifying the Targeted Complement Strand/Probe Duplex

After the oligonucleotide probe (70) anneals to the complementary strand (50) to form a targeted complement strand/probe duplex (60), the reaction mixture will also include unhybridized, off-target complementary strands and unhybridized oligonucleotide probes. The disclosure encompasses embodiments where additional steps are used to isolate the targeted complement strand/probe duplex (60) from the hybridizing reaction mix, significantly removing the un-annealed probes and complementary strands, as well as any other reaction components that remain. This is referred to as "purifying", although this is not intended to require complete and total isolation of the complement strand/probe duplex (60).

In some embodiments, the targeted complement strand/probe duplex (60) is purified by size selection. This can be effective to remove unhybridized oligonucleotide probes. Several DNA purification media (e.g. silica matrices, molecular sieves, carboxyl-coated magnetic beads suspended in high salt, polyethylene glycol solutions, and the like) can preferentially purify DNA based on size. See, e.g., Hawkins T. L., et al. Nucleic Acids Res. 1994 Oct. 25; 22(21):4543-40; Lundin S., et al. PLoS One. 2010 Apr. 6; 5(4); Borgstrom E., et al. PLoS One. 2011 Apr. 27; 6(4), each incorporated herein by reference in its entirety). In an illustrative, non-limiting example, the size selection is performed using DNA bead purification reagent, as described above. In the present non-limiting example, a ratio of 1.2 parts purification reagent is added to 1.0 part DNA solution. Other methods, particularly binding to silica beads using solutions that are adjusted for size-specific purification, can be equally effective.

In other embodiments, wherein the oligonucleotide probe comprises a complementary duplex oligonucleotide (147) with a 3' terminal biotin moiety (150) and one or more T bases substituted with dideoxy U bases (148), the purifying of the targeted complement strand/probe duplex comprises binding of the 3' terminal biotin moiety (150) of the oligonucleotide probe in the targeted complementary strand/probe duplex to a streptavidin-coated paramagnetic bead. The paramagnetic beads are then immobilized, e.g., with a magnet, and a wash can be applied. In some embodiments, a high stringency wash of the bead-bound targeted complement strand/probe duplex is applied to remove spurious or off-target annealing structure. A non-limiting, exemplary high stringency wash step can comprise incubating the bead bound targeted complement strand/probe duplexes in a solution comprising about 3M tetramethylammonium chloride at about 75° C. for about 5 min.

Paramagnetic beads are known to inhibit PCR amplification reactions and they must therefore be removed prior to PCR amplification of the sequencing template molecules. In the disclosed example, the covalent bond linking the target strand/probe duplex (60) to the biotin moiety is cleaved at the deoxyuracil bases by the combined action of uracil DNA glycosylase and an endonuclease specific for abasic residues. This enzyme combination is found in the commercial reagent sold as USER II enzyme mix by New England Biolabs. The purified target strand/probe duplexes are liberated from the beads by USER II cleavage, the beads are separated from the DNA-containing supernatant using a magnet, and the clarified supernatant is transferred to a fresh vessel for the sequence template generation steps disclosed below.

Generating Sequencing Template Molecules

Once the complement strand/probe duplex (60) is isolated from the hybridization reaction mixture at the desired stringency, the oligonucleotide probes hybridized to the complementary strands are extended from the 3' end of the hybridized probe to provide an extended template (80). See FIG. 1D. The extended template (80) is a chimeric DNA strand that possesses, as read in the 5' to 3' direction, the oligonucleotide probe tail sequence, the oligonucleotide probe, the genomic sequence from the targeted complementary strand corresponding to targeted sequence in the input dsDNA, the sample tag domain (24), the clone tag domain (26), and the oligonucleotide adapter's primer annealing domain (22).

Extension of the oligonucleotide probe is performed as an initial step in PCR amplification of extended template (80).

In some embodiments, extension of the probe in step (e) comprises applying a thermostable DNA polymerase at >about 55° C., >about 57° C., or >about 60° C. In some embodiments, the thermostable DNA polymerase is Taq DNA polymerase. In another illustrative, non-limiting embodiment, the extension step can be catalyzed by the thermostable DNA polymerase Q5 (New England Biolabs). Probe extension can comprise a typical PCR amplification mixture containing the thermostable enzyme, dNTPs and purified complement strand/probe duplex (60) in an appropriate buffer solution that is raised to about 72° C. (anywhere from 50° C. to 80° C.) for 30 or more seconds prior to PCR amplification.

Figure 1E:
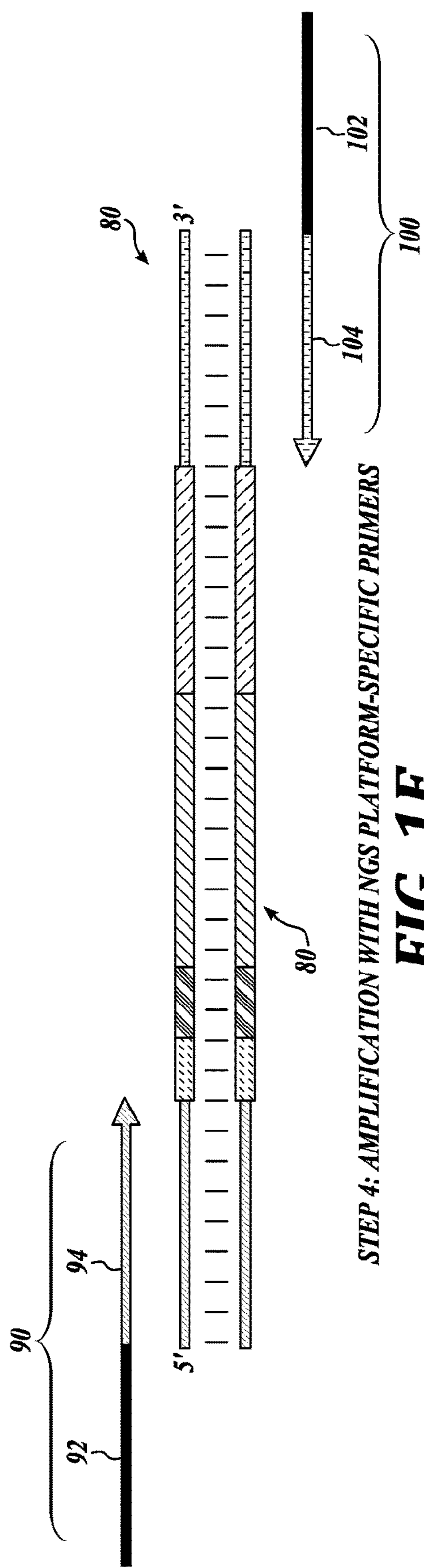

The amplifying in step (e) can be performed in the same or different reaction as the extending activity. The amplification step comprises using a forward PCR primer (90) that selectively anneals to a primer annealing domain in the targeted complement strand of the duplex and a reverse PCR primer (100) that selectively anneals to a primer annealing domain in the extended probe strand. See FIG. 1E. Each of the first and second PCR primers (90 and 100, respectively) comprises two domains: a template annealing domain (94 and 104, respectively) that anneals to the primer annealing domain integrated into the extended template (80), and a NGS-specific domain (92 and 102, respectively) that has sequences specific to the desired NGS platform used for subsequent sequencing. The presence of the NGS-specific domains (92 and 102) makes these PCR primers "tailed PCR primers". In some embodiments, the template annealing domains (94 and 104) are between 15 and 40 nt, such as about 20 nt, about 25 nt, or about 30 nt, with sequences complementary to primer annealing sequences specific to this disclosure at their 3' ends.

Figure 1F:
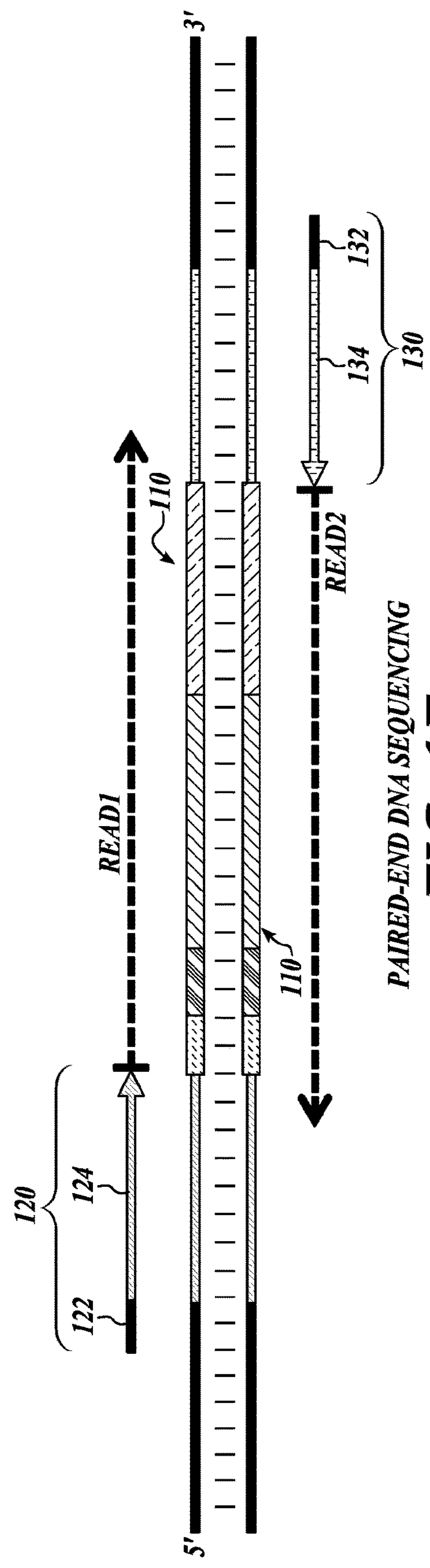

The number of PCR amplification cycles required to generate a measurable amount of amplified, sequencing-ready targeted clones (i.e., sequencing template molecules (110) in FIG. 1F) can depend strongly on the number of different oligonucleotide probes (70) included in the prior hybridization reaction. As a general guide, greater numbers of distinct oligonucleotide probes (70) will generate a greater number of extended templates (80) that will therefore require fewer PCR cycles to generate detectable and quantifiable amounts of sequencing template molecules (110). The PCR amplification in step (e) can be mediated by a high-fidelity thermostable polymerase. A non-limiting example is Q5 polymerase.

Following PCR amplification, the amplified sequencing template molecules (110) can be purified according to any appropriate technique known in the art to provide the sequencing library. For example, purification can be conducted by automatable bead-based methods identical to those described above. The purified material can be quantified using fluorescence methods such as the Qubit instrument and double-strand specific kits provided by Thermo Fisher (Waltham, Mass.).

In some embodiments, the method also comprises sequencing the template molecules (110). The library of sequencing template molecules (110) resulting from the above steps is amenable to sequencing by any desired NGS platform, so long as the first and second PCR primers appropriately consider the requirements for the particular NGS platform. In the Examples described below, the sequencing platform used for proof-of-principle/reduction-to-practice was an Illumina (San Diego, Calif.) MiSeq genome analysis instrument. Therefore, the NGS-specific domains (92 and 102) were specific to that platform. However, a similar strategy could be readily adapted to any number of existing or future NGS platforms, hence this specific example should not be considered as limiting.

In some embodiments, the method is performed for a plurality of double stranded DNA fragments resulting in a plurality of different sequencing molecules, and the DNA sequencing is performed on a massively parallel next-generation sequencing platform. By way of example, the Illumina MiSeq platform is amenable to paired-end sequencing where opposing reads from the same strand are generated (FIG. 1F). As described above, in some embodiments, the oligonucleotide adapter comprises a clone tag domain with a nucleotide sequence that labels each resulting genomic clone and a sample tag domain with a nucleic acid sequence that labels independent samples and thereby allows multiplex analysis of multiple samples at once. The method can further comprise applying bioinformatics analysis that integrates alignment coordinates of the obtained sequenced of the double-stranded DNA fragment, the sequence of the clone tag domain, and the sequence of the sample tag domain.

The present disclosure is configured to enable the identification and characterization of independent DNA clones. In the specific context of liquid biopsies performed on human subjects, the disclosed methods permit targeted sequencing of individual cfDNA fragments and post-NGS data analysis. As defined here, the terms "unique clone" or "unique fragment" or "unique read" or "unique molecule" or "unique sequence" all refer to a sequenced DNA fragment that is readily differentiable from all other DNA sequences obtained from a sample. Importantly, the same "unique fragment" may be sequenced several times since amplification upstream of DNA sequencing can produce identical molecules (clones) of the same fragment. When multiple sequences of the same unique fragment are present in an NGS dataset, each member of this "clonal family", meaning a set of sequences all corresponding to the same original cfDNA fragment, are grouped into a single consensus "unique clone/fragment/read/sequence". The ability to recognize unique fragments is facilitated by the labels that are affixed to the DNA (e.g., cfDNA) fragments first by adapter ligation and later by hybridization with oligonucleotide probes with primer extension. The sample label allows multiplexing of samples in NGS and parsing of sequences to specific samples in post-sequence analysis. The alignment coordinates of the retrieved DNA (e.g., cfDNA) sequence, the DNA sequence of the clone label and the identity of the oligonucleotide probe all contribute to the classification of a sequence as being either unique or a member of clonal family.

The ability to condense NGS data first into specific samples and then into unique reads within a sample is a fundamental aspect of the present disclosure for both sequencing-based identification of SNVs, indels or fusions and for counting-based detection of copy number changes in target regions. It is well known to those skilled in the art that NGS is error prone, and this creates a challenge in post-sequence analysis of differentiating between "machine noise", meaning sporadic and/or sometimes systematic errors intrinsic to the NGS platform, and rare mutations harbored within ctDNA fragments that may be encountered in the overall collection of cfDNA fragments and that are relevant to cancer. Several approaches for error correction of machine noise have been described. However, error correction techniques, such as Safe-SeqS and duplex sequencing, can add considerable expense because they require that each DNA fragment must be sequenced multiple times.

The present disclosure provides a different and less costly approach to error correction than either Safe-SeqS or duplex sequencing. Specifically, any candidate mutation must be encountered in several different, independent, unique clones to be considered a true mutation. Rather than relying on repetitive sequencing of the same initial DNA fragment from many replicated clones for identification of potential mutations, the disclosed approach relies on observing several (meaning greater than three or four) unique fragments, all of which have the same rare mutation. In this context, the methods that provide a high conversion rate of dsDNA fragments into analyzable clones disclosed here are required to reveal these multiple, independent mutant clones at a clinically useful sensitivity (e.g. <1.0% mutant allele frequency, preferably <0.1% mutant allele frequency). This is a different approach from the intensive analysis of each and every mutation embodied in the Safe-SeqS or duplex sequencing approaches that can only be supported by redundant sequencing. This approach is less costly than the Safe-SeqS or duplex sequencing approaches because it does not require that every fragment in a DNA sample be sequenced multiple times. Instead, the disclosed approach simply demands sufficient sequence coverage to produce a set of unique clones that all possess the same, potentially rare lesion(s). An example of variant calling by this approach is embodied in the genotyping data shown in Table 5.

As discussed above, one aspect of liquid biopsy technology is the detection of genetic lesions that are therapeutically actionable. In this context, liquid biopsies can provide the "diagnosis" that is required to direct therapeutic treatment options in the emerging practice of precision medicine. A second aspect of liquid biopsies, "monitoring" of ctDNA levels as a proxy for disease burden. One application of monitoring is surveillance for disease relapse for patients whose disease is in remission. A second application is early assessment of treatment efficacy. Recent scientific literature suggests that ctDNA levels decline in patients whose tumors are responding to therapy, suggesting that monitoring of ctDNA may be generally useful as a marker for treatment efficacy (Almodovar K. J Thorac Oncol. 2018 January; 13(1):112-123.; Merker JD. J Clin Oncol. 2018 Jun. 1; 36(16):1631-1641, each of which is incorporated herein by reference in its entirety). Monitoring applications leverage tumor-specific differences between the genome of the tumor vs the normal tissue. These tumor-specific mutations, or "tumor markers," may or may not be causal for the disease; their utility is that they can be used to differentiate tumor-derived ctDNA fragments from normal, germ-line DNA fragments. Importantly, monitoring applications of liquid biopsies imply quantitative analysis of the proportion of ctDNA fragments relative to germ-line fragments within a sample. This proportion is often referred to as the "minor allele frequency (MAF)" of "variant allele frequency (VAF)" of a tumor-specific mutation. The accurate determination of tumor marker MAF/VAF depends on the ability to count unique fragments, a point of emphasis in the present disclosure.

For the purposes of monitoring, certain genes are frequently mutated in almost all cancers, the most notable being the TP53, tumor suppressor gene. While there are no targeted therapies directed at cancers harboring TP53 mutations, it is nonetheless a useful tumor marker for monitoring of ctDNA levels. It is therefore anticipated that in the practice of the presently disclosed methods, TP53 will often be sequenced in its entirety. In addition, many specific cancer types harbor frequent mutations in genes that are particular to the subtype of cancer. The disclosed methods and compositions are intended to provide a generic tool for the targeted analysis of genomic DNA; it is "programmable" by virtue of the hybridization domain sequences of the oligonucleotide probes, which are used in the assay and to retrieve the desired corresponding genomic regions. When the application of this technology calls for disease monitoring of particular cancer subtypes, it is anticipated that oligonucleotide probe "panel," meaning the intended targets of the constellation of oligonucleotide probes used in a specific assay, will include probes to interrogate these disease-specific, frequently-mutated genes for the purposes of disease burden monitoring.

The presently disclosed methods and compositions are also designed to accommodate the detection of copy number variation among target genes. This is significant because it is understood by those skilled in the art that cancer can result from, and be driven by, amplification of oncogenes and loss of genes required for tumor suppression. Copy analysis relies on the counting of unique sequences that are retrieved by any particular oligonucleotide probe. In many cases the target region for the disclosed methods will be the coding regions of an entire gene, and in humans (multicellular eukaryotes in general) this often means sequencing multiple exons that are dispersed among intronic regions. Moreover, the requirement for sequencing both strands of a target gene implies that oligonucleotide probes can be chosen to anneal to both strands of a target exon and, by and large, at multiple positions within targeted regions. The genomic depth of a target gene or region can therefore be calculated from the aggregate profile of unique read counts (often termed as "coverage depth" or simply "coverage") for each oligonucleotide probe across a target region. In some instance, it may be desirable to augment accurate genomic depth analysis for target loci by including additional oligonucleotide probes that anneal to unique genomic regions (e.g. intronic segments) that are within or near the target region of interest. The motivation for these additional oligonucleotide probes is that counting has inherent statistical noise and additional data can therefore increase the precision of genomic counting measurements by increasing the signal-to-noise ratio. This disclosure is not intended to teach bioinformatics methods, yet aggregate counts at each target loci within a test sample can be compared to a similar profile generated from known control samples. In this way, intrinsic variation in target-to-target genomic depth measurements are removed by "normalization" to established reference standards.

Kits

In another aspect, the disclosure provides a kit comprising one or more reagents, as described above, and written indicia instructing the performance of the methods described above. The kit can comprise an oligonucleotide adapter, a DNA polymerase with 3' to 5' exonuclease activity capable of creating blunt ends on double-stranded DNA, a plurality of enzymes that mediate DNA repair, a DNA ligation enzyme, and written indicia instructing the performance of the method as described above.

In some embodiments, the kit further comprises an alkaline phosphatase.

In some embodiments, the kit comprises T4 DNA polymerase, the Klenow fragment of *E. coli* DNA polymerase I, or a combination thereof. In some embodiments, the kit comprises full-length Bst DNA polymerase, Taq DNA ligase, Endonuclease IV, or any combination thereof. In some embodiments, the kit further comprises a buffer configured to support dephosphorylation and/or DNA repair. In some embodiments, the kit comprises T4 DNA ligase, T3 DNA ligase, or a combination thereof. In some embodiments, the kit comprises comprising ligation buffer.

The oligonucleotide adapter of the kit can contain the elements of the oligonucleotide adapter as described above. For example, in some embodiments the oligonucleotide adapter comprises a primer annealing domain with a nucleotide sequence that permits linear or exponential PCR amplification upon annealing of a primer. In some embodiments, the oligonucleotide adapter comprises a clone tag domain and/or a sample tag domain.

In some embodiments, the kit further comprises a first primer that anneals to the annealing domain of the oligonucleotide adapter.

In some embodiments, the kit further comprises nucleotide triphosphates that support both DNA repair, DNA polymerization and/or DNA ligation. In some embodiments, the nucleotide triphosphates comprise dNTPs and ATP.

In some embodiments, the kit further comprises an oligonucleotide probe, as described above. In some embodiments, the oligonucleotide probe comprises a hybridization domain with a sequence that hybridizes to a target genomic sequence. The hybridization domain can be ≥20 nt, ≥25 nt, ≥30 nt, ≥35 nt, or ≥40 nt. The oligonucleotide probe can comprise a primer annealing domain with a nucleotide sequence that permits PCR amplification upon annealing of a primer. In some embodiments, the oligonucleotide probe comprises a complementary duplex oligonucleotide annealed to the 5' end of the oligonucleotide probe. The complementary duplex oligonucleotide can comprise a 3' terminal biotin moiety and at least one substitution of a T base with dideoxy U base.

In some embodiments, the kit further comprises Taq polymerase and/or Q5 polymerase.

In some embodiments, the kit further comprises magnetic beads configured to bind to nucleic acid molecules. In some embodiments, the magnetic beads can be carboxyl-coated beads. In some embodiments, the magnetic beads can be streptavidin-coated beads. In some embodiments, the kit comprises both carboxyl-coated beads and streptavidin-coated beads.

In some embodiments, the kit further comprises an iso-stabilizing salt, or solution thereof. In some embodiments, the kit further comprises a high-stringency wash solution.

In some embodiments, the kit further comprises PCR primers, as described above. In some embodiments, the kit further comprises platform specific sequencing primers, as described above.

General Definitions

Unless specifically defined herein, all terms used herein have the same meaning as they would to one skilled in the art of the present disclosure. Practitioners are particularly directed to Ausubel, F. M., et al. (eds.), *Current Protocols in Molecular Biology*, John Wiley & Sons, New York (2010), incorporated herein by reference in their entireties.

For convenience, certain terms employed herein, in the specification, examples and appended claims are provided here. The definitions are provided to aid in describing particular embodiments and are not intended to limit the claimed invention, because the scope of the invention is limited only by the claims.

The use of the term "or" in the claims is used to mean "and/or" unless explicitly indicated to refer to alternatives only or the alternatives are mutually exclusive, although the disclosure supports a definition that refers to only alternatives and "and/or."

The words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense, which is to indicate, in the sense of "including, but not limited to." Words using the singular or plural number also include the plural and singular number, respectively. The word "about" indicates a number within range of minor variation above or below the stated reference number. For example, "about" can refer to a number within a range of 10%, 9%, 8%, 7%, 6%, 5%, 4%, 3%, 2%, or 1% above or below the indicated reference number.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are provided for the purpose of illustrating, not limiting, the disclosure.

Example 1

This example describes an exemplary embodiment of attachment of multifunctional oligonucleotide adapter ("LINDA") adapters to repaired and polished cfDNA.

Cell-free DNA (cfDNA) was purified from the plasma of healthy donors using the QIAamp Circulating Nucleic Acid Kit as described by the manufacturer (Qiagen, Hilden, Germany). The yields of double-strand DNA were quantified using a Qubit fluorometer (ThermoFisher, Waltham, Mass.) and reagents for quantitation of double-strand DNA (Biotium, Fremont, Calif.). The plasma samples used in these examples provided 10-15 ng/mL of plasma. Forty microliter aliquots of cfDNA with a concentration of 1.14 ng/ul were dephosphorylated using recombinant shrimp alkaline phosphatase (New England Biolabs, Ipswich, Mass.) at 37° C. for 30 min, followed by DNA repair and blunt end creation (polishing) with an enzyme cocktail containing T4 DNA polymerase, full-length Bst DNA polymerase, Taq DNA ligase and Endonuclease IV (NEB) in a 50 ul reaction containing 100 nM of each dNTP at 20° C. for 5 min. The repaired and polished DNA was added to a 100 ul ligation reaction containing 1×DNA ligation buffer (NEB), 2 uM LINDA adapters (FIG. 2B, TABLE 1), and 10 ul of DNA ligase. All of the oligonucleotides used in these experiments were synthesized by Integrated DNA Technologies (Coralville, Iowa). Following an incubation at 20° C. for 60 min, the ligated DNA was purified with SPRI DNA purification beads using two rounds at a ratio of 0.85 volume of beads-to-1.0 volume of DNA. The ligation products were eluted in 42 ul of TE buffer.

TABLE 1

DNA sequences of LINDA ligation (lig) and partner (part) oligonucleotides

| Name | Sequence[1,2,3] | SEQ ID NO: |
|---|---|---|
| LINDA lig_1 | 5'Phos/CTCATGGAGA | 1 |
| LINDA lig_2 | 5'Phos/AGATGCCTCT | 2 |

TABLE 1-continued

DNA sequences of LINDA ligation (lig) and partner (part) oligonucleotides

| Name | Sequence[1,2,3] | SEQ ID NO: |
|---|---|---|
| LINDA lig_3 | 5'Phos/TCTGCAAGAG | 3 |
| LINDA lig_4 | 5'Phos/GAGCATTCTC | 4 |
| LINDA lig_5 | 5'Phos/GATAACTCGT | 5 |
| LINDA lig_6 | 5'Phos/CTGTTAGACG | 6 |
| LINDA lig_7 | 5'Phos/AGCGGTCTAC | 7 |
| LINDA lig_8 | 5'Phos/TCACCGAGTA | 8 |
| LINDA lig_9 | 5'Phos/ACCATTGGTC | 9 |
| LINDA lig_10 | 5'Phos/CAATGGCCGA | 10 |
| LINDA lig_11 | 5'Phos/GTTGCCAACT | 11 |
| LINDA lig_12 | 5'Phos/TGGCAATTAG | 12 |
| LINDA lig_13 | 5'Phos/ACTCAAGCTG | 13 |
| LINDA lig_14 | 5'Phos/CAGATTCAGC | 14 |
| LINDA lig_15 | 5'Phos/GTCTGGATCA | 15 |
| LINDA lig_16 | 5'Phos/TGAGCCTGAT | 16 |
| LINDA_iSp C3_part_1 | CAAC/iSpC3/TCCCTACACGACG CTCTTCCGATCTNNNNNNNNTCTC CATGA*G/3SpC3/ | 17 |
| LINDA_iSp C3_part_2 | CAAC/iSpC3/TCCCTACACGACG CTCTTCCGATCTNNNNNNNNAGAG GCATC*T/3SpC3/ | 18 |
| LINDA_iSp C3_part_3 | CAAC/iSpC3/TCCCTACACGACG CTCTTCCGATCTNNNNNNNNCTCT TGCAG*A/3SpC3/ | 19 |
| LINDA_iSp C3_part_4 | CAAC/iSpC3/TCCCTACACGACG CTCTTCCGATCTNNNNNNNNGAGA ATGCT*C/3SpC3/ | 20 |
| LINDA_iSp C3_part_5 | CAAC/iSpC3/TCCCTACACGACG CTCTTCCGATCTNNNNNNNNACGA GTTAT*C/3SpC3/ | 21 |
| LINDA_iSp C3_part_6 | CAAC/iSpC3/TCCCTACACGACG CTCTTCCGATCTNNNNNNNNCGTC TAACA*G/3SpC3/ | 22 |
| LINDA_iSp C3_part_7 | CAAC/iSpC3/TCCCTACACGACG CTCTTCCGATCTVGTAGACCGC* T/3SpC3/ | 23 |
| LINDA_iSp C3_part_8 | CAAC/iSpC3/TCCCTACACGACG CTCTTCCGATCTNNNNNNNNTACT CGGTG*A/3SpC3/ | 24 |
| LINDA_iSp C3_part_9 | CAAC/iSpC3/TCCCTACACGACG CTCTTCCGATCTNNNNNNNNGACC AATGG*T/3SpC3/ | 25 |
| LINDA_iSp C3_part_10 | CAAC/iSpC3/TCCCTACACGACG CTCTTCCGATCTNNNNNNNNTCGG CCATT*G/3SpC3/ | 26 |
| LINDA_iSp C3_part_11 | CAAC/iSpC3/TCCCTACACGACG CTCTTCCGATCTNNNNNNNNAGTT GGCAA*C/3SpC3/ | 27 |
| LINDA_iSp C3_part_12 | CAAC/iSpC3/TCCCTACACGACG CTCTTCCGATCTNNNNNNNNCTAA TTGCC*A/3SpC3/ | 28 |
| LINDA_iSp C3_part_13 | CAAC/iSpC3/TCCCTACACGACG CTCTTCCGATCTNNNNNNNNCAGC TTGAG*T/3SpC3/ | 29 |
| LINDA_iSp C3_part_14 | CAAC/iSpC3/TCCCTACACGACG CTCTTCCGATCTNNNNNNNNGCTG AATCT*G/3SpC3/ | 30 |
| LINDA_iSp C3_part_15 | CAAC/iSpC3/TCCCTACACGACG CTCTTCCGATCTNNNNNNNNTGAT CCAGA*C/3SpC3/ | 31 |
| LINDA_iSp C3_part_16 | CAAC/iSpC3/TCCCTACACGACG CTCTTCCGATCTNNNNNNNNATCA GGCTC*A/3SpC3/ | 32 |

[1]"5'Phos/" indicates a 5' phosphate

[2]"iSpC3" indicates an internal spacer structure with three contiguous methyl groups (3' ribose-CH2-CH2-CH2-5' phosphate) that serves as a very flexible tether to link the sequences on either side. The "3SpC3 indicates a 3' end spacer with a similar structure but having a 5' hydroxyl instead of a phosphate (i.e., 3' ribose-CH2-CH2-CH2-5' phosphate).

[3]"*"indicates the presence of a phosphorothioate rather than a normal phosphate in the backbone linking the nucleotides on either side in the sequence. In this structure, one of the two oxygens in the phosphate are replaced with a sulfur.

The ligation efficiency was monitored using qPCR with primers (5'-3') AATGATACGGCGACCACCGAGATCTA-CACTCTTTCCCTACACGACGCTCTTCCGA TCT (SEQ ID NO:33) and GAGGCTGAGGCAGGAGAATCG (SEQ ID NO:34). The first qPCR primer anneals to the LINDA adapter sequence and the latter primer anneals to a region of the human Alu SINE element. The amount of ligated cfDNA in the unknown sample was calculated by running a set of calibration samples of known concentration and interpolation of samples using this standard curve. Typical library yield measurements were 6-8 ng of ligated LINDA/cfDNA for cfDNA inputs of 25-40 ng. Given that one human genome has an approximate mass of 3.3 pg, this translates into a range of genomic depth of 1800 to 2400 cloned genomes.

The metrics for the experiment included in this report are set forth in TABLE 2.

TABLE 2 metrics for attachment of the LINDA adapter.

| | Sample | | | |
|---|---|---|---|---|
| | 1 | 2 | 3 | 4 |
| Library tags | L1-L4 | L5-L8 | L9-L12 | L13-L16 |
| Input DNA [ng] | 45.6 | 45.6 | 45.6 | 45.6 |
| Library yield | 8.0 | 7.5 | 7.7 | 6.2 |
| Est. genomic depth | 2439 | 2262 | 2325 | 1880 |

Example 2

This example describes the linear amplification of LINDA adapter/cfDNA fragment chimeric templates.

The 40 ul samples of library from EXAMPLE 1 were amplified in a 100 ul reaction containing 50 ul of NEB-Next® Ultra™ II Q5® Master Mix, and 10 ul of 4 uM primer (5'-3') AATGATACGGCGACCACCGAGATCTA-CACTCTTTCCCTACACGACGCTCTTCCGA TCT (SEQ ID NO:35) using a thermal cycling program of 98° C. for 30 sec and 20 cycles of a 2-step amplification of 98° C. for 10 sec and 65° C. for 60 sec. The amplified product was purified with solid phase reversible immobilization (SPRI) DNA purification magnetic beads at a ratio of 2.0 volume of beads-to-1.0 volume of amplified DNA. See, e.g., Rohland N, Reich D., Cost-effective, high-throughput DNA sequencing libraries for multiplexed target capture. Genome Research 22: 939-946, incorporated herein by reference in its entirety. The purified single-stranded DNA was eluted in a volume of 10 ul of TE buffer (10 mM Tris pH8.0, 1 mM EDTA).

The single-stranded DNA generated by this linear method was quantified using qPCR of unique loci in the human genome. Two primer pair assays monitor regions in the human EGFR gene (EGFR-4: GTCGCAGAGCACTTGCA-GACTTTTT (SEQ ID NO:36)+AATGTGGTTTCGTTG-GAAGCAAATG (SEQ ID NO:37) and EGFR-5: TTCTGCTTAACCATTGTGGGCATCT (SEQ ID NO:38) CAATCAAGATGGTTTTGCCAAGGAA (SEQ ID NO:39)) and two pairs monitor unique regions in the TP53 gene (TP53-2: CGTATCCCCCTGCATTTCTTTTGTT (SEQ ID NO:40)+CAAAGGGTGAAGAGGAATCC-CAAAG (SEQ ID NO:41) and TP53-3: TTTATCCATCC-CATCACACCCTCAG (SEQ ID NO:42) AAAGAAAAGTTCTGCATCCCCAGGA (SEQ ID NO:43)). Relative to the unamplified input material, all four assays revealed a 10-to-15-fold increase in the amount of these unique genomic regions. The actual values for the experiment reported in this example are set forth in TABLE 3.

TABLE 3 metrics for attachment of the LINDA adapter.

| | Sample | | | |
|---|---|---|---|---|
| | 1 | 2 | 3 | 4 |
| Fold increase for EGFR-4 | 14 | 14 | 15 | 15 |
| Fold increase for EGFR-5 | 14 | 13 | 12 | 14 |
| Fold increase for TP53-2 | 13 | 12 | 10 | 11 |
| Fold increase for TP53-3 | 15 | 11 | 10 | 11 |

Example 3

This Example describes an exemplary embodiment of hybridizing complementary strand of the adapter/fragment chimeric molecule produced in EXAMPLE 2 with oligonucleotide probes ("Fetcher oligonucleotides") and post-hybridization processing into an NGS sequencing library A set of four amplified cfDNA libraries were pooled to a final volume of 40 ul and then split into two separate hybridization reactions labeled "A" and "B". Each hybridization reaction contained 20 ul of DNA and 4 ul of "A" or "B" pooled Fetcher oligonucleotides (oligonucleotide probes; see FIG. 3B and TABLE 4). The "A" pool contained 64 different Fetcher sequences and the "B" pool contained 63 different Fetcher sequences. Each individual Fetcher oligonucleotide was present at 50 pM final concentration in the hybridization reaction. The blend of DNA and Fetcher oligonucleotide was denatured at 98° C. for 2 min and 36 ul of hybridization buffer containing 5M tetramethylammonium chloride, 10 mM Tris pH8.0, 1 mM EDTA and 0.1% Tween-20 was added. These hybridization reactions were then heated to 98° C. for 10 sec and incubated at 65° C. for 4 hours.

TABLE 4

DNA sequences of Fetcher oligonucleotides.

| Fetcher oligonucleotide name | Sequence | SEQ ID NO: |
|---|---|---|
| Ex_2_F1 | ATACGAGATGTGACTGGAGTTCAGACGTGTGCTCTTCCGATCTCCC AGGGTTGGAAGTGTCTCATGCTGGATCCCCACTTTTC | 44 |
| Ex_2_F3 | ATACGAGATGTGACTGGAGTTCAGACGTGTGCTCTTCCGATCTGAG GAGCCGCAGTCAGATCCTAGCGTCGAGCCCCCTCTGA | 45 |
| Ex_2_R2 | ATACGAGATGTGACTGGAGTTCAGACGTGTGCTCTTCCGATCTTCC ACTCACAGTTTCCATAGGTCTGAAAATGTTTCCTGAC | 46 |
| Ex_3_F1 | ATACGAGATGTGACTGGAGTTCAGACGTGTGCTCTTCCGATCTGAA AATTCCATGGGACTGACTTTCTGCTCTTGTCTTTCAG | 47 |
| Ex_4_F1 | ATACGAGATGTGACTGGAGTTCAGACGTGTGCTCTTCCGATCTGGC TGGGGGGCTGGGGGGCTGAGGACCTGGTCCTCTGACT | 48 |
| Ex_4_F3 | ATACGAGATGTGACTGGAGTTCAGACGTGTGCTCTTCCGATCTCAA TGGATGATTTGATGCTGTCCCCGGACGATATTGAACA | 49 |
| Ex_4_F5 | ATACGAGATGTGACTGGAGTTCAGACGTGTGCTCTTCCGATCTATG CCAGAGGCTGCTCCCCCCGTGGCCCCTGCACCAGCAG | 50 |
| Ex_4_F7 | ATACGAGATGTGACTGGAGTTCAGACGTGTGCTCTTCCGATCTCCT GTCATCTTCTGTCCCTTCCCAGAAAACCTACCAGGGC | 51 |

TABLE 4-continued

DNA sequences of Fetcher oligonucleotides.

| Fetcher oligonucleotide name | Sequence | SEQ ID NO: |
|---|---|---|
| Ex_4_R1 | ATACGAGATGTGACTGGAGTTCAGACGTGTGCTCTTCCGATCTGCA GGGGGATACGGCCAGGCATTGAAGTCTCATGGAAGCC | 52 |
| Ex_4_R3 | ATACGAGATGTGACTGGAGTTCAGACGTGTGCTCTTCCGATCTCTG TCCCAGAATGCAAGAAGCCCAGACGGAAACCGTAGCT | 53 |
| Ex_4_R5 | ATACGAGATGTGACTGGAGTTCAGACGTGTGCTCTTCCGATCTGGC CAGGAGGGGGCTGGTGCAGGGGCCGCCGGTGTAGGAG | 54 |
| Ex_4_R7 | ATACGAGATGTGACTGGAGTTCAGACGTGTGCTCTTCCGATCTTCT GGGAGCTTCATCTGGACCTGGGTCTTCAGTGAACCAT | 55 |
| Ex_5_F1 | ATACGAGATGTGACTGGAGTTCAGACGTGTGCTCTTCCGATCTTTC ACTTGTGCCCTGACTTTCAACTCTGTCTCCTTCCTCT | 56 |
| Ex_5_F3 | ATACGAGATGTGACTGGAGTTCAGACGTGTGCTCTTCCGATCTACT GGCCAAGACCTGCCCTGTGCAGCTGTGGGTTGATTCC | 57 |
| Ex_5_F5 | ATACGAGATGTGACTGGAGTTCAGACGTGTGCTCTTCCGATCTACA AGCAGTCACAGCACATGACGGAGGTTGTGAGGCGCTG | 58 |
| Ex_5_R2 | ATACGAGATGTGACTGGAGTTCAGACGTGTGCTCTTCCGATCTCTG CTCACCATCGCTATCTGAGCAGCGCTCATGGTGGGGG | 59 |
| Ex_5_R4 | ATACGAGATGTGACTGGAGTTCAGACGTGTGCTCTTCCGATCTAGA TGGCCATGGCGCGGACGCGGGTGCCGGGCGGGGGTGT | 60 |
| Ex_6_F1 | ATACGAGATGTGACTGGAGTTCAGACGTGTGCTCTTCCGATCTAGA GACGACAGGGCTGGTTGCCCAGGGTCCCCAGGCCTCT | 61 |
| Ex_6_F3 | ATACGAGATGTGACTGGAGTTCAGACGTGTGCTCTTCCGATCTCAT CTTATCCGAGTGGAAGGAAATTTGCGTGTGGAGTATT | 62 |
| Ex_6_R1 | ATACGAGATGTGACTGGAGTTCAGACGTGTGCTCTTCCGATCTCCT GGAGGGCCACTGACAACCACCCTTAACCCCTCCTCCC | 63 |
| Ex_6_R3 | ATACGAGATGTGACTGGAGTTCAGACGTGTGCTCTTCCGATCTGGC ACCACCACACTATGTCGAAAAGTGTTTCTGTCATCCA | 64 |
| Ex_7_F1 | ATACGAGATGTGACTGGAGTTCAGACGTGTGCTCTTCCGATCTCCC CTGCTTGCCACAGGTCTCCCCAAGGCGCACTGGCCTC | 65 |
| Ex_7_F3 | ATACGAGATGTGACTGGAGTTCAGACGTGTGCTCTTCCGATCTACC ACCATCCACTACAACTACATGTGTAACAGTTCCTGCA | 66 |
| Ex_7_R1 | ATACGAGATGTGACTGGAGTTCAGACGTGTGCTCTTCCGATCTGGT CAGAGGCAAGCAGAGGCTGGGGCACAGCAGGCCAGTG | 67 |
| Ex_7_R3 | ATACGAGATGTGACTGGAGTTCAGACGTGTGCTCTTCCGATCTGTG ATGATGGTGAGGATGGGCCTCCGGTTCATGCCGCCCA | 68 |
| Ex_8_F1 | ATACGAGATGTGACTGGAGTTCAGACGTGTGCTCTTCCGATCTTAG GACCTGATTTCCTTACTGCCTCTTGCTTCTCTTTTCC | 69 |
| Ex_8_F3 | ATACGAGATGTGACTGGAGTTCAGACGTGTGCTCTTCCGATCTGAG GTGCGTGTTTGTGCCTGTCCTGGGAGAGACCGGCGCA | 70 |
| Ex_8_R1 | ATACGAGATGTGACTGGAGTTCAGACGTGTGCTCTTCCGATCTGCA TAACTGCACCCTTGGTCTCCTCCACCGCTTCTTGTCC | 71 |
| Ex_8_R3 | ATACGAGATGTGACTGGAGTTCAGACGTGTGCTCTTCCGATCTTGG TGAGGCTCCCCTTTCTTGCGGAGATTCTCTTCCTCTG | 72 |
| Ex_9_F1 | ATACGAGATGTGACTGGAGTTCAGACGTGTGCTCTTCCGATCTGAG ACCAAGGGTGCAGTTATGCCTCAGATTCACTTTTATC | 73 |
| Ex_9_F3 | ATACGAGATGTGACTGGAGTTCAGACGTGTGCTCTTCCGATCTAGC TCCTCTCCCCAGCCAAAGAAGAAACCACTGGATGGAG | 74 |
| Ex_9_R2 | ATACGAGATGTGACTGGAGTTCAGACGTGTGCTCTTCCGATCTTAA GAGGTCCCAAGACTTAGTACCTGAAGGGTGAAATATT | 75 |

TABLE 4-continued

DNA sequences of Fetcher oligonucleotides.

| Fetcher oligonucleotide name | Sequence | SEQ ID NO: |
|---|---|---|
| Ex_10_F1 | ATACGAGATGTGACTGGAGTTCAGACGTGTGCTCTTCCGATCTCTTGAACCATCTTTTAACTCAGGTACTGTGTATATACTTA | 76 |
| Ex_10_F3 | ATACGAGATGTGACTGGAGTTCAGACGTGTGCTCTTCCGATCTGCGCTTCGAGATGTTCCGAGAGCTGAATGAGGCCTTGGAA | 77 |
| Ex_10_R1 | ATACGAGATGTGACTGGAGTTCAGACGTGTGCTCTTCCGATCTGAATCCTATGGCTTTCCAACCTAGGAAGGCAGGGGAGTAG | 78 |
| Ex_10_R3 | ATACGAGATGTGACTGGAGTTCAGACGTGTGCTCTTCCGATCTTGCTCCCCCCTGGCTCCTTCCCAGCCTGGGCATCCTTGAG | 79 |
| Ex_11_F1 | ATACGAGATGTGACTGGAGTTCAGACGTGTGCTCTTCCGATCTGGCACAGACCCTCTCACTCATGTGATGTCATCTCTCCTCC | 80 |
| Ex_11_F3 | ATACGAGATGTGACTGGAGTTCAGACGTGTGCTCTTCCGATCTTCAGTCTACCTCCCGCCATAAAAAACTCATGTTCAAGACA | 81 |
| Ex_11_R2 | ATACGAGATGTGACTGGAGTTCAGACGTGTGCTCTTCCGATCTGAACAAGAAGTGGAGAATGTCAGTCTGAGTCAGGCCCTTC | 82 |
| rs2909430_F | ATACGAGATGTGACTGGAGTTCAGACGTGTGCTCTTCCGATCTCAAGTGAACAGATAAAGCAACTGGAAGACGGCAGCAAAGA | 83 |
| rs1050541_F | ATACGAGATGTGACTGGAGTTCAGACGTGTGCTCTTCCGATCTTCTGTAGCTGTAGAGGCATTTTAACCCTTTGTCCTCCAGC | 84 |
| rs1794289_F | ATACGAGATGTGACTGGAGTTCAGACGTGTGCTCTTCCGATCTCCTCCCTGTCTCACGCCATGGTAGCGTCCGCCTAGGTTGC | 85 |
| rs2287499_F | ATACGAGATGTGACTGGAGTTCAGACGTGTGCTCTTCCGATCTCCCGGTTGTCCCCAGATCCTGTGGCTGGCTCAGCTGTGTC | 86 |
| rs2078486_F | ATACGAGATGTGACTGGAGTTCAGACGTGTGCTCTTCCGATCTTCACTTGTTCTATATTATTATTCTAGAGAGAACTGTGTGA | 87 |
| rs1614984_F | ATACGAGATGTGACTGGAGTTCAGACGTGTGCTCTTCCGATCTTTTAAATCCCGTAATCCTTGGTGAGAGGCTGCCGAGGGGG | 88 |
| KDM6A_ex17_F1 | ATACGAGATGTGACTGGAGTTCAGACGTGTGCTCTTCCGATCTGCTAAGTTGCAGGTACTTTTTGATAACTTTAGGACTTGGG | 89 |
| KDM6A_ex17_F3 | ATACGAGATGTGACTGGAGTTCAGACGTGTGCTCTTCCGATCTCTCCAGGCAGCTGGCTCTGGTATTCAGAATCAGAACGGAC | 90 |
| KDM6A_ex17_F5 | ATACGAGATGTGACTGGAGTTCAGACGTGTGCTCTTCCGATCTAATCATGTCCATCAGATGACGGCAGATGCTGTTTGCAGTC | 91 |
| KDM6A_ex17_F7 | ATACGAGATGTGACTGGAGTTCAGACGTGTGCTCTTCCGATCTTCTCCAAAATCCACTGAGCAGACAACCACAAACAGTGTTA | 92 |
| KDM6A_ex17_F9 | ATACGAGATGTGACTGGAGTTCAGACGTGTGCTCTTCCGATCTAAGTGAAAATGTTTGACTTACTGGCATGATCAGAATGCTG | 93 |
| KDM6A_ex17_R1 | ATACGAGATGTGACTGGAGTTCAGACGTGTGCTCTTCCGATCTAATAAAGCTTCTGTCAAACTCTTAGATGAATGACTACACC | 94 |
| KDM6A_ex17_R3 | ATACGAGATGTGACTGGAGTTCAGACGTGTGCTCTTCCGATCTTGTTTTCATGGGGCTCTGAGATTCTTCCATCCCTTCTCCA | 95 |
| KDM6A_ex17_R5 | ATACGAGATGTGACTGGAGTTCAGACGTGTGCTCTTCCGATCTGGCTTTTCCCATCAACAAGGCAGAGAGCTGAGGATTGTCT | 96 |
| KDM6A_ex17_R7 | ATACGAGATGTGACTGGAGTTCAGACGTGTGCTCTTCCGATCTTCCACCTGAGGTAGCAGTGTGAGAGGAGAGGTGATTGAGA | 97 |
| KDM6A_ex17_R9 | ATACGAGATGTGACTGGAGTTCAGACGTGTGCTCTTCCGATCTAAACTCAGAATATACAGAATTTAAAATATTAAAGAGAAAA | 98 |
| ILMN_SRY_F1 | ATACGAGATGTGACTGGAGTTCAGACGTGTGCTCTTCCGATCTAGTGTGTGGCTTTCGTACAGTCATCCCTGTACAACCTGTT | 99 |
| ILMN_SRY_F2 | ATACGAGATGTGACTGGAGTTCAGACGTGTGCTCTTCCGATCTGCATGGCCTGTAATTTCTGTGCCTCCTGGAAGAATGGCCA | 100 |

TABLE 4-continued

DNA sequences of Fetcher oligonucleotides.

| Fetcher oligonucleotide name | Sequence | SEQ ID NO: |
|---|---|---|
| rs307627_f | ATACGAGATGTGACTGGAGTTCAGACGTGTGCTCTTCCGATCTTCC TCATGGTCTTTTGGTTATATCTCATTTGTTCCTTCCT | 101 |
| rs839721_f | ATACGAGATGTGACTGGAGTTCAGACGTGTGCTCTTCCGATCTCTG GCTGAGAACAGGGCAGTGAAAGGGAACTGGGTGACAA | 102 |
| rs1105813_f | ATACGAGATGTGACTGGAGTTCAGACGTGTGCTCTTCCGATCTCAC GGAAGGGTCAGGGGCAAGGACTCCATGTGATGGGTAC | 103 |
| rs8522_f | ATACGAGATGTGACTGGAGTTCAGACGTGTGCTCTTCCGATCTCGG GAGCTGCAGTTCCCCACCCCCTCCATCTTGCTGCTTG | 104 |
| rs_16957022_f | ATACGAGATGTGACTGGAGTTCAGACGTGTGCTCTTCCGATCTAAA ACAGATGAAAAGCAAGATACTTCTAGCTGGCCAGCCA | 105 |
| rs11078710_f | ATACGAGATGTGACTGGAGTTCAGACGTGTGCTCTTCCGATCTAAC CATTAGTCCCTGAGAAGGTGGCAGGGGTGAGACTAAG | 106 |
| rs11078716_f | ATACGAGATGTGACTGGAGTTCAGACGTGTGCTCTTCCGATCTTAA GGCTGGCTTCCTAAACTTCATTCTCCCCAAACTGCTT | 107 |
| Ex_2_F2 | ATACGAGATGTGACTGGAGTTCAGACGTGTGCTCTTCCGATCTCTC TTGCAGCAGCCAGACTGCCTTCCGGGTCACTGCCATG | 108 |
| Ex_2_R1 | ATACGAGATGTGACTGGAGTTCAGACGTGTGCTCTTCCGATCTGGG GTTGGGGTGGGGGTGGTGGGCCTGCCCTTCCAATGGA | 109 |
| Ex_2_R3 | ATACGAGATGTGACTGGAGTTCAGACGTGTGCTCTTCCGATCTTCA GAGGGGGCTCGACGCTAGGATCTGACTGCGGCTCCTC | 110 |
| Ex_4_F2 | ATACGAGATGTGACTGGAGTTCAGACGTGTGCTCTTCCGATCTGCT CTTTTCACCCATCTACAGTCCCCCTTGCCGTCCCAAG | 111 |
| Ex_4_F4 | ATACGAGATGTGACTGGAGTTCAGACGTGTGCTCTTCCGATCTATG GTTCACTGAAGACCCAGGTCCAGATGAAGCTCCCAGA | 112 |
| Ex_4_F6 | ATACGAGATGTGACTGGAGTTCAGACGTGTGCTCTTCCGATCTCTC CTACACCGGCGGCCCCTGCACCAGCCCCCTCCTGGCC | 113 |
| Ex_4_F8 | ATACGAGATGTGACTGGAGTTCAGACGTGTGCTCTTCCGATCTAGC TACGGTTTCCGTCTGGGCTTCTTGCATTCTGGGACAG | 114 |
| Ex_4_R2 | ATACGAGATGTGACTGGAGTTCAGACGTGTGCTCTTCCGATCTAGC CCCTCAGGGCAACTGACCGTGCAAGTCACAGACTTGG | 115 |
| Ex_4_R4 | ATACGAGATGTGACTGGAGTTCAGACGTGTGCTCTTCCGATCTGCC CTGGTAGGTTTTCTGGGAAGGGACAGAAGATGACAGG | 116 |
| Ex_4_R6 | ATACGAGATGTGACTGGAGTTCAGACGTGTGCTCTTCCGATCTCTG CTGGTGCAGGGGCCACGGGGGGAGCAGCCTCTGGCAT | 117 |
| Ex_4_R8 | ATACGAGATGTGACTGGAGTTCAGACGTGTGCTCTTCCGATCTTGT TCAATATCGTCCGGGGACAGCATCAAATCATCCATTG | 118 |
| Ex_5_F2 | ATACGAGATGTGACTGGAGTTCAGACGTGTGCTCTTCCGATCTTCC TACAGTACTCCCCTGCCCTCAACAAGATGTTTTGCCA | 119 |
| Ex_5_F4 | ATACGAGATGTGACTGGAGTTCAGACGTGTGCTCTTCCGATCTACA CCCCCGCCCGGCACCCGCGTCCGCGCCATGGCCATCT | 120 |
| Ex_5_R1 | ATACGAGATGTGACTGGAGTTCAGACGTGTGCTCTTCCGATCTGGA CCCTGGGCAACCAGCCCTGTCGTCTCTCCAGCCCCAG | 121 |
| Ex_5_R3 | ATACGAGATGTGACTGGAGTTCAGACGTGTGCTCTTCCGATCTCAG CGCCTCACAACCTCCGTCATGTGCTGTGACTGCTTGT | 122 |
| Ex_5_R5 | ATACGAGATGTGACTGGAGTTCAGACGTGTGCTCTTCCGATCTGGA ATCAACCCACAGCTGCACAGGGCAGGTCTTGGCCAGT | 123 |
| Ex_6_F2 | ATACGAGATGTGACTGGAGTTCAGACGTGTGCTCTTCCGATCTGAT TCCTCACTGATTGCTCTTAGGTCTGGCCCCTCCTCAG | 124 |

TABLE 4-continued

DNA sequences of Fetcher oligonucleotides.

| Fetcher oligonucle otide name | Sequence | SEQ ID NO: |
|---|---|---|
| Ex_6_F4 | ATACGAGATGTGACTGGAGTTCAGACGTGTGCTCTTCCGATCTTGG ATGACAGAAACACTTTTCGACATAGTGTGGTGGTGCC | 125 |
| Ex_6_R2 | ATACGAGATGTGACTGGAGTTCAGACGTGTGCTCTTCCGATCTAGA GACCCCAGTTGCAAACCAGACCTCAGGCGGCTCATAG | 126 |
| Ex_6_R4 | ATACGAGATGTGACTGGAGTTCAGACGTGTGCTCTTCCGATCTAAT ACTCCACACGCAAATTTCCTTCCACTCGGATAAGATG | 127 |
| Ex_7_F2 | ATACGAGATGTGACTGGAGTTCAGACGTGTGCTCTTCCGATCTATC TTGGGCCTGTGTTATCTCCTAGGTTGGCTCTGACTGT | 128 |
| Ex_7_F4 | ATACGAGATGTGACTGGAGTTCAGACGTGTGCTCTTCCGATCTTGG GCGGCATGAACCGGAGGCCCATCCTCACCATCATCAC | 129 |
| Ex_7_R2 | ATACGAGATGTGACTGGAGTTCAGACGTGTGCTCTTCCGATCTTGC AGGGTGGCAAGTGGCTCCTGACCTGGAGTCTTCCAGT | 130 |
| Ex_7_R4 | ATACGAGATGTGACTGGAGTTCAGACGTGTGCTCTTCCGATCTTGC AGGAACTGTTACACATGTAGTTGTAGTGGATGGTGGT | 131 |
| Ex_8_F2 | ATACGAGATGTGACTGGAGTTCAGACGTGTGCTCTTCCGATCTTAT CCTGAGTAGTGGTAATCTACTGGGACGGAACAGCTTT | 132 |
| Ex_8_R2 | ATACGAGATGTGACTGGAGTTCAGACGTGTGCTCTTCCGATCTTGC TTGCTTACCTCGCTTAGTGCTCCCTGGGGGCAGCTCG | 133 |
| Ex_8_R4 | ATACGAGATGTGACTGGAGTTCAGACGTGTGCTCTTCCGATCTTGC GCCGGTCTCTCCCAGGACAGGCACAAACACGCACCTC | 134 |
| Ex_9_F2 | ATACGAGATGTGACTGGAGTTCAGACGTGTGCTCTTCCGATCTACC TTTCCTTGCCTCTTTCCTAGCACTGCCCAACAACACC | 135 |
| Ex_9_R1 | ATACGAGATGTGACTGGAGTTCAGACGTGTGCTCTTCCGATCTAAC GGCATTTTGAGTGTTAGACTGGAAACTTTCCACTTGA | 136 |
| Ex_9_R3 | ATACGAGATGTGACTGGAGTTCAGACGTGTGCTCTTCCGATCTCTC CATCCAGTGGTTTCTTCTTTGGCTGGGGAGAGGAGCT | 137 |
| Ex_10_F2 | ATACGAGATGTGACTGGAGTTCAGACGTGTGCTCTTCCGATCTCTT CTCCCCCTCCTCTGTTGCTGCAGATCCGTGGGCGTGA | 138 |
| Ex_10_F4 | ATACGAGATGTGACTGGAGTTCAGACGTGTGCTCTTCCGATCTCTC AAGGATGCCCAGGCTGGGAAGGAGCCAGGGGGGAGCA | 139 |
| Ex_10_R2 | ATACGAGATGTGACTGGAGTTCAGACGTGTGCTCTTCCGATCTGGC CAGGAAGGGGCTGAGGTCACTCACCTGGAGTGAGCCC | 140 |
| Ex_10_R4 | ATACGAGATGTGACTGGAGTTCAGACGTGTGCTCTTCCGATCTTTC CAAGGCCTCATTCAGCTCTCGGAACATCTCGAAGCGC | 141 |
| Ex_11_F2 | ATACGAGATGTGACTGGAGTTCAGACGTGTGCTCTTCCGATCTCTG CTTCTGTCTCCTACAGCCACCTGAAGTCCAAAAAGGG | 142 |
| Ex_11_R1 | ATACGAGATGTGACTGGAGTTCAGACGTGTGCTCTTCCGATCTGCA GGGGAGGGAGAGATGGGGGTGGGAGGCTGTCAGTGGG | 143 |
| Ex_11_R3 | ATACGAGATGTGACTGGAGTTCAGACGTGTGCTCTTCCGATCTTGT CTTGAACATGAGTTTTTTATGGCGGGAGGTAGACTGA | 144 |
| rs2909430_R | ATACGAGATGTGACTGGAGTTCAGACGTGTGCTCTTCCGATCTTAG ACGCCAACTCTCTCTAGCTCGCTAGTGGGTTGCAGGA | 145 |
| rs1050541_R | ATACGAGATGTGACTGGAGTTCAGACGTGTGCTCTTCCGATCTGGA GGCTGCAGCATTAAAAAAAGAAAAAGGAGGTTAGAGA | 146 |
| rs1794289_R | ATACGAGATGTGACTGGAGTTCAGACGTGTGCTCTTCCGATCTTGA TGCAAACCTCAATCCCTCCCCTTCTTTGAATGGTGTG | 147 |
| rs2287499_R | ATACGAGATGTGACTGGAGTTCAGACGTGTGCTCTTCCGATCTCCA AACTCTGTTTCCAGGGGAGTGGAGAGAGAAACTGGGT | 148 |
| rs2078486_R | ATACGAGATGTGACTGGAGTTCAGACGTGTGCTCTTCCGATCTGAG GTGTACTTGCATTAATGGAGTGGGGGTGGGAGCAGTA | 149 |

TABLE 4-continued

DNA sequences of Fetcher oligonucleotides.

| Fetcher oligonucleotide name | Sequence | SEQ ID NO: |
|---|---|---|
| rs1614984_R | ATACGAGATGTGACTGGAGTTCAGACGTGTGCTCTTCCGATCTCCT CCGGCCACGGCTGGCACAAGGTTCTCTCCCTCCCCTG | 150 |
| KDM6A_ex17_F2 | ATACGAGATGTGACTGGAGTTCAGACGTGTGCTCTTCCGATCTGCT TAATATTAGATTTAAACTATTTTTCTTTCTTTTTAGG | 151 |
| KDM6A_ex17_F4 | ATACGAGATGTGACTGGAGTTCAGACGTGTGCTCTTCCGATCTCAA CAAGGCATTACCTTAACCAAAGAGAGCAAGCCTTCAG | 152 |
| KDM6A_ex17_F6 | ATACGAGATGTGACTGGAGTTCAGACGTGTGCTCTTCCGATCTAAT AACAATGTGGGTACTGGAACCTGTGACAAAGTCAATA | 153 |
| KDM6A_ex17_F8 | ATACGAGATGTGACTGGAGTTCAGACGTGTGCTCTTCCGATCTGAT CTGCTTCTGGTTAACCACAAACCTAGTCCACAGATCA | 154 |
| KDM6A_ex17_F10 | ATACGAGATGTGACTGGAGTTCAGACGTGTGCTCTTCCGATCTTTG CTTAGATGTTGTAGTCAAATCAGATGTGAGAAGTATT | 155 |
| KDM6A_ex17_R2 | ATACGAGATGTGACTGGAGTTCAGACGTGTGCTCTTCCGATCTTGA TGAACTTTCCCACACTAACCTGCATGCCTTCAGAACT | 156 |
| KDM6A_ex17_R4 | ATACGAGATGTGACTGGAGTTCAGACGTGTGCTCTTCCGATCTAGG TGTTGCTGTTGAAATGGCTGAAGATGGTGAAGAGGCA | 157 |
| KDM6A_ex17_R6 | ATACGAGATGTGACTGGAGTTCAGACGTGTGCTCTTCCGATCTAGG AAGTCCCTCGACACTGGCAGTGCTGTTAGGTGTCTCT | 158 |
| KDM6A_ex17_R8 | ATACGAGATGTGACTGGAGTTCAGACGTGTGCTCTTCCGATCTATG CTGGGAAGGCCCAGTGGAAGAGAGAGGTCGTTCACCA | 159 |
| KDM6A_ex17_R10 | ATACGAGATGTGACTGGAGTTCAGACGTGTGCTCTTCCGATCTTAA TCAGTATTTAACATCTTTAGAGAAATTTTTCTTCCTT | 160 |
| ILMN_SRY_R1 | ATACGAGATGTGACTGGAGTTCAGACGTGTGCTCTTCCGATCTCAA TGCAATCATATGCTTCTGCTATGTTAAGCGTATTCAA | 161 |
| ILMN_SRY_R2 | ATACGAGATGTGACTGGAGTTCAGACGTGTGCTCTTCCGATCTAGG ATAGAGTGAAGCGACCCATGAACGCATTCATCGTGTG | 162 |
| rs307627_r | ATACGAGATGTGACTGGAGTTCAGACGTGTGCTCTTCCGATCTGCC ACACCCACTCTGACTCCCATAAAACCCAGCGGCTCTG | 163 |
| rs839721_r | ATACGAGATGTGACTGGAGTTCAGACGTGTGCTCTTCCGATCTGTC TAGATTTTTCTAGATTTTGTGTCTGTTTTCTCCAGTT | 164 |
| rs11656201_r | ATACGAGATGTGACTGGAGTTCAGACGTGTGCTCTTCCGATCTAGA AAGACAAACACCGCATGATCGCACTCATATGTCATAT | 165 |
| rs1105813_r | ATACGAGATGTGACTGGAGTTCAGACGTGTGCTCTTCCGATCTAGG GCTGGCTCTCTGACTGTGTCCTCTTCTTACCTGTCCC | 166 |
| rs8522_r | ATACGAGATGTGACTGGAGTTCAGACGTGTGCTCTTCCGATCTCAA ATGGCCGGAGCTGGACCGACCATGCTGCTACGAGAAG | 167 |
| rs16957022_r | ATACGAGATGTGACTGGAGTTCAGACGTGTGCTCTTCCGATCTGCT GTAGATCTTCTTCGATTGACCACTGTGATGGAAACTG | 168 |
| rs11078710_r | ATACGAGATGTGACTGGAGTTCAGACGTGTGCTCTTCCGATCTAGA TTATCATATGAGAACTCCCTTGAAATTCCAATACTCA | 169 |
| rs11078716_r | ATACGAGATGTGACTGGAGTTCAGACGTGTGCTCTTCCGATCTTGC TGGGGCCATCACGATGTGTGGGTGTCCAGGCCTCCGG | 170 |
| Tail complement | AGATCGGAAGAGCACACGTCTGAACTCCAGTCACAUCTCGU AT/3BioTEG[1] | 171 |

[1]The "3BioTEG" indicates a 3' terminal end biotin moiety

Following hybridization, the targeted complementary strand/Fetcher probe duplexes were purified using SPRI DNA purification beads (see above) at a ratio of 1.2 volume of beads-to-1.0 volume of DNA. The purified DNA was eluted in 10 ul of TE, the "A" and "B" hybs were pooled to 20 ul and combined with 20 ul of MyOne Streptavidin C1 Dynabeads (Thermofisher) in a final 40 ul solution containing 2M NaCl, 10 mM Tris pH 8.0, 1 mM EDTA and incubated at room temp for 15 min. The DNA bound to these paramagnetic beads was separated from the solution using a laboratory magnet, washed once with 200 ul of TE buffer containing 0.5% Tween 20, and resuspended in 40 ul of TE. Sixty microliters of hybridization buffer were added and the solution was heated to 75° C. for 5 min. The beads were separated, washed with 200 ul of TE buffer, and resuspended in 50 ul of uracil cleavage/primer extension buffer that contained OneTaq$^{HOT\ START}$ polymerase and User II cleavage enzyme (both from NEB) in 1× Taq buffer with 200 nM dNTPs. Cleavage was performed at 37° C. for 15 min. The beads were separated from the solution and discarded. Primer extension was performed by incubating the solution at 60° C. for 30 sec, 68° C. for 30 sec and 98° C. for 30 sec.

Figure 4:
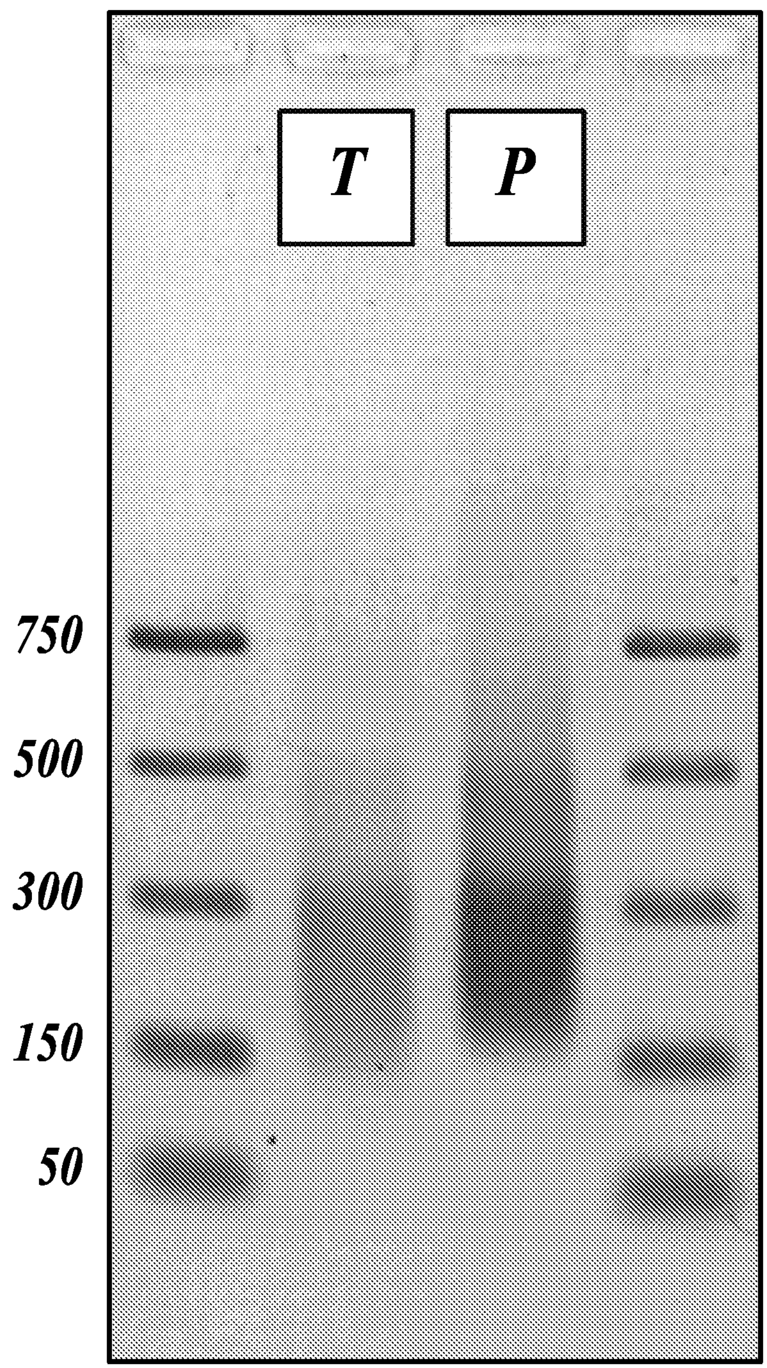
FIG. 4 shows a 2% agarose DNA gel of the total (T) and purified (P) sequencing library fractions described in EXAMPLE 3. The size in bp of the flanking molecular weight markers are indicated on the left.

The 50 ul cleaved and primer-extended capture DNA was carried forward into a 250 ul PCR amplification mix containing NEBNext® Ultra™ II Q5® Master Mix and Illumina sequencing platform-specific PCR primers AATGATACGGCGACCACCGAGATCTACACTCTTTCCCTACA (SEQ ID NO:172) and CAAGCAGAAGACGGCATACGAGATGTGACTGGAGTTCAGACGTG (SEQ ID NO:173). Twenty-five ul of the amplification blend was monitored by qPCR (98° C. —10 sec and 65° C. —60 sec) to determine the last cycle in which exponential amplification was observed; this proved to be cycle number 23 in all of the experiments reported here. The remaining 225 ul were amplified using a conventional thermal cycler for 23 cycles of PCR. Twenty-five microliters were purified as the "total library fraction" with 2.0 volumes of beads-to-1.0 volume of DNA sample and resuspended in a final volume of 20 ul. The remaining 200 ul were purified with SPRI DNA purification beads using three rounds at a ratio of 0.80 volume of beads-to-1.0 volume of DNA. The purified sequencing library was resuspended in a 40 ul volume of TE. Prior to sequencing, the amount of amplified and purified post-hybridization library was measured using the Qubit fluorometer and the size distributions of the total and purified fractions was determined using DNA gel electrophoresis (FIG. 4). For the experiment reported here, the yield from the total fraction was 12.7 ng/ul and the yield from the purified fraction was 43.4 ng/ul. When adjusted for volumes, this corresponds to an 85% recovery of DNA in the purified fraction.

Example 4

This example describes an exemplary embodiment of DNA sequencing and post-sequence analysis of the sequencing template molecules in the NGS sequencing library produced in EXAMPLES 1-3.

The set of four initial libraries that were labelled with different sample tags and pooled were sequenced using the MySeq genomic analysis instrument and a V2 300 cycle micro sequencing kit (Illumina, San Diego, Calif.). A dilution at a final concentration of 8 pM=1.3 pg/ul was loaded on the instrument, as recommended by the manufacturer. This conversion from molarity to mass-per-ul assumes an average total clone size of 250 bp; the observed yield of 798 clusters/mm$^2$ was in good agreement with the recommended density of 800 clusters/mm$^2$. Sequencing was performed in paired end mode with a 151 bp forward READ1 and a 151 bp reverse READ2. A portion of the resulting FASTQ file output was loaded into Excel (Microsoft, Redmond, Wash.) and analyzed.

Figure 5:
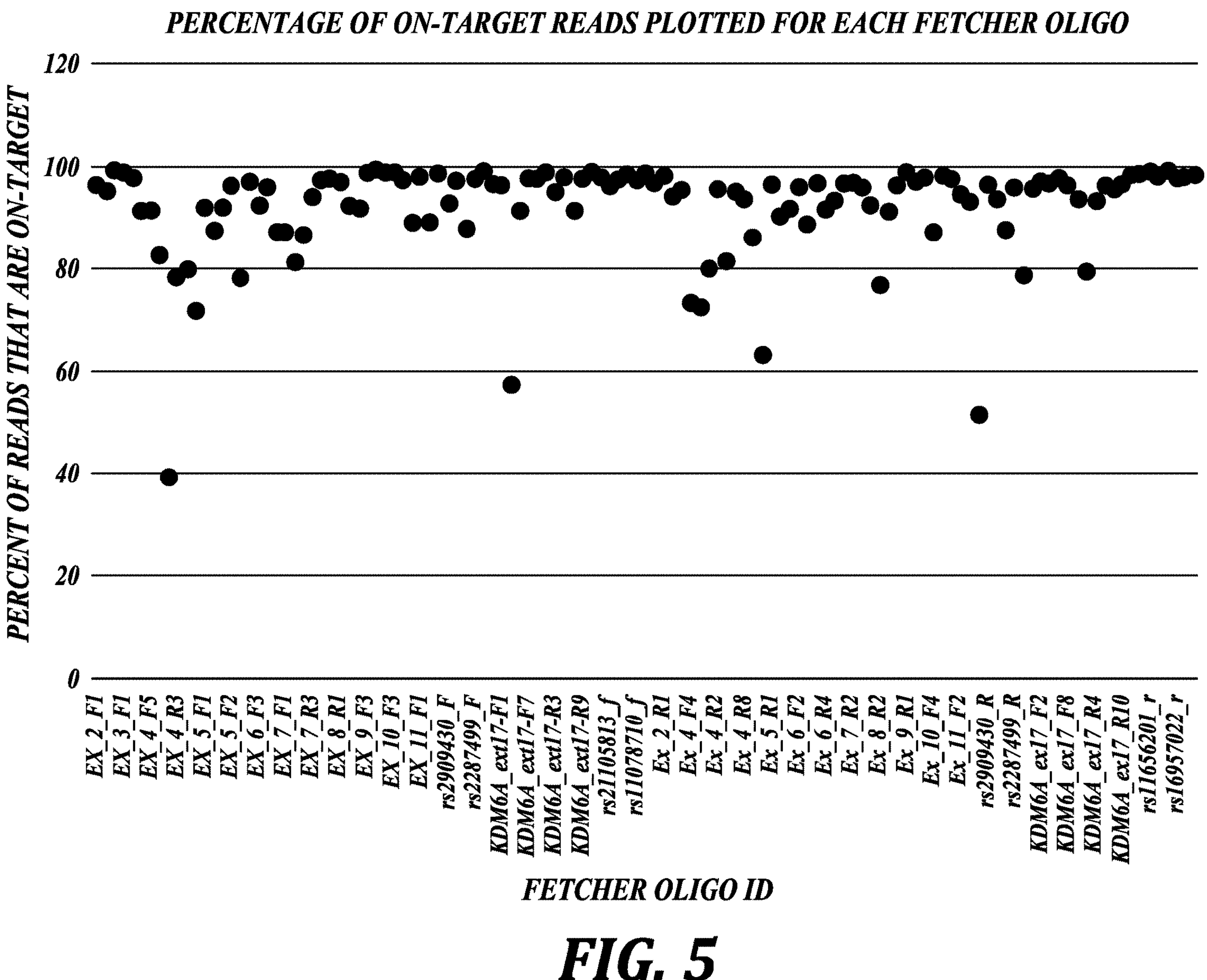
FIG. 5 graphically illustrates the percent of on-target reads for all 127 oligonucleotide probe ("Fetcher") oligonucleotides used in the proof-of-principle experiments.

DNA sequence analysis was used to extract important metrics from the data. These were:

- 92.8% of READ1 sequences had a match to the input sample tags at the correct position within the sequence. This represents a high yield of analyzable data.
- 84.2% of READ2 sequences had a match to one of the 127 possible Fetcher sequences.
- 79.9% of read pairs had a perfect match to a sample tag and a Fetcher sequence in READ1 and READ2, respectively.
- 91.0% of read pairs with a complete Fetcher sequence were "on-target", meaning that the first five bases of the captured sequence matched the expected target genomic sequence. A graph of the on-target rates for each independent Fetcher oligonucleotide is shown in FIG. 5.

Figure 6:
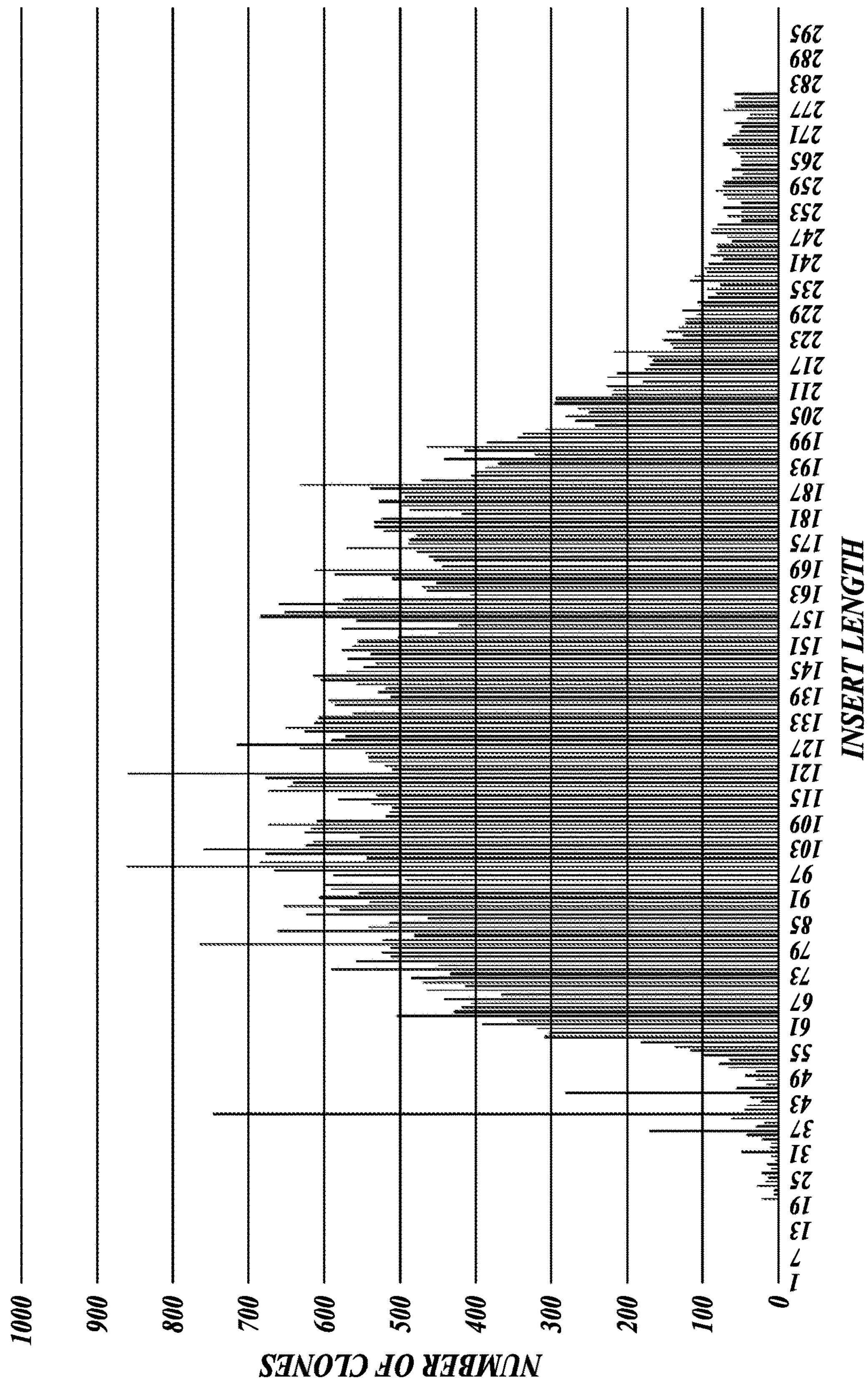
FIG. 6 graphically illustrates the insert size distribution profile for targeted cfDNA sequenced clones.

The distribution of insert sizes in the clone library, shown in FIG. 6, closely mirrors the expectation that the majority of inserts should range from 60 bp to 220 bp.

Figure 7:
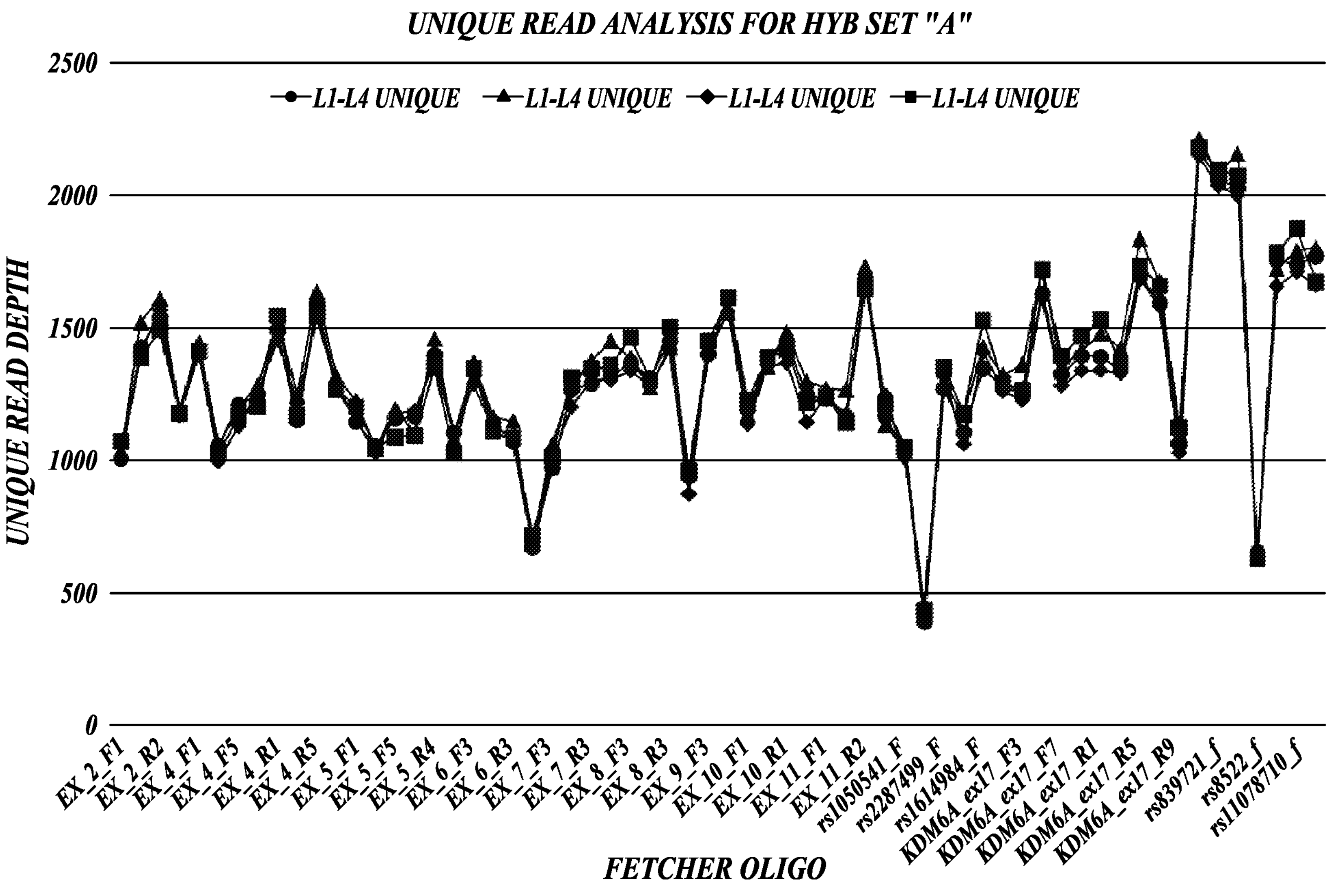
FIG. 7 shows the number of unique reads observed for each of the 62 oligonucleotide probes ("Fetcher") oligonucleotides in hyb pool "A". The SRY probe data is not shown for this female sample.

Measurements of the genomic depth of each library, defined as the number of unique genomic fragments encountered for each Fetcher oligonucleotide, are shown for hyb pool "A" across four independent libraries in FIG. 7. The average depth across all libraries and all pool "A" Fetcher positions was 1327 unique genomes. Note that the observed depth from qPCR measurements reported in EXAMPLE 1 and the maximum quantified depth from DNA sequence analysis are in good agreement. While there is variation in the number of unique reads (depth) for different Fetcher oligonucleotides, there is excellent reproducibility between libraries. This latter characteristic is important for measurement of copy number variation.

Many of the Fetcher oligonucleotides used in these experiments targeted human single-nucleotide polymorphisms (SNPs) that commonly vary between different individuals. An additional set of Fetcher oligonucleotides target the SRY gene found on the male-specific Y-chromosome, and a positive or negative signal from these targeted regions can be used to determine if gender is male or female, respectively. The genotyping data from cfDNA libraries of several individuals is shown in TABLE 5.

| | cfDNA ID# (HOM = homozygous; HET = heterozygous) | | | | | | | | | | SNP sequences |
|---|---|---|---|---|---|---|---|---|---|---|---|
| dbSNP ID | 19234 | 19268 | 19954 | 19337 | 19700 | 19117 | 19530 | 19970 | 19165 | 19755 | (SEQ ID NO) |
| rs1042522 (TP53) | HOM | | HOM | HOM | | HET | HOM | HOM | HET | HOM | AGGGGCCACGCGGGGAGCAGC (174) |
| | | HOM | | | HOM | HET | | | HET | | AGGGGCCACGGGGGGAGCAGC (175) |

-continued

| | cfDNA ID# (HOM = homozygous; HET = heterozygous) | | | | | | | | | | SNP sequences |
|---|---|---|---|---|---|---|---|---|---|---|---|
| dbSNP ID | 19234 | 19268 | 19954 | 19337 | 19700 | 19117 | 19530 | 19970 | 19165 | 19755 | (SEQ ID NO) |
| rs2230018 (KDM6A) | HOM | HET | | HOM | HET | | | HOM | HOM | HOM | AACATATTGACGGTGCCTGAA (176) |
| | | HET | HOM | | HET | HOM | HOM | | | | AACATATTGAAGGTGCCTGAA (177) |
| rs2909430 | HOM | HOM | HOM | HOM | HOM | HOM | HOM | HOM | HOM | HOM | AGGTGCTTACACATGTTTGTT (178) |
| | | | | | | | | | | | AGGTGCTTACGCATGTTTGTT (179) |
| rs1050541 | HOM | HET | | HET | | HET | HET | | | | ATCCCTTCACTTCCTCATCCT (180) |
| | | HET | HOM | HET | HOM | HET | HET | HOM | HOM | HOM | ATCCCTTCACGTCCTCATCCT (181) |
| rs2287499 (WRAP1) | HOM | | HOM | HOM | | HET | HOM | HOM | HOM | HET | TCCCCCTCCCGTAGCTCCTGG (182) |
| | | HOM | | | HOM | HET | | | | HET | TCCCCCTCCCCTAGCTCCTGG (183) |
| rs2078486 | HOM | HET | HOM | HOM | HET | HET | HOM | HOM | HOM | HOM | TTGTTAGTGCGGATCTGTGGT (184) |
| | | HET | | | HET | HET | | | | | TTGTTAGTGCAGATCTGTGGT (185) |
| rs1614984 | HOM | | HET | HOM | | HOM | HOM | HET | | HET | GCTTCTAGGACTGGGCTGCTT (186) |
| | | HOM | HET | | HOM | | | HET | HOM | HET | GCTTCTAGGATTGGGCTGCTT (187) |
| rs1800899 | HOM | HOM | HOM | HOM | HET | HOM | HOM | HOM | HOM | HOM | TACTAAGTCTTGGGACCTCTT (188) |
| | | | | | HET | | | | | | TACTAAGTCTCGGGACCTCTT (189) |
| rs1642785 | HOM | | HOM | HOM | | HET | HOM | HOM | HET | HOM | GGGTTGGGGTCGGGGTGGTGG (190) |
| | | HOM | | | HOM | HET | | | HET | | GGGTTGGGGTGGGGGTGGTGG (191) |
| rs12947788 | HOM | | HOM | HOM | HET | HET | HOM | HOM | HOM | HOM | TAAGAGGTGGGCCCAGGGGTC (192) |
| | | HOM | | | HET | HET | | | | | TAAGAGGTGGACCCAGGGGTC (193) |
| rs307627 | | | | HOM | | HOM | | | | HET | CCAGTTTTACTCCAATCTCCT (194) |
| | HOM | HOM | HOM | | HOM | | HOM | HOM | HOM | HET | CCAGTTTTACCCCAATCTCCT (195) |
| rs839721 | HET | HET | | HOM | HET | HOM | HET | HET | HOM | HET | CAGTTGATCCGACAGCAACAG (196) |
| | HET | HET | HOM | | HET | | HET | HET | | HET | CAGTTGATCCAACAGCAACAG (197) |
| rs11656201 | HET | HET | | HOM | HET | HOM | | | | | GTAACCAGCACTCGACTCTGC (198) |
| | HET | HET | HOM | | HET | | HOM | HOM | HOM | HOM | GTAACCAGCAATCGACTCTGC (199) |
| rs1105813 | HOM | HET | HOM | | HOM | | HOM | HET | HOM | HET | GGCAGCGACTCAGCCTGTCCT (200) |
| | | HET | | HOM | | HOM | | HET | | HET | GGCAGCGACTTAGCCTGTCCT (201) |
| rs8522 | HET | HOM | HOM | | HOM | | HOM | HET | | | TGCTAACCCCAGCACTGGAGC (202) |
| | HET | | | HOM | | HOM | | HET | HOM | HOM | TGCTAACCCCGGCACTGGAGC (203) |

-continued

| | cfDNA ID# (HOM = homozygous; HET = heterozygous) | | | | | | | | | | SNP sequences |
|---|---|---|---|---|---|---|---|---|---|---|---|
| dbSNP ID | 19234 | 19268 | 19954 | 19337 | 19700 | 19117 | 19530 | 19970 | 19165 | 19755 | (SEQ ID NO) |
| rs16957022 | HET | HOM | HOM | | HOM | HOM | HOM | HET | HET | HOM | CAATGTCAAATGGGAAAAAGT (204) |
| | HET | | | HOM | | | | HET | HET | | CAATGTCAAACGGGAAAAAGT (205) |
| rs11078710 | HET | HOM | HOM | | HOM | | HOM | HET | | HET | GACAGGAGGACAGGATAAAAG (206) |
| | HET | | | HOM | | HOM | | HET | HOM | HET | GACAGGAGGAAAGGATAAAAG (207) |
| rs11078716 | HET | HOM | HOM | | HET | HET | HOM | | | HET | GGACCTAGATGCCAGGACCAT (208) |
| | HET | | | HOM | HET | HET | | HOM | HOM | HET | GGACCTAGATTCCAGGACCAT (209) |
| Gender | female | female | | | female | | | | | female | SRY negative |
| | | | male | male | | male | male | male | male | | SRY positive |

These results demonstrate that the strategy to generate next generation sequencing libraries for targeted sequencing, as depicted in FIGS. 1B-E result in reproducible, deep, and accurate reads into cell free dsDNA obtained from biological samples.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for generating a DNA library for targeted sequencing, comprising:

a) attaching a 5' end of an oligonucleotide adapter to a 3' end of a double-stranded DNA fragment to produce an adapter/fragment chimeric molecule;

b) producing complementary strands of the adapter/fragment chimeric molecule by linear amplification;

c) hybridizing the at least one complementary strand with an oligonucleotide probe, wherein the oligonucleotide probe comprises a hybridization domain with a sequence that hybridizes to a target sequence in the complement strand to produce a targeted complement strand/probe duplex;

d) isolating the targeted complement strand/probe duplex; and e) extending the probe in the isolated targeted complement strand/probe duplex and amplifying with PCR to produce a plurality of sequencing template molecules.

2. The method of claim 1, further comprising performing DNA sequencing of the plurality of sequencing molecules.

3. The method of claim 1, wherein the oligonucleotide adapter comprises one or more of the following in any combination:

a primer annealing domain with a nucleotide sequence that permits linear or exponential PCR amplification upon annealing of a primer;

a clone tag domain with a nucleotide sequence that uniquely labels each sequencing template molecule comprising sequence derived from the oligonucleotide adapter; and a sample tag domain with a nucleic acid sequence that labels independent samples of double-stranded DNA fragments and thereby allows multiplex analysis of multiple samples at once.

4. The method of claim 3, wherein the linear amplification is mediated by a thermostable DNA polymerase and a first primer that anneals to the primer annealing domain, and the linear amplification comprises one or more rounds of a two-step thermal cycling procedure.

5. The method of claim 1, wherein the oligonucleotide adapter comprises a phosphate group on the 5' end and/or a phosphorothioate modification in the 3' terminal phosphate linkage.

6. The method of claim 1, wherein the oligonucleotide adapter comprises a complementary duplex oligonucleotide annealed to its 5'end, wherein the complementary duplex oligonucleotide comprises a modification on its 3' end thereby preventing ligation of the double stranded DNA fragment to the complementary duplex and facilitating attachment of the 5' end of the oligonucleotide adapter to the double stranded DNA fragment.

7. The method of claim 1, wherein the oligonucleotide adapter is complementary to a complementary adapter strand in an oligonucleotide duplex, wherein the complementary adapter strand oligonucleotide comprises an internal C3 spacer to block full replication of an unligated strand.

8. The method of claim 1, further comprising dephosphorylating the 5' ends of the double-stranded DNA fragment prior to step (a).

9. The method of claim 1, further comprising, prior to step (a), contacting the DNA fragment with one or both of:

a DNA polymerase with 3' to 5' exonuclease activity to create blunt ends on the double-stranded DNA fragment prior to step (a); and a plurality of enzymes that mediate DNA repair.

10. The method of claim 9, wherein the DNA polymerase is T4 DNA polymerase, the Klenow fragment of *E. coli* DNA polymerase I, or a combination thereof, and/or wherein the DNA repair enzymes comprise full-length Bst DNA polymerase, Taq DNA ligase, Endonuclease IV, or any combination thereof.

11. The method of claim 1, wherein attaching the oligonucleotide adapter to the 3' end of the double-stranded DNA fragment comprises contacting the oligonucleotide adapter and double-stranded DNA fragment with a DNA ligation enzyme.

12. The method of claim 1, wherein the double-stranded DNA fragment is obtained from a biological sample obtained from a subject.

13. The method of claim 1, wherein the hybridization domain of the oligonucleotide probe is a 3' target-specific sequence, and wherein the oligonucleotide probe further comprises a 5' primer annealing domain.

14. The method of claim 13, wherein the oligonucleotide probe comprises a complementary duplex oligonucleotide annealed to the 5' primer annealing domain.

15. The method of claim 14, wherein the complementary duplex oligonucleotide comprises a 3' terminal biotin moiety and at least one dideoxy U base.

16. The method of claim 1, wherein the method is performed for a plurality of different double-stranded DNA fragments, wherein a plurality of different oligonucleotide probes are contacted to a plurality of complementary strands produced in step (b), and wherein the plurality of different oligonucleotide probes each comprises a hybridization domain with a different sequence that hybridizes to a different target sequence.

17. The method of claim 16, wherein the method results in a plurality of different sequencing molecules, and the method further comprises performing DNA sequencing the plurality of different sequencing molecules.

18. The method of claim 1, wherein a plurality of different adapter/fragment chimeric molecules is added to a single hybridization reaction in step (c).

19. The method of claim 1, wherein the hybridization step (c) and/or isolation step (d) is/are performed in an isostabilizing salt solution.

20. The method of claim 1, wherein the oligonucleotide probe comprises a biotin-modified tail and wherein the isolation of the targeted complement strand/probe duplex comprises binding of the biotin-modified tail of the oligonucleotide probe in the targeted complement strand/probe duplex to an avidin or streptavidin-coated paramagnetic bead.

21. The method of claim 20, wherein the biotin is tethered to the tail of the oligonucleotide by one or more deoxyuracil bases and wherein the complement strand/probe duplexes are separated from the paramagnetic beads following cleavage with an enzyme that specifically cleaves the phosphate backbone at deoxyuracil bases.

22. The method of claim 1, wherein the extension of the probe in step (e) comprises applying a thermostable DNA polymerase at ≥about 55° C., and the amplifying in step (e) comprises using a first PCR primer that selectively anneals to a primer annealing domain in the targeted complement strand of the duplex and a second PCR primer that selectively anneals to a primer annealing domain in the extended probe strand.

23. The method of claim 22, wherein the oligonucleotide adapter comprises a clone tag domain with a nucleotide sequence that labels each resulting genomic clone and a sample tag domain with a nucleic acid sequence that labels independent samples and thereby allow multiplex analysis of multiple samples at once, and wherein the method further comprises applying bioinformatics analysis that integrates alignment coordinates of obtained sequences of the double-stranded DNA fragment, the sequence of the clone tag domain, and the sequence of the sample tag domain.

* * * * *

SEQUENCE LISTING

<160> NUMBER OF SEQ ID NOS: 209

<210> SEQ ID NO 1
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C at postiion 1 is phosphorylated

<400> SEQUENCE: 1
ctcatggaga 10

<210> SEQ ID NO 2
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: A at postiion 1 is phosphorylated

<400> SEQUENCE: 2
agatgcctct 10

<210> SEQ ID NO 3
<211> LENGTH: 10
<212> TYPE: DNA
<213> ORGANISM: Artificial sequence
<220> FEATURE:

<223> OTHER INFORMATION: Synthetic
<220> FEATURE:
<221> NAME/KEY: misc_feature
<222> LOCATION: (1)..(1)
<223> OTHER INFORMATION: T at postiion 1 is phosphorylated

<400> SEQUENCE: 3
tctgcaagag 10

<210> SEQ ID NO 4
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: G at postiion 1 is phosphorylated

<400> SEQUENCE: 4
gagcattctc 10

<210> SEQ ID NO 5
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: G at postiion 1 is phosphorylated

<400> SEQUENCE: 5
gataactcgt 10

<210> SEQ ID NO 6
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C at postiion 1 is phosphorylated

<400> SEQUENCE: 6
ctgttagacg 10

<210> SEQ ID NO 7
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: A at postiion 1 is phosphorylated

<400> SEQUENCE: 7
agcggtctac 10

<210> SEQ ID NO 8
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: T at postiion 1 is phosphorylated

<400> SEQUENCE: 8
tcaccgagta 10

<210> SEQ ID NO 9
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: A at postiion 1 is phosphorylated

<400> SEQUENCE: 9
accattggtc 10

<210> SEQ ID NO 10
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C at postiion 1 is phosphorylated

<400> SEQUENCE: 10
caatggccga 10

<210> SEQ ID NO 11
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: G at postiion 1 is phosphorylated

<400> SEQUENCE: 11
gttgccaact 10

<210> SEQ ID NO 12
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: T at postiion 1 is phosphorylated

<400> SEQUENCE: 12
tggcaattag 10

<210> SEQ ID NO 13
<211> LENGTH: 10
<212> TYPE: DNA

<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: A at postiion 1 is phosphorylated

<400> SEQUENCE: 13
actcaagctg 10

<210> SEQ ID NO 14
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C at postiion 1 is phosphorylated

<400> SEQUENCE: 14
cagattcagc 10

<210> SEQ ID NO 15
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: G at postiion 1 is phosphorylated

<400> SEQUENCE: 15
gtctggatca 10

<210> SEQ ID NO 16
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: T at postiion 1 is phosphorylated

<400> SEQUENCE: 16
tgagcctgat 10

<210> SEQ ID NO 17
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 17
caactcccta cacgacgctc ttccgatctn nnnnnnntct ccatgag 47

<210> SEQ ID NO 18
<211> LENGTH: 47

```
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 18

caactcccta cacgacgctc ttccgatctn nnnnnnnaga ggcatct                47


<210> SEQ ID NO 19
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 19

caactcccta cacgacgctc ttccgatctn nnnnnnnctc ttgcaga                47


<210> SEQ ID NO 20
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 20

caactcccta cacgacgctc ttccgatctn nnnnnnngag aatgctc                47


<210> SEQ ID NO 21
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 21

caactcccta cacgacgctc ttccgatctn nnnnnnnacg agttatc                47


<210> SEQ ID NO 22
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 22

caactcccta cacgacgctc ttccgatctn nnnnnnncgt ctaacag                47


<210> SEQ ID NO 23
```

<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 23
caactcccta cacgacgctc ttccgatctn nnnnnnngta gaccgct 47

<210> SEQ ID NO 24
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 24
caactcccta cacgacgctc ttccgatctn nnnnnnntac tcggtga 47

<210> SEQ ID NO 25
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 25
caactcccta cacgacgctc ttccgatctn nnnnnnngac caatggt 47

<210> SEQ ID NO 26
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 26
caactcccta cacgacgctc ttccgatctn nnnnnnntcg gccattg 47

<210> SEQ ID NO 27
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 27
caactcccta cacgacgctc ttccgatctn nnnnnnnagt tggcaac 47

<210> SEQ ID NO 28
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 28
caactcccta cacgacgctc ttccgatctn nnnnnnncta attgcca 47

<210> SEQ ID NO 29
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 29
caactcccta cacgacgctc ttccgatctn nnnnnnncag cttgagt 47

<210> SEQ ID NO 30
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 30
caactcccta cacgacgctc ttccgatctn nnnnnnngct gaatctg 47

<210> SEQ ID NO 31
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 31
caactcccta cacgacgctc ttccgatctn nnnnnnntga tccagac 47

<210> SEQ ID NO 32
<211> LENGTH: 47
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 32
caactcccta cacgacgctc ttccgatctn nnnnnnnatc aggctca 47

```
<210> SEQ ID NO 33
<211> LENGTH: 58
<212> TYPE: DNA
<213> ORGANISM: Artificial sequence
<220> FEATURE:
<223> OTHER INFORMATION: Synthetic

<400> SEQUENCE: 33

aatgatacgg cgaccaccga gatctacact ctttccctac acgacgctct tccgatct       58


<210> SEQ ID NO 34
<211> LENGTH: 21
<212> TYPE: DNA
<213> ORGANISM: Artificial sequence
<220> FEATURE:
<223> OTHER INFORMATION: Synthetic

<400> SEQUENCE: 34

gaggctgagg caggagaatc g                                                21


<210> SEQ ID NO 35
<211> LENGTH: 58
<212> TYPE: DNA
<213> ORGANISM: Artificial sequence
<220> FEATURE:
<223> OTHER INFORMATION: Synthetic

<400> SEQUENCE: 35

aatgatacgg cgaccaccga gatctacact ctttccctac acgacgctct tccgatct       58


<210> SEQ ID NO 36
<211> LENGTH: 25
<212> TYPE: DNA
<213> ORGANISM: Artificial sequence
<220> FEATURE:
<223> OTHER INFORMATION: Synthetic

<400> SEQUENCE: 36

gtcgcagagc acttgcagac ttttt                                            25


<210> SEQ ID NO 37
<211> LENGTH: 25
<212> TYPE: DNA
<213> ORGANISM: Artificial sequence
<220> FEATURE:
<223> OTHER INFORMATION: Synthetic

<400> SEQUENCE: 37

aatgtggttt cgttggaagc aaatg                                            25


<210> SEQ ID NO 38
<211> LENGTH: 25
<212> TYPE: DNA
<213> ORGANISM: Artificial sequence
<220> FEATURE:
<223> OTHER INFORMATION: Synthetic

<400> SEQUENCE: 38

ttctgcttaa ccattgtggg catct                                            25


<210> SEQ ID NO 39
<211> LENGTH: 25
<212> TYPE: DNA
<213> ORGANISM: Artificial sequence
<220> FEATURE:
<223> OTHER INFORMATION: Synthetic
```

<400> SEQUENCE: 39
caatcaagat ggttttgcca aggaa 25

<210> SEQ ID NO 40
<211> LENGTH: 25
<212> TYPE: DNA
<213> ORGANISM: Artificial sequence
<220> FEATURE:
<223> OTHER INFORMATION: Synthetic

<400> SEQUENCE: 40
cgtatccccc tgcatttctt ttgtt 25

<210> SEQ ID NO 41
<211> LENGTH: 25
<212> TYPE: DNA
<213> ORGANISM: Artificial sequence
<220> FEATURE:
<223> OTHER INFORMATION: Synthetic

<400> SEQUENCE: 41
caaagggtga agaggaatcc caaag 25

<210> SEQ ID NO 42
<211> LENGTH: 25
<212> TYPE: DNA
<213> ORGANISM: Artificial sequence
<220> FEATURE:
<223> OTHER INFORMATION: Synthetic

<400> SEQUENCE: 42
tttatccatc ccatcacacc ctcag 25

<210> SEQ ID NO 43
<211> LENGTH: 25
<212> TYPE: DNA
<213> ORGANISM: Artificial sequence
<220> FEATURE:
<223> OTHER INFORMATION: Synthetic

<400> SEQUENCE: 43
aaagaaaagt tctgcatccc cagga 25

<210> SEQ ID NO 44
<211> LENGTH: 83
<212> TYPE: DNA
<213> ORGANISM: Artificial sequence
<220> FEATURE:
<223> OTHER INFORMATION: Synthetic

<400> SEQUENCE: 44
atacgagatg tgactggagt tcagacgtgt gctcttccga tctcccaggg ttggaagtgt 60
ctcatgctgg atccccactt ttc 83

<210> SEQ ID NO 45
<211> LENGTH: 83
<212> TYPE: DNA
<213> ORGANISM: Artificial sequence
<220> FEATURE:
<223> OTHER INFORMATION: Synthetic

<400> SEQUENCE: 45
atacgagatg tgactggagt tcagacgtgt gctcttccga tctgaggagc cgcagtcaga 60
tcctagcgtc gagccccctc tga 83

<210> SEQ ID NO 46
<211> LENGTH: 83
<212> TYPE: DNA
<213> ORGANISM: Artificial sequence
<220> FEATURE:
<223> OTHER INFORMATION: Synthetic

<400> SEQUENCE: 46
atacgagatg tgactggagt tcagacgtgt gctcttccga tcttccactc acagtttcca 60
taggtctgaa aatgtttcct gac 83

<210> SEQ ID NO 47
<211> LENGTH: 83
<212> TYPE: DNA
<213> ORGANISM: Artificial sequence
<220> FEATURE:
<223> OTHER INFORMATION: Synthetic

<400> SEQUENCE: 47
atacgagatg tgactggagt tcagacgtgt gctcttccga tctgaaaatt ccatgggact 60
gactttctgc tcttgtcttt cag 83

<210> SEQ ID NO 48
<211> LENGTH: 83
<212> TYPE: DNA
<213> ORGANISM: Artificial sequence
<220> FEATURE:
<223> OTHER INFORMATION: Synthetic

<400> SEQUENCE: 48
atacgagatg tgactggagt tcagacgtgt gctcttccga tctggctggg gggctggggg 60
gctgaggacc tggtcctctg act 83

<210> SEQ ID NO 49
<211> LENGTH: 83
<212> TYPE: DNA
<213> ORGANISM: Artificial sequence
<220> FEATURE:
<223> OTHER INFORMATION: Synthetic

<400> SEQUENCE: 49
atacgagatg tgactggagt tcagacgtgt gctcttccga tctcaatgga tgatttgatg 60
ctgtccccgg acgatattga aca 83

<210> SEQ ID NO 50
<211> LENGTH: 83
<212> TYPE: DNA
<213> ORGANISM: Artificial sequence
<220> FEATURE:
<223> OTHER INFORMATION: Synthetic

<400> SEQUENCE: 50
atacgagatg tgactggagt tcagacgtgt gctcttccga tctatgccag aggctgctcc 60
ccccgtggcc cctgcaccag cag 83

<210> SEQ ID NO 51
<211> LENGTH: 83
<212> TYPE: DNA
<213> ORGANISM: Artificial sequence
<220> FEATURE:
<223> OTHER INFORMATION: Synthetic

<400> SEQUENCE: 51
atacgagatg tgactggagt tcagacgtgt gctcttccga tctcctgtca tcttctgtcc 60
cttcccagaa aacctaccag ggc 83

<210> SEQ ID NO 52
<211> LENGTH: 83
<212> TYPE: DNA
<213> ORGANISM: Artificial sequence
<220> FEATURE:
<223> OTHER INFORMATION: Synthetic

<400> SEQUENCE: 52
atacgagatg tgactggagt tcagacgtgt gctcttccga tctgcagggg gatacggcca 60
ggcattgaag tctcatggaa gcc 83

<210> SEQ ID NO 53
<211> LENGTH: 83
<212> TYPE: DNA
<213> ORGANISM: Artificial sequence
<220> FEATURE:
<223> OTHER INFORMATION: Synthetic

<400> SEQUENCE: 53
atacgagatg tgactggagt tcagacgtgt gctcttccga tctctgtccc agaatgcaag 60
aagcccagac ggaaaccgta gct 83

<210> SEQ ID NO 54
<211> LENGTH: 83
<212> TYPE: DNA
<213> ORGANISM: Artificial sequence
<220> FEATURE:
<223> OTHER INFORMATION: Synthetic

<400> SEQUENCE: 54
atacgagatg tgactggagt tcagacgtgt gctcttccga tctggccagg agggggctgg 60
tgcaggggcc gccggtgtag gag 83

<210> SEQ ID NO 55
<211> LENGTH: 83
<212> TYPE: DNA
<213> ORGANISM: Artificial sequence
<220> FEATURE:
<223> OTHER INFORMATION: Synthetic

<400> SEQUENCE: 55
atacgagatg tgactggagt tcagacgtgt gctcttccga tcttctggga gcttcatctg 60
gacctgggtc ttcagtgaac cat 83

<210> SEQ ID NO 56
<211> LENGTH: 83
<212> TYPE: DNA
<213> ORGANISM: Artificial sequence
<220> FEATURE:
<223> OTHER INFORMATION: Synthetic

<400> SEQUENCE: 56
atacgagatg tgactggagt tcagacgtgt gctcttccga tctttcactt gtgccctgac 60
tttcaactct gtctccttcc tct 83

<210> SEQ ID NO 57

<211> LENGTH: 83
<212> TYPE: DNA
<213> ORGANISM: Artificial sequence
<220> FEATURE:
<223> OTHER INFORMATION: Synthetic

<400> SEQUENCE: 57
atacgagatg tgactggagt tcagacgtgt gctcttccga tctactggcc aagacctgcc 60
ctgtgcagct gtgggttgat tcc 83

<210> SEQ ID NO 58
<211> LENGTH: 83
<212> TYPE: DNA
<213> ORGANISM: Artificial sequence
<220> FEATURE:
<223> OTHER INFORMATION: Synthetic

<400> SEQUENCE: 58
atacgagatg tgactggagt tcagacgtgt gctcttccga tctacaagca gtcacagcac 60
atgacggagg ttgtgaggcg ctg 83

<210> SEQ ID NO 59
<211> LENGTH: 83
<212> TYPE: DNA
<213> ORGANISM: Artificial sequence
<220> FEATURE:
<223> OTHER INFORMATION: Synthetic

<400> SEQUENCE: 59
atacgagatg tgactggagt tcagacgtgt gctcttccga tctctgctca ccatcgctat 60
ctgagcagcg ctcatggtgg ggg 83

<210> SEQ ID NO 60
<211> LENGTH: 83
<212> TYPE: DNA
<213> ORGANISM: Artificial sequence
<220> FEATURE:
<223> OTHER INFORMATION: Synthetic

<400> SEQUENCE: 60
atacgagatg tgactggagt tcagacgtgt gctcttccga tctagatggc catggcgcgg 60
acgcgggtgc cgggcggggg tgt 83

<210> SEQ ID NO 61
<211> LENGTH: 83
<212> TYPE: DNA
<213> ORGANISM: Artificial sequence
<220> FEATURE:
<223> OTHER INFORMATION: Synthetic

<400> SEQUENCE: 61
atacgagatg tgactggagt tcagacgtgt gctcttccga tctagagacg acagggctgg 60
ttgcccaggg tccccaggcc tct 83

<210> SEQ ID NO 62
<211> LENGTH: 83
<212> TYPE: DNA
<213> ORGANISM: Artificial sequence
<220> FEATURE:
<223> OTHER INFORMATION: Synthetic

<400> SEQUENCE: 62
atacgagatg tgactggagt tcagacgtgt gctcttccga tctcatctta tccgagtgga 60
aggaaatttg cgtgtggagt att 83

<210> SEQ ID NO 63
<211> LENGTH: 83
<212> TYPE: DNA
<213> ORGANISM: Artificial sequence
<220> FEATURE:
<223> OTHER INFORMATION: Synthetic

<400> SEQUENCE: 63
atacgagatg tgactggagt tcagacgtgt gctcttccga tctcctggag ggccactgac 60
aaccaccctt aacccctcct ccc 83

<210> SEQ ID NO 64
<211> LENGTH: 83
<212> TYPE: DNA
<213> ORGANISM: Artificial sequence
<220> FEATURE:
<223> OTHER INFORMATION: Synthetic

<400> SEQUENCE: 64
atacgagatg tgactggagt tcagacgtgt gctcttccga tctggcacca ccacactatg 60
tcgaaaagtg tttctgtcat cca 83

<210> SEQ ID NO 65
<211> LENGTH: 83
<212> TYPE: DNA
<213> ORGANISM: Artificial sequence
<220> FEATURE:
<223> OTHER INFORMATION: Synthetic

<400> SEQUENCE: 65
atacgagatg tgactggagt tcagacgtgt gctcttccga tctcccctgc ttgccacagg 60
tctccccaag gcgcactggc ctc 83

<210> SEQ ID NO 66
<211> LENGTH: 83
<212> TYPE: DNA
<213> ORGANISM: Artificial sequence
<220> FEATURE:
<223> OTHER INFORMATION: Synthetic

<400> SEQUENCE: 66
atacgagatg tgactggagt tcagacgtgt gctcttccga tctaccacca tccactacaa 60
ctacatgtgt aacagttcct gca 83

<210> SEQ ID NO 67
<211> LENGTH: 83
<212> TYPE: DNA
<213> ORGANISM: Artificial sequence
<220> FEATURE:
<223> OTHER INFORMATION: Synthetic

<400> SEQUENCE: 67
atacgagatg tgactggagt tcagacgtgt gctcttccga tctggtcaga ggcaagcaga 60
ggctggggca cagcaggcca gtg 83

<210> SEQ ID NO 68
<211> LENGTH: 83
<212> TYPE: DNA
<213> ORGANISM: Artificial sequence
<220> FEATURE:

<223> OTHER INFORMATION: Synthetic

<400> SEQUENCE: 68
atacgagatg tgactggagt tcagacgtgt gctcttccga tctgtgatga tggtgaggat 60
gggcctccgg ttcatgccgc cca 83

<210> SEQ ID NO 69
<211> LENGTH: 83
<212> TYPE: DNA
<213> ORGANISM: Artificial sequence
<220> FEATURE:
<223> OTHER INFORMATION: Synthetic

<400> SEQUENCE: 69
atacgagatg tgactggagt tcagacgtgt gctcttccga tcttaggacc tgatttcctt 60
actgcctctt gcttctcttt tcc 83

<210> SEQ ID NO 70
<211> LENGTH: 83
<212> TYPE: DNA
<213> ORGANISM: Artificial sequence
<220> FEATURE:
<223> OTHER INFORMATION: Synthetic

<400> SEQUENCE: 70
atacgagatg tgactggagt tcagacgtgt gctcttccga tctgaggtgc gtgtttgtgc 60
ctgtcctggg agagaccggc gca 83

<210> SEQ ID NO 71
<211> LENGTH: 83
<212> TYPE: DNA
<213> ORGANISM: Artificial sequence
<220> FEATURE:
<223> OTHER INFORMATION: Synthetic

<400> SEQUENCE: 71
atacgagatg tgactggagt tcagacgtgt gctcttccga tctgcataac tgcacccttg 60
gtctcctcca ccgcttcttg tcc 83

<210> SEQ ID NO 72
<211> LENGTH: 83
<212> TYPE: DNA
<213> ORGANISM: Artificial sequence
<220> FEATURE:
<223> OTHER INFORMATION: Synthetic

<400> SEQUENCE: 72
atacgagatg tgactggagt tcagacgtgt gctcttccga tcttggtgag gctccccttt 60
cttgcggaga ttctcttcct ctg 83

<210> SEQ ID NO 73
<211> LENGTH: 83
<212> TYPE: DNA
<213> ORGANISM: Artificial sequence
<220> FEATURE:
<223> OTHER INFORMATION: Synthetic

<400> SEQUENCE: 73
atacgagatg tgactggagt tcagacgtgt gctcttccga tctgagacca agggtgcagt 60
tatgcctcag attcactttt atc 83

<210> SEQ ID NO 74
<211> LENGTH: 83
<212> TYPE: DNA
<213> ORGANISM: Artificial sequence
<220> FEATURE:
<223> OTHER INFORMATION: Synthetic

<400> SEQUENCE: 74
atacgagatg tgactggagt tcagacgtgt gctcttccga tctagctcct ctccccagcc 60
aaagaagaaa ccactggatg gag 83

<210> SEQ ID NO 75
<211> LENGTH: 83
<212> TYPE: DNA
<213> ORGANISM: Artificial sequence
<220> FEATURE:
<223> OTHER INFORMATION: Synthetic

<400> SEQUENCE: 75
atacgagatg tgactggagt tcagacgtgt gctcttccga tcttaagagg tcccaagact 60
tagtacctga agggtgaaat att 83

<210> SEQ ID NO 76
<211> LENGTH: 83
<212> TYPE: DNA
<213> ORGANISM: Artificial sequence
<220> FEATURE:
<223> OTHER INFORMATION: Synthetic

<400> SEQUENCE: 76
atacgagatg tgactggagt tcagacgtgt gctcttccga tctcttgaac catcttttaa 60
ctcaggtact gtgtatatac tta 83

<210> SEQ ID NO 77
<211> LENGTH: 83
<212> TYPE: DNA
<213> ORGANISM: Artificial sequence
<220> FEATURE:
<223> OTHER INFORMATION: Synthetic

<400> SEQUENCE: 77
atacgagatg tgactggagt tcagacgtgt gctcttccga tctgcgcttc gagatgttcc 60
gagagctgaa tgaggccttg gaa 83

<210> SEQ ID NO 78
<211> LENGTH: 83
<212> TYPE: DNA
<213> ORGANISM: Artificial sequence
<220> FEATURE:
<223> OTHER INFORMATION: Synthetic

<400> SEQUENCE: 78
atacgagatg tgactggagt tcagacgtgt gctcttccga tctgaatcct atggctttcc 60
aacctaggaa ggcaggggag tag 83

<210> SEQ ID NO 79
<211> LENGTH: 83
<212> TYPE: DNA
<213> ORGANISM: Artificial sequence
<220> FEATURE:
<223> OTHER INFORMATION: Synthetic

<400> SEQUENCE: 79
atacgagatg tgactggagt tcagacgtgt gctcttccga tcttgctccc ccctggctcc 60
ttcccagcct gggcatcctt gag 83

<210> SEQ ID NO 80
<211> LENGTH: 83
<212> TYPE: DNA
<213> ORGANISM: Artificial sequence
<220> FEATURE:
<223> OTHER INFORMATION: Synthetic

<400> SEQUENCE: 80
atacgagatg tgactggagt tcagacgtgt gctcttccga tctggcacag accctctcac 60
tcatgtgatg tcatctctcc tcc 83

<210> SEQ ID NO 81
<211> LENGTH: 83
<212> TYPE: DNA
<213> ORGANISM: Artificial sequence
<220> FEATURE:
<223> OTHER INFORMATION: Synthetic

<400> SEQUENCE: 81
atacgagatg tgactggagt tcagacgtgt gctcttccga tcttcagtct acctcccgcc 60
ataaaaaact catgttcaag aca 83

<210> SEQ ID NO 82
<211> LENGTH: 83
<212> TYPE: DNA
<213> ORGANISM: Artificial sequence
<220> FEATURE:
<223> OTHER INFORMATION: Synthetic

<400> SEQUENCE: 82
atacgagatg tgactggagt tcagacgtgt gctcttccga tctgaacaag aagtggagaa 60
tgtcagtctg agtcaggccc ttc 83

<210> SEQ ID NO 83
<211> LENGTH: 83
<212> TYPE: DNA
<213> ORGANISM: Artificial sequence
<220> FEATURE:
<223> OTHER INFORMATION: Synthetic

<400> SEQUENCE: 83
atacgagatg tgactggagt tcagacgtgt gctcttccga tctcaagtga acagataaag 60
caactggaag acggcagcaa aga 83

<210> SEQ ID NO 84
<211> LENGTH: 83
<212> TYPE: DNA
<213> ORGANISM: Artificial sequence
<220> FEATURE:
<223> OTHER INFORMATION: Synthetic

<400> SEQUENCE: 84
atacgagatg tgactggagt tcagacgtgt gctcttccga tcttctgtag ctgtagaggc 60
attttaaccc tttgtcctcc agc 83

<210> SEQ ID NO 85
<211> LENGTH: 83
<212> TYPE: DNA
<213> ORGANISM: Artificial sequence
<220> FEATURE:
<223> OTHER INFORMATION: Synthetic

<400> SEQUENCE: 85
atacgagatg tgactggagt tcagacgtgt gctcttccga tctcctccct gtctcacgcc 60
atggtagcgt ccgcctaggt tgc 83

<210> SEQ ID NO 86
<211> LENGTH: 83
<212> TYPE: DNA
<213> ORGANISM: Artificial sequence
<220> FEATURE:
<223> OTHER INFORMATION: Synthetic

<400> SEQUENCE: 86
atacgagatg tgactggagt tcagacgtgt gctcttccga tctcccggtt gtccccagat 60
cctgtggctg gctcagctgt gtc 83

<210> SEQ ID NO 87
<211> LENGTH: 83
<212> TYPE: DNA
<213> ORGANISM: Artificial sequence
<220> FEATURE:
<223> OTHER INFORMATION: Synthetic

<400> SEQUENCE: 87
atacgagatg tgactggagt tcagacgtgt gctcttccga tcttcacttg ttctatatta 60
ttattctaga gagaactgtg tga 83

<210> SEQ ID NO 88
<211> LENGTH: 83
<212> TYPE: DNA
<213> ORGANISM: Artificial sequence
<220> FEATURE:
<223> OTHER INFORMATION: Synthetic

<400> SEQUENCE: 88
atacgagatg tgactggagt tcagacgtgt gctcttccga tcttttaaat cccgtaatcc 60
ttggtgagag gctgccgagg ggg 83

<210> SEQ ID NO 89
<211> LENGTH: 83
<212> TYPE: DNA
<213> ORGANISM: Artificial sequence
<220> FEATURE:
<223> OTHER INFORMATION: Synthetic

<400> SEQUENCE: 89
atacgagatg tgactggagt tcagacgtgt gctcttccga tctgctaagt tgcaggtact 60
ttttgataac tttaggactt ggg 83

<210> SEQ ID NO 90
<211> LENGTH: 83
<212> TYPE: DNA
<213> ORGANISM: Artificial sequence
<220> FEATURE:
<223> OTHER INFORMATION: Synthetic

<400> SEQUENCE: 90
atacgagatg tgactggagt tcagacgtgt gctcttccga tctctccagg cagctggctc 60
tggtattcag aatcagaacg gac 83

<210> SEQ ID NO 91
<211> LENGTH: 83
<212> TYPE: DNA
<213> ORGANISM: Artificial sequence
<220> FEATURE:
<223> OTHER INFORMATION: Synthetic

<400> SEQUENCE: 91
atacgagatg tgactggagt tcagacgtgt gctcttccga tctaatcatg tccatcagat 60
gacggcagat gctgtttgca gtc 83

<210> SEQ ID NO 92
<211> LENGTH: 83
<212> TYPE: DNA
<213> ORGANISM: Artificial sequence
<220> FEATURE:
<223> OTHER INFORMATION: Synthetic

<400> SEQUENCE: 92
atacgagatg tgactggagt tcagacgtgt gctcttccga tcttctccaa aatccactga 60
gcagacaacc acaaacagtg tta 83

<210> SEQ ID NO 93
<211> LENGTH: 83
<212> TYPE: DNA
<213> ORGANISM: Artificial sequence
<220> FEATURE:
<223> OTHER INFORMATION: Synthetic

<400> SEQUENCE: 93
atacgagatg tgactggagt tcagacgtgt gctcttccga tctaagtgaa aatgtttgac 60
ttactggcat gatcagaatg ctg 83

<210> SEQ ID NO 94
<211> LENGTH: 83
<212> TYPE: DNA
<213> ORGANISM: Artificial sequence
<220> FEATURE:
<223> OTHER INFORMATION: Synthetic

<400> SEQUENCE: 94
atacgagatg tgactggagt tcagacgtgt gctcttccga tctaataaag cttctgtcaa 60
actcttagat gaatgactac acc 83

<210> SEQ ID NO 95
<211> LENGTH: 83
<212> TYPE: DNA
<213> ORGANISM: Artificial sequence
<220> FEATURE:
<223> OTHER INFORMATION: Synthetic

<400> SEQUENCE: 95
atacgagatg tgactggagt tcagacgtgt gctcttccga tcttgttttc atggggctct 60
gagattcttc catcccttct cca 83

<210> SEQ ID NO 96
<211> LENGTH: 83
<212> TYPE: DNA
<213> ORGANISM: Artificial sequence
<220> FEATURE:
<223> OTHER INFORMATION: Synthetic

<400> SEQUENCE: 96
atacgagatg tgactggagt tcagacgtgt gctcttccga tctggctttt cccatcaaca 60
aggcagagag ctgaggattg tct 83

<210> SEQ ID NO 97
<211> LENGTH: 83
<212> TYPE: DNA
<213> ORGANISM: Artificial sequence
<220> FEATURE:
<223> OTHER INFORMATION: Synthetic

<400> SEQUENCE: 97
atacgagatg tgactggagt tcagacgtgt gctcttccga tcttccacct gaggtagcag 60
tgtgagagga gaggtgattg aga 83

<210> SEQ ID NO 98
<211> LENGTH: 83
<212> TYPE: DNA
<213> ORGANISM: Artificial sequence
<220> FEATURE:
<223> OTHER INFORMATION: Synthetic

<400> SEQUENCE: 98
atacgagatg tgactggagt tcagacgtgt gctcttccga tctaaactca gaatatacag 60
aatttaaaat attaaagaga aaa 83

<210> SEQ ID NO 99
<211> LENGTH: 83
<212> TYPE: DNA
<213> ORGANISM: Artificial sequence
<220> FEATURE:
<223> OTHER INFORMATION: Synthetic

<400> SEQUENCE: 99
atacgagatg tgactggagt tcagacgtgt gctcttccga tctagtgtgt ggctttcgta 60
cagtcatccc tgtacaacct gtt 83

<210> SEQ ID NO 100
<211> LENGTH: 83
<212> TYPE: DNA
<213> ORGANISM: Artificial sequence
<220> FEATURE:
<223> OTHER INFORMATION: Synthetic

<400> SEQUENCE: 100
atacgagatg tgactggagt tcagacgtgt gctcttccga tctgcatggc ctgtaatttc 60
tgtgcctcct ggaagaatgg cca 83

<210> SEQ ID NO 101
<211> LENGTH: 83
<212> TYPE: DNA
<213> ORGANISM: Artificial sequence
<220> FEATURE:
<223> OTHER INFORMATION: Synthetic

<400> SEQUENCE: 101
atacgagatg tgactggagt tcagacgtgt gctcttccga tcttcctcat ggtcttttgg 60
ttatatctca tttgttcctt cct 83

<210> SEQ ID NO 102
<211> LENGTH: 83
<212> TYPE: DNA

<213> ORGANISM: Artificial sequence
<220> FEATURE:
<223> OTHER INFORMATION: Synthetic

<400> SEQUENCE: 102
atacgagatg tgactggagt tcagacgtgt gctcttccga tctctggctg agaacagggc 60
agtgaaaggg aactgggtga caa 83

<210> SEQ ID NO 103
<211> LENGTH: 83
<212> TYPE: DNA
<213> ORGANISM: Artificial sequence
<220> FEATURE:
<223> OTHER INFORMATION: Synthetic

<400> SEQUENCE: 103
atacgagatg tgactggagt tcagacgtgt gctcttccga tctcacggaa gggtcagggg 60
caaggactcc atgtgatggg tac 83

<210> SEQ ID NO 104
<211> LENGTH: 83
<212> TYPE: DNA
<213> ORGANISM: Artificial sequence
<220> FEATURE:
<223> OTHER INFORMATION: Synthetic

<400> SEQUENCE: 104
atacgagatg tgactggagt tcagacgtgt gctcttccga tctcgggagc tgcagttccc 60
caccccctcc atcttgctgc ttg 83

<210> SEQ ID NO 105
<211> LENGTH: 83
<212> TYPE: DNA
<213> ORGANISM: Artificial sequence
<220> FEATURE:
<223> OTHER INFORMATION: Synthetic

<400> SEQUENCE: 105
atacgagatg tgactggagt tcagacgtgt gctcttccga tctaaaacag atgaaaagca 60
agatacttct agctggccag cca 83

<210> SEQ ID NO 106
<211> LENGTH: 83
<212> TYPE: DNA
<213> ORGANISM: Artificial sequence
<220> FEATURE:
<223> OTHER INFORMATION: Synthetic

<400> SEQUENCE: 106
atacgagatg tgactggagt tcagacgtgt gctcttccga tctaaccatt agtccctgag 60
aaggtggcag gggtgagact aag 83

<210> SEQ ID NO 107
<211> LENGTH: 83
<212> TYPE: DNA
<213> ORGANISM: Artificial sequence
<220> FEATURE:
<223> OTHER INFORMATION: Synthetic

<400> SEQUENCE: 107
atacgagatg tgactggagt tcagacgtgt gctcttccga tcttaaggct ggcttcctaa 60
acttcattct ccccaaactg ctt 83

<210> SEQ ID NO 108
<211> LENGTH: 83
<212> TYPE: DNA
<213> ORGANISM: Artificial sequence
<220> FEATURE:
<223> OTHER INFORMATION: Synthetic

<400> SEQUENCE: 108
atacgagatg tgactggagt tcagacgtgt gctcttccga tctctcttgc agcagccaga 60
ctgccttccg ggtcactgcc atg 83

<210> SEQ ID NO 109
<211> LENGTH: 83
<212> TYPE: DNA
<213> ORGANISM: Artificial sequence
<220> FEATURE:
<223> OTHER INFORMATION: Synthetic

<400> SEQUENCE: 109
atacgagatg tgactggagt tcagacgtgt gctcttccga tctggggttg gggtgggggt 60
ggtgggcctg cccttccaat gga 83

<210> SEQ ID NO 110
<211> LENGTH: 83
<212> TYPE: DNA
<213> ORGANISM: Artificial sequence
<220> FEATURE:
<223> OTHER INFORMATION: Synthetic

<400> SEQUENCE: 110
atacgagatg tgactggagt tcagacgtgt gctcttccga tcttcagagg gggctcgacg 60
ctaggatctg actgcggctc ctc 83

<210> SEQ ID NO 111
<211> LENGTH: 83
<212> TYPE: DNA
<213> ORGANISM: Artificial sequence
<220> FEATURE:
<223> OTHER INFORMATION: Synthetic

<400> SEQUENCE: 111
atacgagatg tgactggagt tcagacgtgt gctcttccga tctgctcttt tcacccatct 60
acagtccccc ttgccgtccc aag 83

<210> SEQ ID NO 112
<211> LENGTH: 83
<212> TYPE: DNA
<213> ORGANISM: Artificial sequence
<220> FEATURE:
<223> OTHER INFORMATION: Synthetic

<400> SEQUENCE: 112
atacgagatg tgactggagt tcagacgtgt gctcttccga tctatggttc actgaagacc 60
caggtccaga tgaagctccc aga 83

<210> SEQ ID NO 113
<211> LENGTH: 83
<212> TYPE: DNA
<213> ORGANISM: Artificial sequence
<220> FEATURE:
<223> OTHER INFORMATION: Synthetic

<400> SEQUENCE: 113
atacgagatg tgactggagt tcagacgtgt gctcttccga tctctcctac accggcggcc 60
cctgcaccag ccccctcctg gcc 83

<210> SEQ ID NO 114
<211> LENGTH: 83
<212> TYPE: DNA
<213> ORGANISM: Artificial sequence
<220> FEATURE:
<223> OTHER INFORMATION: Synthetic

<400> SEQUENCE: 114
atacgagatg tgactggagt tcagacgtgt gctcttccga tctagctacg gtttccgtct 60
gggcttcttg cattctggga cag 83

<210> SEQ ID NO 115
<211> LENGTH: 83
<212> TYPE: DNA
<213> ORGANISM: Artificial sequence
<220> FEATURE:
<223> OTHER INFORMATION: Synthetic

<400> SEQUENCE: 115
atacgagatg tgactggagt tcagacgtgt gctcttccga tctagcccct cagggcaact 60
gaccgtgcaa gtcacagact tgg 83

<210> SEQ ID NO 116
<211> LENGTH: 83
<212> TYPE: DNA
<213> ORGANISM: Artificial sequence
<220> FEATURE:
<223> OTHER INFORMATION: Synthetic

<400> SEQUENCE: 116
atacgagatg tgactggagt tcagacgtgt gctcttccga tctgccctgg taggttttct 60
gggaagggac agaagatgac agg 83

<210> SEQ ID NO 117
<211> LENGTH: 83
<212> TYPE: DNA
<213> ORGANISM: Artificial sequence
<220> FEATURE:
<223> OTHER INFORMATION: Synthetic

<400> SEQUENCE: 117
atacgagatg tgactggagt tcagacgtgt gctcttccga tctctgctgg tgcaggggcc 60
acggggggag cagcctctgg cat 83

<210> SEQ ID NO 118
<211> LENGTH: 83
<212> TYPE: DNA
<213> ORGANISM: Artificial sequence
<220> FEATURE:
<223> OTHER INFORMATION: Synthetic

<400> SEQUENCE: 118
atacgagatg tgactggagt tcagacgtgt gctcttccga tcttgttcaa tatcgtccgg 60
ggacagcatc aaatcatcca ttg 83

<210> SEQ ID NO 119
<211> LENGTH: 83

<212> TYPE: DNA
<213> ORGANISM: Artificial sequence
<220> FEATURE:
<223> OTHER INFORMATION: Synthetic

<400> SEQUENCE: 119
atacgagatg tgactggagt tcagacgtgt gctcttccga tcttcctaca gtactcccct 60
gccctcaaca agatgttttg cca 83

<210> SEQ ID NO 120
<211> LENGTH: 83
<212> TYPE: DNA
<213> ORGANISM: Artificial sequence
<220> FEATURE:
<223> OTHER INFORMATION: Synthetic

<400> SEQUENCE: 120
atacgagatg tgactggagt tcagacgtgt gctcttccga tctacacccc cgcccggcac 60
ccgcgtccgc gccatggcca tct 83

<210> SEQ ID NO 121
<211> LENGTH: 83
<212> TYPE: DNA
<213> ORGANISM: Artificial sequence
<220> FEATURE:
<223> OTHER INFORMATION: Synthetic

<400> SEQUENCE: 121
atacgagatg tgactggagt tcagacgtgt gctcttccga tctggaccct gggcaaccag 60
ccctgtcgtc tctccagccc cag 83

<210> SEQ ID NO 122
<211> LENGTH: 83
<212> TYPE: DNA
<213> ORGANISM: Artificial sequence
<220> FEATURE:
<223> OTHER INFORMATION: Synthetic

<400> SEQUENCE: 122
atacgagatg tgactggagt tcagacgtgt gctcttccga tctcagcgcc tcacaacctc 60
cgtcatgtgc tgtgactgct tgt 83

<210> SEQ ID NO 123
<211> LENGTH: 83
<212> TYPE: DNA
<213> ORGANISM: Artificial sequence
<220> FEATURE:
<223> OTHER INFORMATION: Synthetic

<400> SEQUENCE: 123
atacgagatg tgactggagt tcagacgtgt gctcttccga tctggaatca acccacagct 60
gcacagggca ggtcttggcc agt 83

<210> SEQ ID NO 124
<211> LENGTH: 83
<212> TYPE: DNA
<213> ORGANISM: Artificial sequence
<220> FEATURE:
<223> OTHER INFORMATION: Synthetic

<400> SEQUENCE: 124
atacgagatg tgactggagt tcagacgtgt gctcttccga tctgattcct cactgattgc 60
tcttaggtct ggcccctcct cag 83

<210> SEQ ID NO 125
<211> LENGTH: 83
<212> TYPE: DNA
<213> ORGANISM: Artificial sequence
<220> FEATURE:
<223> OTHER INFORMATION: Synthetic

<400> SEQUENCE: 125
atacgagatg tgactggagt tcagacgtgt gctcttccga tcttggatga cagaaacact 60
tttcgacata gtgtggtggt gcc 83

<210> SEQ ID NO 126
<211> LENGTH: 83
<212> TYPE: DNA
<213> ORGANISM: Artificial sequence
<220> FEATURE:
<223> OTHER INFORMATION: Synthetic

<400> SEQUENCE: 126
atacgagatg tgactggagt tcagacgtgt gctcttccga tctagagacc ccagttgcaa 60
accagacctc aggcggctca tag 83

<210> SEQ ID NO 127
<211> LENGTH: 83
<212> TYPE: DNA
<213> ORGANISM: Artificial sequence
<220> FEATURE:
<223> OTHER INFORMATION: Synthetic

<400> SEQUENCE: 127
atacgagatg tgactggagt tcagacgtgt gctcttccga tctaatactc cacacgcaaa 60
tttccttcca ctcggataag atg 83

<210> SEQ ID NO 128
<211> LENGTH: 83
<212> TYPE: DNA
<213> ORGANISM: Artificial sequence
<220> FEATURE:
<223> OTHER INFORMATION: Synthetic

<400> SEQUENCE: 128
atacgagatg tgactggagt tcagacgtgt gctcttccga tctatcttgg gcctgtgtta 60
tctcctaggt tggctctgac tgt 83

<210> SEQ ID NO 129
<211> LENGTH: 83
<212> TYPE: DNA
<213> ORGANISM: Artificial sequence
<220> FEATURE:
<223> OTHER INFORMATION: Synthetic

<400> SEQUENCE: 129
atacgagatg tgactggagt tcagacgtgt gctcttccga tcttgggcgg catgaaccgg 60
aggcccatcc tcaccatcat cac 83

<210> SEQ ID NO 130
<211> LENGTH: 83
<212> TYPE: DNA
<213> ORGANISM: Artificial sequence
<220> FEATURE:
<223> OTHER INFORMATION: Synthetic

<400> SEQUENCE: 130
atacgagatg tgactggagt tcagacgtgt gctcttccga tcttgcaggg tggcaagtgg 60
ctcctgacct ggagtcttcc agt 83

<210> SEQ ID NO 131
<211> LENGTH: 83
<212> TYPE: DNA
<213> ORGANISM: Artificial sequence
<220> FEATURE:
<223> OTHER INFORMATION: Synthetic

<400> SEQUENCE: 131
atacgagatg tgactggagt tcagacgtgt gctcttccga tcttgcagga actgttacac 60
atgtagttgt agtggatggt ggt 83

<210> SEQ ID NO 132
<211> LENGTH: 83
<212> TYPE: DNA
<213> ORGANISM: Artificial sequence
<220> FEATURE:
<223> OTHER INFORMATION: Synthetic

<400> SEQUENCE: 132
atacgagatg tgactggagt tcagacgtgt gctcttccga tcttatcctg agtagtggta 60
atctactggg acggaacagc ttt 83

<210> SEQ ID NO 133
<211> LENGTH: 83
<212> TYPE: DNA
<213> ORGANISM: Artificial sequence
<220> FEATURE:
<223> OTHER INFORMATION: Synthetic

<400> SEQUENCE: 133
atacgagatg tgactggagt tcagacgtgt gctcttccga tcttgcttgc ttacctcgct 60
tagtgctccc tgggggcagc tcg 83

<210> SEQ ID NO 134
<211> LENGTH: 83
<212> TYPE: DNA
<213> ORGANISM: Artificial sequence
<220> FEATURE:
<223> OTHER INFORMATION: Synthetic

<400> SEQUENCE: 134
atacgagatg tgactggagt tcagacgtgt gctcttccga tcttgcgccg gtctctccca 60
ggacaggcac aaacacgcac ctc 83

<210> SEQ ID NO 135
<211> LENGTH: 83
<212> TYPE: DNA
<213> ORGANISM: Artificial sequence
<220> FEATURE:
<223> OTHER INFORMATION: Synthetic

<400> SEQUENCE: 135
atacgagatg tgactggagt tcagacgtgt gctcttccga tctacctttc cttgcctctt 60
tcctagcact gcccaacaac acc 83

<210> SEQ ID NO 136

<211> LENGTH: 83
<212> TYPE: DNA
<213> ORGANISM: Artificial sequence
<220> FEATURE:
<223> OTHER INFORMATION: Synthetic

<400> SEQUENCE: 136
atacgagatg tgactggagt tcagacgtgt gctcttccga tctaacggca ttttgagtgt 60
tagactggaa actttccact tga 83

<210> SEQ ID NO 137
<211> LENGTH: 83
<212> TYPE: DNA
<213> ORGANISM: Artificial sequence
<220> FEATURE:
<223> OTHER INFORMATION: Synthetic

<400> SEQUENCE: 137
atacgagatg tgactggagt tcagacgtgt gctcttccga tctctccatc cagtggtttc 60
ttctttggct ggggagagga gct 83

<210> SEQ ID NO 138
<211> LENGTH: 83
<212> TYPE: DNA
<213> ORGANISM: Artificial sequence
<220> FEATURE:
<223> OTHER INFORMATION: Synthetic

<400> SEQUENCE: 138
atacgagatg tgactggagt tcagacgtgt gctcttccga tctcttctcc ccctcctctg 60
ttgctgcaga tccgtgggcg tga 83

<210> SEQ ID NO 139
<211> LENGTH: 83
<212> TYPE: DNA
<213> ORGANISM: Artificial sequence
<220> FEATURE:
<223> OTHER INFORMATION: Synthetic

<400> SEQUENCE: 139
atacgagatg tgactggagt tcagacgtgt gctcttccga tctctcaagg atgcccaggc 60
tgggaaggag ccaggggga gca 83

<210> SEQ ID NO 140
<211> LENGTH: 83
<212> TYPE: DNA
<213> ORGANISM: Artificial sequence
<220> FEATURE:
<223> OTHER INFORMATION: Synthetic

<400> SEQUENCE: 140
atacgagatg tgactggagt tcagacgtgt gctcttccga tctggccagg aaggggctga 60
ggtcactcac ctggagtgag ccc 83

<210> SEQ ID NO 141
<211> LENGTH: 83
<212> TYPE: DNA
<213> ORGANISM: Artificial sequence
<220> FEATURE:
<223> OTHER INFORMATION: Synthetic

<400> SEQUENCE: 141
atacgagatg tgactggagt tcagacgtgt gctcttccga tctttccaag gcctcattca 60
gctctcggaa catctcgaag cgc 83

<210> SEQ ID NO 142
<211> LENGTH: 83
<212> TYPE: DNA
<213> ORGANISM: Artificial sequence
<220> FEATURE:
<223> OTHER INFORMATION: Synthetic

<400> SEQUENCE: 142
atacgagatg tgactggagt tcagacgtgt gctcttccga tctctgcttc tgtctcctac 60
agccacctga agtccaaaaa ggg 83

<210> SEQ ID NO 143
<211> LENGTH: 83
<212> TYPE: DNA
<213> ORGANISM: Artificial sequence
<220> FEATURE:
<223> OTHER INFORMATION: Synthetic

<400> SEQUENCE: 143
atacgagatg tgactggagt tcagacgtgt gctcttccga tctgcagggg agggagagat 60
gggggtggga ggctgtcagt ggg 83

<210> SEQ ID NO 144
<211> LENGTH: 83
<212> TYPE: DNA
<213> ORGANISM: Artificial sequence
<220> FEATURE:
<223> OTHER INFORMATION: Synthetic

<400> SEQUENCE: 144
atacgagatg tgactggagt tcagacgtgt gctcttccga tcttgtcttg aacatgagtt 60
ttttatggcg ggaggtagac tga 83

<210> SEQ ID NO 145
<211> LENGTH: 83
<212> TYPE: DNA
<213> ORGANISM: Artificial sequence
<220> FEATURE:
<223> OTHER INFORMATION: Synthetic

<400> SEQUENCE: 145
atacgagatg tgactggagt tcagacgtgt gctcttccga tcttagacgc caactctctc 60
tagctcgcta gtgggttgca gga 83

<210> SEQ ID NO 146
<211> LENGTH: 83
<212> TYPE: DNA
<213> ORGANISM: Artificial sequence
<220> FEATURE:
<223> OTHER INFORMATION: Synthetic

<400> SEQUENCE: 146
atacgagatg tgactggagt tcagacgtgt gctcttccga tctggaggct gcagcattaa 60
aaaaagaaaa aggaggttag aga 83

<210> SEQ ID NO 147
<211> LENGTH: 83
<212> TYPE: DNA
<213> ORGANISM: Artificial sequence
<220> FEATURE:

<223> OTHER INFORMATION: Synthetic

<400> SEQUENCE: 147
atacgagatg tgactggagt tcagacgtgt gctcttccga tcttgatgca aacctcaatc 60 cctcccctc tttgaatggt gtg 83

<210> SEQ ID NO 148
<211> LENGTH: 83
<212> TYPE: DNA
<213> ORGANISM: Artificial sequence
<220> FEATURE:
<223> OTHER INFORMATION: Synthetic

<400> SEQUENCE: 148
atacgagatg tgactggagt tcagacgtgt gctcttccga tctccaaact ctgtttccag 60
gggagtggag agagaaactg ggt 83

<210> SEQ ID NO 149
<211> LENGTH: 83
<212> TYPE: DNA
<213> ORGANISM: Artificial sequence
<220> FEATURE:
<223> OTHER INFORMATION: Synthetic

<400> SEQUENCE: 149
atacgagatg tgactggagt tcagacgtgt gctcttccga tctgaggtgt acttgcatta 60
atggagtggg ggtgggagca gta 83

<210> SEQ ID NO 150
<211> LENGTH: 83
<212> TYPE: DNA
<213> ORGANISM: Artificial sequence
<220> FEATURE:
<223> OTHER INFORMATION: Synthetic

<400> SEQUENCE: 150
atacgagatg tgactggagt tcagacgtgt gctcttccga tctcctccgg ccacggctgg 60
cacaaggttc tctccctccc ctg 83

<210> SEQ ID NO 151
<211> LENGTH: 83
<212> TYPE: DNA
<213> ORGANISM: Artificial sequence
<220> FEATURE:
<223> OTHER INFORMATION: Synthetic

<400> SEQUENCE: 151
atacgagatg tgactggagt tcagacgtgt gctcttccga tctgcttaat attagattta 60
aactattttt ctttcttttt agg 83

<210> SEQ ID NO 152
<211> LENGTH: 83
<212> TYPE: DNA
<213> ORGANISM: Artificial sequence
<220> FEATURE:
<223> OTHER INFORMATION: Synthetic

<400> SEQUENCE: 152
atacgagatg tgactggagt tcagacgtgt gctcttccga tctcaacaag gcattacctt 60
aaccaaagag agcaagcctt cag 83

<210> SEQ ID NO 153
<211> LENGTH: 83
<212> TYPE: DNA
<213> ORGANISM: Artificial sequence
<220> FEATURE:
<223> OTHER INFORMATION: Synthetic

<400> SEQUENCE: 153
atacgagatg tgactggagt tcagacgtgt gctcttccga tctaataaca atgtgggtac 60
tggaacctgt gacaaagtca ata 83

<210> SEQ ID NO 154
<211> LENGTH: 83
<212> TYPE: DNA
<213> ORGANISM: Artificial sequence
<220> FEATURE:
<223> OTHER INFORMATION: Synthetic

<400> SEQUENCE: 154
atacgagatg tgactggagt tcagacgtgt gctcttccga tctgatctgc ttctggttaa 60
ccacaaacct agtccacaga tca 83

<210> SEQ ID NO 155
<211> LENGTH: 83
<212> TYPE: DNA
<213> ORGANISM: Artificial sequence
<220> FEATURE:
<223> OTHER INFORMATION: Synthetic

<400> SEQUENCE: 155
atacgagatg tgactggagt tcagacgtgt gctcttccga tctttgctta gatgttgtag 60
tcaaatcaga tgtgagaagt att 83

<210> SEQ ID NO 156
<211> LENGTH: 83
<212> TYPE: DNA
<213> ORGANISM: Artificial sequence
<220> FEATURE:
<223> OTHER INFORMATION: Synthetic

<400> SEQUENCE: 156
atacgagatg tgactggagt tcagacgtgt gctcttccga tcttgatgaa ctttcccaca 60
ctaacctgca tgccttcaga act 83

<210> SEQ ID NO 157
<211> LENGTH: 83
<212> TYPE: DNA
<213> ORGANISM: Artificial sequence
<220> FEATURE:
<223> OTHER INFORMATION: Synthetic

<400> SEQUENCE: 157
atacgagatg tgactggagt tcagacgtgt gctcttccga tctaggtgtt gctgttgaaa 60
tggctgaaga tggtgaagag gca 83

<210> SEQ ID NO 158
<211> LENGTH: 83
<212> TYPE: DNA
<213> ORGANISM: Artificial sequence
<220> FEATURE:
<223> OTHER INFORMATION: Synthetic

<400> SEQUENCE: 158

```
atacgagatg tgactggagt tcagacgtgt gctcttccga tctaggaagt ccctcgacac     60

tggcagtgct gttaggtgtc tct                                             83


<210> SEQ ID NO 159
<211> LENGTH: 83
<212> TYPE: DNA
<213> ORGANISM: Artificial sequence
<220> FEATURE:
<223> OTHER INFORMATION: Synthetic

<400> SEQUENCE: 159

atacgagatg tgactggagt tcagacgtgt gctcttccga tctatgctgg gaaggcccag     60

tggaagagag aggtcgttca cca                                             83


<210> SEQ ID NO 160
<211> LENGTH: 83
<212> TYPE: DNA
<213> ORGANISM: Artificial sequence
<220> FEATURE:
<223> OTHER INFORMATION: Synthetic

<400> SEQUENCE: 160

atacgagatg tgactggagt tcagacgtgt gctcttccga tcttaatcag tatttaacat     60

ctttagagaa atttttcttc ctt                                             83


<210> SEQ ID NO 161
<211> LENGTH: 83
<212> TYPE: DNA
<213> ORGANISM: Artificial sequence
<220> FEATURE:
<223> OTHER INFORMATION: Synthetic

<400> SEQUENCE: 161

atacgagatg tgactggagt tcagacgtgt gctcttccga tctcaatgca atcatatgct     60

tctgctatgt taagcgtatt caa                                             83


<210> SEQ ID NO 162
<211> LENGTH: 83
<212> TYPE: DNA
<213> ORGANISM: Artificial sequence
<220> FEATURE:
<223> OTHER INFORMATION: Synthetic

<400> SEQUENCE: 162

atacgagatg tgactggagt tcagacgtgt gctcttccga tctaggatag agtgaagcga     60

cccatgaacg cattcatcgt gtg                                             83


<210> SEQ ID NO 163
<211> LENGTH: 83
<212> TYPE: DNA
<213> ORGANISM: Artificial sequence
<220> FEATURE:
<223> OTHER INFORMATION: Synthetic

<400> SEQUENCE: 163

atacgagatg tgactggagt tcagacgtgt gctcttccga tctgccacac ccactctgac     60

tcccataaaa cccagcggct ctg                                             83


<210> SEQ ID NO 164
<211> LENGTH: 83
<212> TYPE: DNA
<213> ORGANISM: Artificial sequence
```

<220> FEATURE:
<223> OTHER INFORMATION: Synthetic

<400> SEQUENCE: 164
atacgagatg tgactggagt tcagacgtgt gctcttccga tctgtctaga tttttctaga 60
ttttgtgtct gttttctcca gtt 83

<210> SEQ ID NO 165
<211> LENGTH: 83
<212> TYPE: DNA
<213> ORGANISM: Artificial sequence
<220> FEATURE:
<223> OTHER INFORMATION: Synthetic

<400> SEQUENCE: 165
atacgagatg tgactggagt tcagacgtgt gctcttccga tctagaaaga caaacaccgc 60
atgatcgcac tcatatgtca tat 83

<210> SEQ ID NO 166
<211> LENGTH: 83
<212> TYPE: DNA
<213> ORGANISM: Artificial sequence
<220> FEATURE:
<223> OTHER INFORMATION: Synthetic

<400> SEQUENCE: 166
atacgagatg tgactggagt tcagacgtgt gctcttccga tctagggctg gctctctgac 60
tgtgtcctct tcttacctgt ccc 83

<210> SEQ ID NO 167
<211> LENGTH: 83
<212> TYPE: DNA
<213> ORGANISM: Artificial sequence
<220> FEATURE:
<223> OTHER INFORMATION: Synthetic

<400> SEQUENCE: 167
atacgagatg tgactggagt tcagacgtgt gctcttccga tctcaaatgg ccggagctgg 60
accgaccatg ctgctacgag aag 83

<210> SEQ ID NO 168
<211> LENGTH: 83
<212> TYPE: DNA
<213> ORGANISM: Artificial sequence
<220> FEATURE:
<223> OTHER INFORMATION: Synthetic

<400> SEQUENCE: 168
atacgagatg tgactggagt tcagacgtgt gctcttccga tctgctgtag atcttcttcg 60
attgaccact gtgatggaaa ctg 83

<210> SEQ ID NO 169
<211> LENGTH: 83
<212> TYPE: DNA
<213> ORGANISM: Artificial sequence
<220> FEATURE:
<223> OTHER INFORMATION: Synthetic

<400> SEQUENCE: 169
atacgagatg tgactggagt tcagacgtgt gctcttccga tctagattat catatgagaa 60
ctcccttgaa attccaatac tca 83

<210> SEQ ID NO 170
<211> LENGTH: 83
<212> TYPE: DNA
<213> ORGANISM: Artificial sequence
<220> FEATURE:
<223> OTHER INFORMATION: Synthetic

<400> SEQUENCE: 170
atacgagatg tgactggagt tcagacgtgt gctcttccga tcttgctggg gccatcacga 60
tgtgtgggtg tccaggcctc cgg 83

<210> SEQ ID NO 171
<211> LENGTH: 43
<212> TYPE: DNA
<213> ORGANISM: Artificial sequence
<220> FEATURE:
<223> OTHER INFORMATION: Synthetic

<400> SEQUENCE: 171
agatcggaag agcacacgtc tgaactccag tcacauctcg uat 43

<210> SEQ ID NO 172
<211> LENGTH: 41
<212> TYPE: DNA
<213> ORGANISM: Artificial sequence
<220> FEATURE:
<223> OTHER INFORMATION: Synthetic

<400> SEQUENCE: 172
aatgatacgg cgaccaccga gatctacact ctttccctac a 41

<210> SEQ ID NO 173
<211> LENGTH: 44
<212> TYPE: DNA
<213> ORGANISM: Artificial sequence
<220> FEATURE:
<223> OTHER INFORMATION: Synthetic

<400> SEQUENCE: 173
caagcagaag acggcatacg agatgtgact ggagttcaga cgtg 44

<210> SEQ ID NO 174
<211> LENGTH: 21
<212> TYPE: DNA
<213> ORGANISM: Homo sapiens

<400> SEQUENCE: 174
aggggccacg cggggagcag c 21

<210> SEQ ID NO 175
<211> LENGTH: 21
<212> TYPE: DNA
<213> ORGANISM: Homo sapiens

<400> SEQUENCE: 175
aggggccacg gggggagcag c 21

<210> SEQ ID NO 176
<211> LENGTH: 21
<212> TYPE: DNA
<213> ORGANISM: Homo sapiens

<400> SEQUENCE: 176
aacatattga cggtgcctga a 21

<210> SEQ ID NO 177
<211> LENGTH: 20
<212> TYPE: DNA
<213> ORGANISM: Homo sapiens

<400> SEQUENCE: 177
aacatattga aggtgcctga 20

<210> SEQ ID NO 178
<211> LENGTH: 21
<212> TYPE: DNA
<213> ORGANISM: Homo sapiens

<400> SEQUENCE: 178
aggtgcttac acatgtttgt t 21

<210> SEQ ID NO 179
<211> LENGTH: 21
<212> TYPE: DNA
<213> ORGANISM: Homo sapiens

<400> SEQUENCE: 179
aggtgcttac gcatgtttgt t 21

<210> SEQ ID NO 180
<211> LENGTH: 21
<212> TYPE: DNA
<213> ORGANISM: Homo sapiens

<400> SEQUENCE: 180
atcccttcac ttcctcatcc t 21

<210> SEQ ID NO 181
<211> LENGTH: 21
<212> TYPE: DNA
<213> ORGANISM: Homo sapiens

<400> SEQUENCE: 181
atcccttcac gtcctcatcc t 21

<210> SEQ ID NO 182
<211> LENGTH: 21
<212> TYPE: DNA
<213> ORGANISM: Homo sapiens

<400> SEQUENCE: 182
tccccctccc gtagctcctg g 21

<210> SEQ ID NO 183
<211> LENGTH: 21
<212> TYPE: DNA
<213> ORGANISM: Homo sapiens

<400> SEQUENCE: 183
tccccctccc ctagctcctg g 21

<210> SEQ ID NO 184
<211> LENGTH: 21
<212> TYPE: DNA
<213> ORGANISM: Homo sapiens

<400> SEQUENCE: 184
ttgttagtgc ggatctgtgg t 21

<210> SEQ ID NO 185
<211> LENGTH: 21
<212> TYPE: DNA
<213> ORGANISM: Homo sapiens

<400> SEQUENCE: 185
ttgttagtgc agatctgtgg t 21

<210> SEQ ID NO 186
<211> LENGTH: 21
<212> TYPE: DNA
<213> ORGANISM: Homo sapiens

<400> SEQUENCE: 186
gcttctagga ctgggctgct t 21

<210> SEQ ID NO 187
<211> LENGTH: 21
<212> TYPE: DNA
<213> ORGANISM: Homo sapiens

<400> SEQUENCE: 187
gcttctagga ttgggctgct t 21

<210> SEQ ID NO 188
<211> LENGTH: 21
<212> TYPE: DNA
<213> ORGANISM: Homo sapiens

<400> SEQUENCE: 188
tactaagtct tgggacctct t 21

<210> SEQ ID NO 189
<211> LENGTH: 21
<212> TYPE: DNA
<213> ORGANISM: Homo sapiens

<400> SEQUENCE: 189
tactaagtct cgggacctct t 21

<210> SEQ ID NO 190
<211> LENGTH: 21
<212> TYPE: DNA
<213> ORGANISM: Homo sapiens

<400> SEQUENCE: 190
gggttggggt cggggtggtg g 21

<210> SEQ ID NO 191
<211> LENGTH: 21
<212> TYPE: DNA
<213> ORGANISM: Homo sapiens

<400> SEQUENCE: 191
gggttggggt gggggtggtg g 21

<210> SEQ ID NO 192
<211> LENGTH: 21
<212> TYPE: DNA
<213> ORGANISM: Homo sapiens

<400> SEQUENCE: 192
taagaggtgg gcccaggggt c 21

<210> SEQ ID NO 193
<211> LENGTH: 21
<212> TYPE: DNA
<213> ORGANISM: Homo sapiens

<400> SEQUENCE: 193
taagaggtgg acccaggggt c 21

<210> SEQ ID NO 194
<211> LENGTH: 21
<212> TYPE: DNA
<213> ORGANISM: Homo sapiens

<400> SEQUENCE: 194
ccagttttac tccaatctcc t 21

<210> SEQ ID NO 195
<211> LENGTH: 21
<212> TYPE: DNA
<213> ORGANISM: Homo sapiens

<400> SEQUENCE: 195
ccagttttac cccaatctcc t 21

<210> SEQ ID NO 196
<211> LENGTH: 21
<212> TYPE: DNA
<213> ORGANISM: Homo sapiens

<400> SEQUENCE: 196
cagttgatcc gacagcaaca g 21

<210> SEQ ID NO 197
<211> LENGTH: 21
<212> TYPE: DNA
<213> ORGANISM: Homo sapiens

<400> SEQUENCE: 197
cagttgatcc aacagcaaca g 21

<210> SEQ ID NO 198
<211> LENGTH: 21
<212> TYPE: DNA
<213> ORGANISM: Homo sapiens

<400> SEQUENCE: 198
gtaaccagca ctcgactctg c 21

<210> SEQ ID NO 199
<211> LENGTH: 21
<212> TYPE: DNA
<213> ORGANISM: Homo sapiens

<400> SEQUENCE: 199
gtaaccagca atcgactctg c 21

<210> SEQ ID NO 200
<211> LENGTH: 21
<212> TYPE: DNA
<213> ORGANISM: Homo sapiens

<400> SEQUENCE: 200
ggcagcgact cagcctgtcc t 21

<210> SEQ ID NO 201
<211> LENGTH: 21
<212> TYPE: DNA
<213> ORGANISM: Homo sapiens

<400> SEQUENCE: 201
ggcagcgact tagcctgtcc t 21

<210> SEQ ID NO 202
<211> LENGTH: 21
<212> TYPE: DNA
<213> ORGANISM: Homo sapiens

<400> SEQUENCE: 202
tgctaacccc agcactggag c 21

<210> SEQ ID NO 203
<211> LENGTH: 21
<212> TYPE: DNA
<213> ORGANISM: Homo sapiens

<400> SEQUENCE: 203
tgctaacccc ggcactggag c 21

<210> SEQ ID NO 204
<211> LENGTH: 21
<212> TYPE: DNA
<213> ORGANISM: Homo sapiens

<400> SEQUENCE: 204
caatgtcaaa tgggaaaaag t 21

<210> SEQ ID NO 205
<211> LENGTH: 21
<212> TYPE: DNA
<213> ORGANISM: Homo sapiens

<400> SEQUENCE: 205
caatgtcaaa cgggaaaaag t 21

<210> SEQ ID NO 206
<211> LENGTH: 21
<212> TYPE: DNA
<213> ORGANISM: Homo sapiens

<400> SEQUENCE: 206
gacaggagga caggataaaa g 21

<210> SEQ ID NO 207
<211> LENGTH: 21
<212> TYPE: DNA
<213> ORGANISM: Homo sapiens

<400> SEQUENCE: 207
gacaggagga aaggataaaa g 21

<210> SEQ ID NO 208
<211> LENGTH: 21
<212> TYPE: DNA
<213> ORGANISM: Homo sapiens -continued

<400> SEQUENCE: 208
ggacctagat gccaggacca t 21

<210> SEQ ID NO 209
<211> LENGTH: 21
<212> TYPE: DNA
<213> ORGANISM: Homo sapiens

<400> SEQUENCE: 209
ggacctagat tccaggacca t 21